US012616769B2

(12) United States Patent
Hamberg et al.

(10) Patent No.: US 12,616,769 B2
(45) Date of Patent: May 5, 2026

(54) BIOLOGICAL INDICATOR READER WITH GRAPHICAL USER INTERFACE AND METHODS OF USE

(71) Applicant: Crosstex International, Inc., Hauppauge, NY (US)

(72) Inventors: Keith Hamberg, Excelsior, MN (US); John C. Houge, Maple Grove, MN (US); Greg Ingersoll, Minneapolis, MN (US); Michael Scheidnes, Maple Grove, MN (US); Jeanette Sterner, Burnsville, MN (US)

(73) Assignee: CROSSTEX INTERNATIONAL, INC., Hauppauge, NY (US)

( * ) Notice: Subject to any disclaimer, the term of this patent is extended or adjusted under 35 U.S.C. 154(b) by 502 days.

(21) Appl. No.: 18/259,830

(22) PCT Filed: Dec. 22, 2021

(86) PCT No.: PCT/US2021/064821
§ 371 (c)(1),
(2) Date: Jun. 29, 2023

(87) PCT Pub. No.: WO2022/150193
PCT Pub. Date: Jul. 14, 2022

(65) Prior Publication Data
US 2024/0058498 A1     Feb. 22, 2024

Related U.S. Application Data

(60) Provisional application No. 63/134,429, filed on Jan. 6, 2021, provisional application No. 63/134,432, filed
(Continued)

(51) Int. Cl.
*A61L 2/28*          (2006.01)
*A61L 2/10*          (2006.01)
(Continued)

(52) U.S. Cl.
CPC ................... *A61L 2/28* (2013.01); *A61L 2/10* (2013.01); *A61L 2/24* (2013.01); *C12Q 1/22* (2013.01);
(Continued)

(58) Field of Classification Search
None
See application file for complete search history.

(56) References Cited

U.S. PATENT DOCUMENTS 4,448,534 A      5/1984  Wertz et al.
5,334,841 A      8/1994  Graessle et al.
(Continued)

FOREIGN PATENT DOCUMENTS

EP          0055027 A2      6/1982
WO      2005036128 A2      4/2005
(Continued)

OTHER PUBLICATIONS

International Search Report and Written Opinion of the International Searching Authority Dated Mar. 15, 2022, of International PCT Application No. PCT/US2021/064816 filed Dec. 22, 2021.
(Continued)

*Primary Examiner* — Brian R Gordon
(74) *Attorney, Agent, or Firm* — MARSHALL, GERSTEIN & BORUN LLP

(57)          ABSTRACT
A biological indicator reader is provided for reading a plurality of biological indicators to determine the effectiveness of at least a sterilization process. Each biological indicator is configured to exhibit fluorescence when the sterilization process has failed. Each reader comprises a housing having a plurality of biological indicator holders, a heater coupled to the housing and configured to heat the plurality of biological indicator holders to a preselected temperature to incubate the biological indicators, a UV light emitter configured to emit UV light through a first aperture
(Continued)

on the side of each holder and an optical detector positioned under a second aperture on the bottom of the biological indicator holder, the optical detector configured to detect fluorescence intensity indicating the effectiveness of the sterilization process. A method of using the biological indicator reader is provided. A biological indicator system and display are also provided.

20 Claims, 40 Drawing Sheets

Related U.S. Application Data on Jan. 6, 2021, provisional application No. 63/134,433, filed on Jan. 6, 2021.

(51) Int. Cl.
| | |
|---|---|
| *A61L 2/24* | (2006.01) |
| *C12Q 1/22* | (2006.01) |
| *G01N 21/64* | (2006.01) |
| *G01N 21/77* | (2006.01) |

(52) U.S. Cl.
CPC ..... *G01N 21/6428* (2013.01); *G01N 21/6486* (2013.01); *G01N 21/77* (2013.01); *A61L 2202/11* (2013.01); *A61L 2202/14* (2013.01); *G01N 2021/6439* (2013.01); *G01N 2201/062* (2013.01)

(56) References Cited

U.S. PATENT DOCUMENTS

| | | | |
|---|---|---|---|
| 5,500,184 | A | 3/1996 | Palmer |
| 5,736,355 | A | 4/1998 | Dyke et al. |
| 5,739,004 | A | 4/1998 | Woodson |
| 5,770,393 | A | 6/1998 | Dalmasso et al. |
| 5,795,730 | A | 8/1998 | Tautvydas |
| 5,801,010 | A | 9/1998 | Falkowski et al. |
| 5,858,769 | A | 1/1999 | Diguiseppi et al. |
| 5,863,790 | A * | 1/1999 | Bolea ........................ A61L 2/28 |
| | | | 435/287.4 |
| 6,037,598 | A | 3/2000 | Cicha |
| 6,329,207 | B1 | 12/2001 | Fricker et al. |
| 6,436,659 | B1 | 8/2002 | Hui et al. |
| 6,485,978 | B1 | 11/2002 | Kirckof et al. |
| 6,485,979 | B1 | 11/2002 | Kippenhan et al. |
| 6,524,846 | B1 | 2/2003 | Robinson, Jr. |
| 6,528,277 | B1 | 3/2003 | Hendricks et al. |
| 6,541,777 | B1 | 4/2003 | Lombardo et al. |
| 6,592,816 | B1 | 7/2003 | Ebel et al. |
| 6,623,955 | B2 | 9/2003 | Matner et al. |
| 6,791,092 | B2 | 9/2004 | Hamilton |
| 6,884,394 | B1 | 4/2005 | Hehenberger et al. |
| 6,924,139 | B2 | 8/2005 | Eveland et al. |
| 7,122,150 | B2 | 10/2006 | Gonzalez et al. |
| 7,247,482 | B2 | 7/2007 | Lemus et al. |
| 7,326,562 | B2 | 2/2008 | Felkner et al. |
| 7,483,805 | B2 | 1/2009 | Sparks et al. |
| 7,563,616 | B2 | 7/2009 | Gillis et al. |
| 7,670,552 | B2 | 3/2010 | Read |
| 7,790,105 | B2 | 9/2010 | Bala |
| 7,899,681 | B2 | 3/2011 | Katzenmaier et al. |
| 7,968,854 | B2 | 6/2011 | Hormann |
| 8,173,388 | B2 | 5/2012 | Pasmore et al. |
| 8,283,133 | B2 | 10/2012 | Franciskovich et al. |
| 8,343,768 | B2 | 1/2013 | Kyung-Hee Song et al. |
| 8,394,344 | B2 | 3/2013 | Schutt et al. |
| 8,546,132 | B1 | 10/2013 | Lewis et al. |
| 8,652,412 | B2 | 2/2014 | Hyde et al. |
| 8,858,884 | B2 | 10/2014 | Franciskovich et al. |
| 8,883,490 | B2 * | 11/2014 | Handique ......... B01L 3/502723 |
| | | | 435/808 |

| | | | |
|---|---|---|---|
| 8,906,693 | B2 | 12/2014 | Schultz et al. |
| 8,969,029 | B2 | 3/2015 | Chandrapati et al. |
| 9,012,209 | B2 | 4/2015 | Eden et al. |
| 9,068,976 | B2 | 6/2015 | Putnam et al. |
| 9,121,050 | B2 | 9/2015 | Franciskovich et al. |
| 9,145,573 | B2 * | 9/2015 | Pederson .................. A61L 2/28 |
| 9,186,430 | B2 | 11/2015 | Dane et al. |
| 9,207,180 | B2 | 12/2015 | Eden |
| 9,303,283 | B2 * | 4/2016 | Franciskovich ......... C12Q 1/22 |
| 9,316,590 | B2 | 4/2016 | Chang et al. |
| 9,410,180 | B2 * | 8/2016 | Pederson .................. A61L 2/28 |
| 9,428,786 | B2 * | 8/2016 | Pederson ................. C12Q 1/22 |
| 9,540,677 | B2 | 1/2017 | Smith et al. |
| 9,687,575 | B2 | 6/2017 | Farren |
| 9,701,996 | B2 | 7/2017 | Smith et al. |
| 10,047,334 | B2 | 8/2018 | Chandrapati et al. |
| 10,059,977 | B2 | 8/2018 | Witcher et al. |
| 10,195,299 | B2 | 2/2019 | Baker et al. |
| 10,443,083 | B2 * | 10/2019 | Eghbal ...................... A61L 2/28 |
| 10,632,220 | B2 * | 4/2020 | Fang .......................... A61L 2/16 |
| 11,390,901 | B2 * | 7/2022 | Eghbal ..................... C12Q 1/22 |
| 11,603,551 | B2 * | 3/2023 | Ponce ...................... C12Q 1/22 |
| 12,371,649 | B2 * | 7/2025 | Ji ........................ G01N 21/6456 |
| 12,390,546 | B2 * | 8/2025 | Ludowise ............... C12Q 1/22 |
| 12,410,459 | B2 * | 9/2025 | Ponce ...................... C12Q 1/22 |
| 12,507,815 | B2 * | 12/2025 | Musilli ................... A47F 10/00 |
| 2001/0021356 | A1 | 9/2001 | Konrad |
| 2002/0058296 | A1 | 5/2002 | Miller et al. |
| 2002/0162970 | A1 | 11/2002 | Sasges |
| 2004/0197848 | A1 | 10/2004 | Behun et al. |
| 2004/0200975 | A1 | 10/2004 | Brown et al. |
| 2006/0263258 | A1 * | 11/2006 | Harris ...................... A61L 2/28 |
| | | | 422/400 |
| 2008/0297864 | A1 | 12/2008 | Horgan et al. |
| 2011/0210257 | A9 | 9/2011 | Handique et al. |
| 2013/0210069 | A1 * | 8/2013 | Pederson .................. A61L 2/28 |
| | | | 435/288.7 |
| 2013/0217107 | A1 * | 8/2013 | Pederson ................. C12Q 1/22 |
| | | | 435/287.4 |
| 2013/0230910 | A1 | 9/2013 | Christensen et al. |
| 2013/0273594 | A1 | 10/2013 | Ahimou et al. |
| 2014/0271370 | A1 | 9/2014 | Sirotin et al. |
| 2014/0370535 | A1 | 12/2014 | Chandrapati et al. |
| 2015/0147408 | A1 | 5/2015 | Berry et al. |
| 2015/0335777 | A1 | 11/2015 | Robbins et al. |
| 2016/0109337 | A1 | 4/2016 | Valkenier et al. |
| 2017/0023555 | A1 | 1/2017 | Ou et al. |
| 2017/0037447 | A1 | 2/2017 | Chandrapati et al. |
| 2017/0247742 | A1 | 8/2017 | Doyle et al. |
| 2017/0253905 | A1 * | 9/2017 | Eghbal ............ G01N 33/48792 |
| 2018/0015193 | A1 | 1/2018 | Swaminathan et al. |
| 2018/0104015 | A1 | 4/2018 | Bryant et al. |
| 2018/0237821 | A1 * | 8/2018 | Fryer .............. C12Y 302/0102 |
| 2018/0245122 | A1 | 8/2018 | Soto et al. |
| 2018/0252701 | A1 | 9/2018 | Rhodes et al. |
| 2018/0355400 | A1 | 12/2018 | Centanni et al. |
| 2019/0002951 | A1 | 1/2019 | Fryer et al. |
| 2019/0017091 | A1 | 1/2019 | Centanni et al. |
| 2019/0017092 | A1 | 1/2019 | Franciskovich et al. |
| 2019/0017093 | A1 | 1/2019 | Franciskovich et al. |
| 2019/0117810 | A1 * | 4/2019 | Ludowise ................. A61L 2/24 |
| 2019/0125912 | A1 | 5/2019 | Bommarito et al. |
| 2019/0169672 | A1 | 6/2019 | Fryer et al. |
| 2020/0199516 | A1 * | 6/2020 | Rhodes .................. A01N 25/02 |
| 2021/0402033 | A1 * | 12/2021 | Ludowise .............. C12M 37/06 |
| 2022/0275422 | A1 * | 9/2022 | Ponce ...................... C12Q 1/22 |
| 2022/0275423 | A1 * | 9/2022 | Ponce ...................... C12Q 1/22 |
| 2023/0173118 | A1 * | 6/2023 | Zuegel .................... B65B 5/103 |
| | | | 422/24 |
| 2024/0252707 | A1 * | 8/2024 | Qi ......................... H04N 1/1215 |
| 2025/0099641 | A1 * | 3/2025 | Ludowise .............. C12M 37/06 |

FOREIGN PATENT DOCUMENTS

| | | | |
|---|---|---|---|
| WO | 2018025207 | A1 | 2/2018 |
| WO | 2019164075 | A1 | 8/2019 |
| WO | 2020023833 | A1 | 1/2020 |
| WO | 2020128959 | A1 | 6/2020 |

(56)        References Cited

FOREIGN PATENT DOCUMENTS

| WO | 2020136608 | A1 | 7/2020 |
| WO | 2020136613 | A1 | 7/2020 |
| WO | 2020183433 | A1 | 9/2020 |
| WO | 2020183434 |    | 9/2020 |
| WO | 2022150191 | A1 | 7/2022 |
| WO | 2022150192 | A1 | 7/2022 |
| WO | WO2022150193 | A1 | 7/2022 |

OTHER PUBLICATIONS

International Search Report and Written Opinion of the International Searching Authority Dated Mar. 16, 2022, of International PCT Application No. PCT/US2021/064818 filed Dec. 22, 2021.
International Search Report and Written Opinion of the International Searching Authority Dated Mar. 25, 2022, of International PCT Application No. PCT/US2021/064821 filed Dec. 22, 2021.

\* cited by examiner

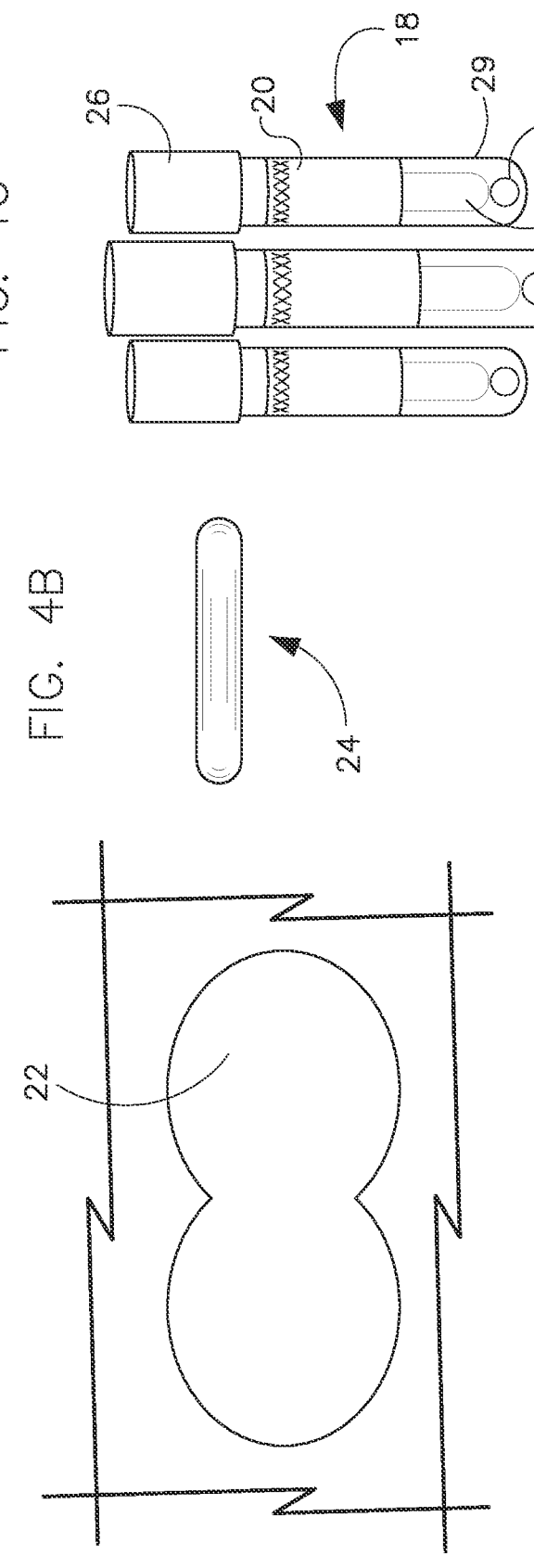
FIG. 4A
FIG. 4B
FIG. 4C
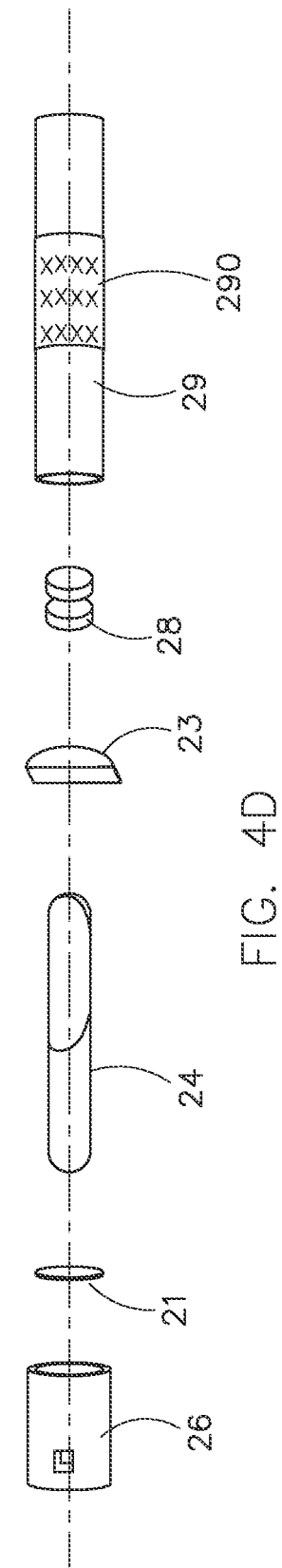
FIG. 4D read only textbox

Figures 21A, 21B:
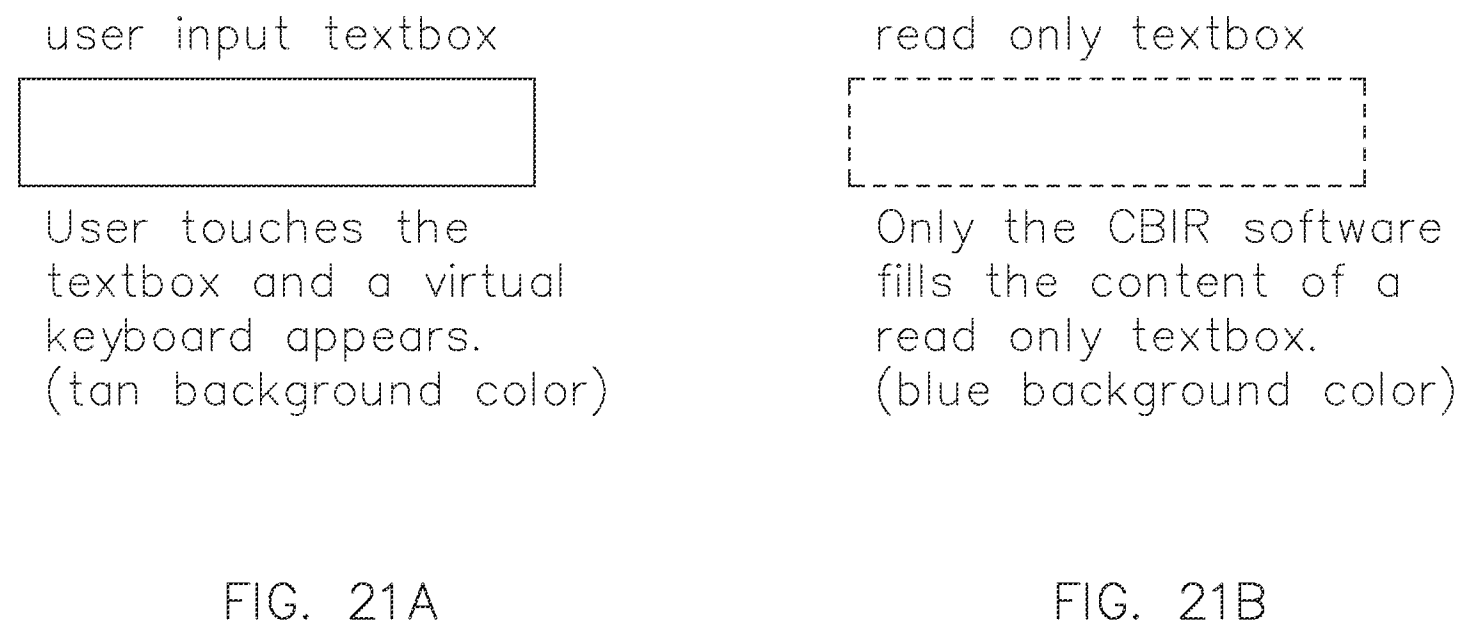

Only the CBIR software
fills the content of a
read only textbox.
(blue background color)

FIG. 21B user input textbox

User touches the
textbox and a virtual
keyboard appears.
(tan background color)

HISTORY LOG

☰ MENU

XXXXXXX

| ENTRY | WELL | CTRL | NEG/POS | DATE | START | STOP |
|-------|------|------|---------|------|-------|------|
| 91 | 1 | NO | POS | 2019—03—14 | 01:23 PM | 01:53 PM |
| 92 | 2 | YES | POS | YYYY—MM—DD | HH:MM AP | HH:MM AP |
| 93 | 3 | YES | NEG | YYYY—MM—DD | HH:MM AP | HH:MM AP |
| 94 | 4 | NO | NEG | YYYY—MM—DD | HH:MM AP | HH:MM AP |
| 95 | 6 | NO | POS | YYYY—MM—DD | HH:MM AP | HH:MM AP |
| 96 | 7 | NO | NEG | YYYY—MM—DD | HH:MM AP | HH:MM AP |
| 97 | 1 | YES | NEG | YYYY—MM—DD | HH:MM AP | HH:MM AP |
| 98 | 2 | NO | NEG | YYYY—MM—DD | HH:MM AP | HH:MM AP |
| 99 | 3 | NO | POS | YYYY—MM—DD | HH:MM AP | HH:MM AP |
| 100 | 12 | YES | POS | YYYY—MM—DD | HH:MM AP | HH:MM AP |

ERROR LOG

XXXXXX    ≡ MENU

| ENTRY | ERROR | DATE | TIME | WELL |
|---|---|---|---|---|
| 91 | YES | 2019-03-14 | 01:23 PM | 2,5,6,7.9,10,11 |
| 92 | NO | YYYY-MM-DD | HH:MM AP | 1,2,3,4,5,6,7,8,9,10,11,12 |
| 93 | NO | YYYY-MM-DD | HH:MM AP | 1,2,3,4,5,6,7,8,9,10,11,12 |
| 94 | NO | YYYY-MM-DD | HH:MM AP | 1,2,3,4,5,6,7,8,9,10,11,12 |
| 95 | YES | YYYY-MM-DD | HH:MM AP | 1,2,3,4,5,6,7,8,9,10,11,12 |
| 96 | NO | YYYY-MM-DD | HH:MM AP | 1,2,3,4,5,6,7,8,9,10,11,12 |
| 97 | NO | YYYY-MM-DD | HH:MM AP | 1,2,3,4,5,6,7,8,9,10,11,12 |
| 98 | NO | YYYY-MM-DD | HH:MM AP | 1,2,3,4,5,6,7,8,9,10,11,12 |
| 99 | YES | YYYY-MM-DD | HH:MM AP | 1,2,3,4,5,6,7,8,9,10,11,12 |
| 100 | NO | YYYY-MM-DD | HH:MM AP | 1,2,3,4,5,6,7,8,9,10,11,12 |

BIOLOGICAL INDICATOR READER WITH GRAPHICAL USER INTERFACE AND METHODS OF USE

CROSS REFERENCE TO RELATED APPLICATIONS

This application claims priority to U.S. Provisional Patent Application with Ser. No. 63/134,433 filed, Jan. 6, 2021, and claims priority to U.S. Provisional Patent Application with Ser. No. 63/134,432 filed Jan. 6, 2021, and claims priority to U.S. Provisional Patent Application with Ser. No. 63/134, 429 filed Jan. 6, 2021. These applications are incorporated herein by reference, in their entireties.

BACKGROUND

Sterilization is a process conducted in a specially designed chamber or sterilizer that results hopefully in a complete eradication of all viable microorganisms that may be living on medical, dental or surgical instruments. Sterilization techniques have evolved over time from the traditional methods employing saturated steam at elevated temperature and ethylene oxide gases to more modern techniques such as those employing liquid, vapor, and plasma. The effectiveness of the sterilization process must be evaluated regardless of the technique used especially when a medical, dental or surgical instrument is going to be used on or in the human body.

Biological indicators are devices that are used to test the efficacy of sterilization chambers such as those employed in healthcare facilities and laboratories for sterilizing medical, dental or surgical instruments. A biological indicator provides information on whether necessary conditions were met to kill a specified number of microorganisms for a given sterilization process, which provides the user a certain level of confidence in their particular sterilization process.

A typical biological indicator being used today is a self-contained biological indicator (SCBI), which contains, among other things, microorganisms, culture medium, carrier, and a crushable container (e.g., vial). After the biological indicator is exposed to a sterilization process, the crushable container of the biological indicator is crushed or activated and placed in a biological indicator reader, which has, among other things, an incubator, a UV light emitter and an optical detector.

Any microorganism remaining in the biological indicator, after the sterilization process, is incubated in the culture medium after the indicator is activated. Metabolism of the culture medium by viable microorganisms surviving in the medium will cause a fluorescent signal on exposure of the medium to UV light. This fluorescent signal, if intense enough, will be detected by the optical detector indicating a sterilization failure during the sterilization process, where the proper conditions (e.g., time, temperature, position in the sterilizer, etc.) for sterilization were not met. Medical, dental or surgical instruments not properly sterilized can potentially contaminate patients if used.

Unfortunately, some biological indicator readers currently available provide inaccurate results on whether the proper conditions were met to kill a specified number of microorganisms for a given sterilization process. These biological indicator readers fail to provide the user with confidence that the proper sterilization process has occurred. Thus, there is a need for an improved biological indicator reader, system, and method, which reduce inaccurate results of the sterilization process.

SUMMARY

A biological indicator reader for reading a plurality of biological indicators to determine the effectiveness of at least a sterilization process is provided. Each biological indicator is configured to exhibit fluorescence when the sterilization process has failed, the reader comprising a housing having a plurality of biological indicator holders, each holder configured to receive one of the plurality of biological indicators, each biological indicator holder having a first aperture and a second aperture; a heater coupled to the housing and configured to heat the plurality of biological indicator holders to a preselected temperature to incubate the biological indicators; a UV light emitter configured to emit UV light through the first aperture of each holder; an optical detector positioned adjacent to the second aperture of the biological indicator holder, the optical detector configured to detect fluorescence intensity indicating the effectiveness of the sterilization process; and a controller coupled to the optical detector, the controller configured to receive an input signal emitted when the optical detector receives light exiting each biological indicator holder and to provide an output signal indicating sterilization process failure or success on a graphical user interface.

A biological indicator system for detecting the effectiveness of a sterilization process is provided. The system comprises a biological indicator reader for reading a plurality of biological indicators to determine the effectiveness of at least a sterilization process, each biological indicator configured to exhibit fluorescence when the sterilization process has failed, the reader comprising a housing having a plurality of biological indicator holders, each holder configured to receive one of the plurality of biological indicators, each biological indicator holder having a first aperture and a second aperture; a heater coupled to the housing and configured to heat the plurality of biological indicator holders to a preselected temperature and a preselected period of time to incubate the biological indicators; a UV light emitter configured to emit UV light through the first aperture; and an optical detector positioned adjacent to the second aperture of the biological indicator holder, the optical detector configured to detect fluorescence intensity indicating the effectiveness of the sterilization process; a controller coupled to the optical detector, the controller configured to receive an input signal emitted when the optical detector receives light exiting each biological indicator holder and to provide an output signal indicating sterilization process failure or success on a graphical user interface; and a biological indicator containing spores, growth media containing a fluorescent moiety, and a crushable container, the biological indicator being sterilizable and configured to receive UV light from the UV light emitter.

A method for determining the effectiveness of at least a sterilization process is provided. The method comprises providing a biological indicator reader for reading a plurality of biological indicators to determine the effectiveness of at least a sterilization process, each biological indicator configured to exhibit fluorescence when the sterilization process has failed, the reader comprising a housing having a plurality of biological indicator holders, each holder configured to receive one of the plurality of biological indicators, each biological indicator holder having a first aperture and a second aperture; a heater coupled to the housing and configured to heat the plurality of biological indicator holders to a preselected temperature to incubate the biological indicators; a UV light emitter configured to emit UV light through the first aperture; an optical detector positioned adjacent to the second aperture, the optical detector configured to detect fluorescence intensity indicating the effectiveness of the sterilization process; providing a biological indicator capable of exhibiting fluorescence to indicate the effectiveness of a sterilization process, the biological indicator comprising a crushable container; subjecting the biological indicator to the sterilization process to obtain a sterilized biological indicator, crushing the crushable container of the sterilized biological indicator to activate the indicator; incubating the activated biological indicator in one of the biological indicator holders of the biological indicator at a preselected temperature and for a preselected period of time; emitting UV light through the first aperture of each biological indicator holder; detecting fluorescence intensity by the optical detector indicating the effectiveness of the sterilization process, the optical detector coupled to a controller, the controller configured to receive an input signal emitted when the optical detector receives light exiting each biological indicator holder and to provide an output signal indicating sterilization process failure or success on a graphical user interface.

A biological indicator reader for reading a plurality of biological indicators to determine the effectiveness of at least a sterilization process is provided. In some embodiments, the reader comprises a housing having a UV light emitter coupled to the housing, the UV light emitter configured to emit UV light for a period of time; an optical detector configured to detect UV light; a multiplexer coupled to the optical detector, the multiplexer configured to generate an input signal from the optical detector; an amplifier coupled to the multiplexer, the amplifier configured to integrate a plurality of input signals for a period of time to indicate the effectiveness of the sterilization process based on the integration of the plurality of input signals.

A biological indicator reader for reading a plurality of biological indicators to determine the effectiveness of at least a sterilization process is also provided. In one embodiment, the reader comprises a housing having a plurality of biological indicator holders, a UV light emitter coupled to the housing, the UV light emitter configured to emit UV light for a period of time; an optical detector configured to detect UV light; a multiplexer coupled to the optical detector, the multiplexer configured to select an input signal from the optical detector; an amplifier coupled to the multiplexer, the amplifier configured to integrate a plurality of input signals for a period of time to indicate the effectiveness of the sterilization process based on the integration of the plurality of input signals, wherein the UV light emitter, the optical detector, the multiplexer, and the amplifier are coupled to a processor.

A biological indicator reader for reading a plurality of biological indicators to determine the effectiveness of at least a sterilization process is also provided. In some embodiments, the reader comprises a housing having a plurality of biological indicator holders, a UV light emitter coupled to the housing, the UV light emitter configured to emit UV light for a period of time; an optical detector configured to detect UV light; a multiplexer coupled to the optical detector, the multiplexer configured to select an input signal from the optical detector; an amplifier coupled to the multiplexer, the amplifier configured to integrate a plurality of input signals for a period of time to indicate the effectiveness of the sterilization process based on the integration of the plurality of input signals, wherein the UV light emitter, the optical detector, the multiplexer, and the amplifier are coupled to a processor.

A method for determining the effectiveness of at least a sterilization process is also provided. In one embodiment, the method comprises providing a biological indicator reader for reading a plurality of biological indicators to determine the effectiveness of at least a sterilization process to determine the effectiveness of at least a sterilization process, each biological indicator configured to exhibit fluorescence when the sterilization process has failed; placing each biological indicator inside a biological indicator crusher of the reader to activate the biological indicator; placing the activated biological indicator in a biological indicator holder for the detection of fluorescence; incubating the activated biological indicator at a preselected temperature for a preselected time; emitting UV light from a UV light emitter through an aperture on a side of the biological indicator holder; and detecting fluorescence intensity by an optical detector positioned at a bottom of the reader indicating the effectiveness of the sterilization process.

A biological indicator (BI) reader is provided that reduces inaccurate results of the sterilization process. In one embodiment, there is a biological indicator (BI) reader for reading a plurality of biological indicators to determine the effectiveness of at least a sterilization process. Each biological indicator is configured to exhibit increased fluorescence when the sterilization process has failed. Each BI reader comprises a housing having a plurality of biological indicator holders, each holder configured to receive one of the plurality of biological indicators, each biological indicator holder having a first aperture on a side and a second aperture on a bottom of the biological indicator holder. The biological indicator reader also includes a heater which is coupled to the housing and configured to heat the plurality of biological indicator holders to a preselected temperature to incubate the biological indicators. The biological indicator reader further includes a UV light emitter configured to emit UV light incident upon a BI through a first aperture on the side of each BI holder and an optical detector positioned under a second aperture directly below the bottom of the biological indicator holder, the optical detector configured to detect fluorescence intensity indicating the effectiveness of the sterilization process.

A method for determining the effectiveness of at least a sterilization process is also provided. The method comprises providing a biological indicator reader for reading a plurality of biological indicators to determine the effectiveness of at least a sterilization process, each biological indicator configured to exhibit fluorescence when the sterilization process has failed, the reader comprising a housing having a plurality of biological indicator holders, each holder configured to receive one of the plurality of biological indicators, each biological indicator holder having a first aperture on a side and a second aperture on a bottom of the biological indicator holder; a heater coupled to the housing and configured to heat the plurality of biological indicator holders to a preselected temperature to incubate the biological indicators; a UV light emitter configured to emit UV light through the first aperture on the side of each biological indicator holder; an optical detector positioned under the second aperture on the bottom of the biological indicator holder, the optical detector configured to detect fluorescence intensity indicating the effectiveness of the sterilization process.

The method also includes providing a biological indicator capable of exhibiting fluorescence to indicate the effectiveness of a sterilization process, the biological indicator comprising a crushable container; subjecting the biological indicator to the sterilization process to obtain a sterilized biological indicator; crushing the crushable container of the sterilized biological indicator to activate the biological indicator; incubating the activated biological indicator in one of the biological indicator holders of the biological indicator at a preselected temperature and for a preselected period of time; emitting UV light through the first aperture on the side of each biological indicator holder; and detecting fluorescence intensity by the optical detector indicating the effectiveness of the sterilization process.

A biological indicator system for detecting the effectiveness of a sterilization process is also provided. In many aspects, the system described in this disclosure comprises a biological indicator reader for reading a plurality of biological indicators to determine the effectiveness of at least a sterilization process, each biological indicator configured to exhibit fluorescence when the sterilization process has failed. In some embodiments, the biological indicator reader comprises a housing having a plurality of biological indicator holders, each holder configured to receive one of the plurality of biological indicators. In other embodiments, each biological indicator holder has a first aperture on a side of the biological indicator holder and a second aperture on a bottom of the biological indicator holder. The biological indicator reader also includes a heater coupled to the housing and configured to heat the plurality of biological indicator holders to a preselected temperature and a preselected period of time to incubate the biological indicators; a UV light emitter configured to emit UV light through the first aperture on the side of each holder; and an optical detector positioned under the second aperture on the bottom of the biological indicator holder, the optical detector configured to detect fluorescence intensity indicating the effectiveness of the sterilization process; and a biological indicator containing spores, growth media containing a fluorescent moiety and a crushable container, the biological indicator being sterilizable and configured to receive UV light from the UV light emitter.

While multiple embodiments are disclosed, still other embodiments of the present disclosure will become apparent to those skilled in the art from the following detailed description, which shows and describes illustrative embodiments of the disclosure. As will be realized, the various embodiments of the present disclosure are capable of modifications in various obvious aspects, all without departing from the spirit and scope of the present disclosure. Accordingly, the detailed description is to be regarded as illustrative in nature and not restrictive.

BRIEF DESCRIPTION OF DRAWINGS

In part, other aspects, features, benefits and advantages of the embodiments will be apparent with regard to the following description, appended claims and accompanying drawings where:

biological indicator holders or wells and a heater element for heating the same during the sterilization process.

Figures 3A, 3B:
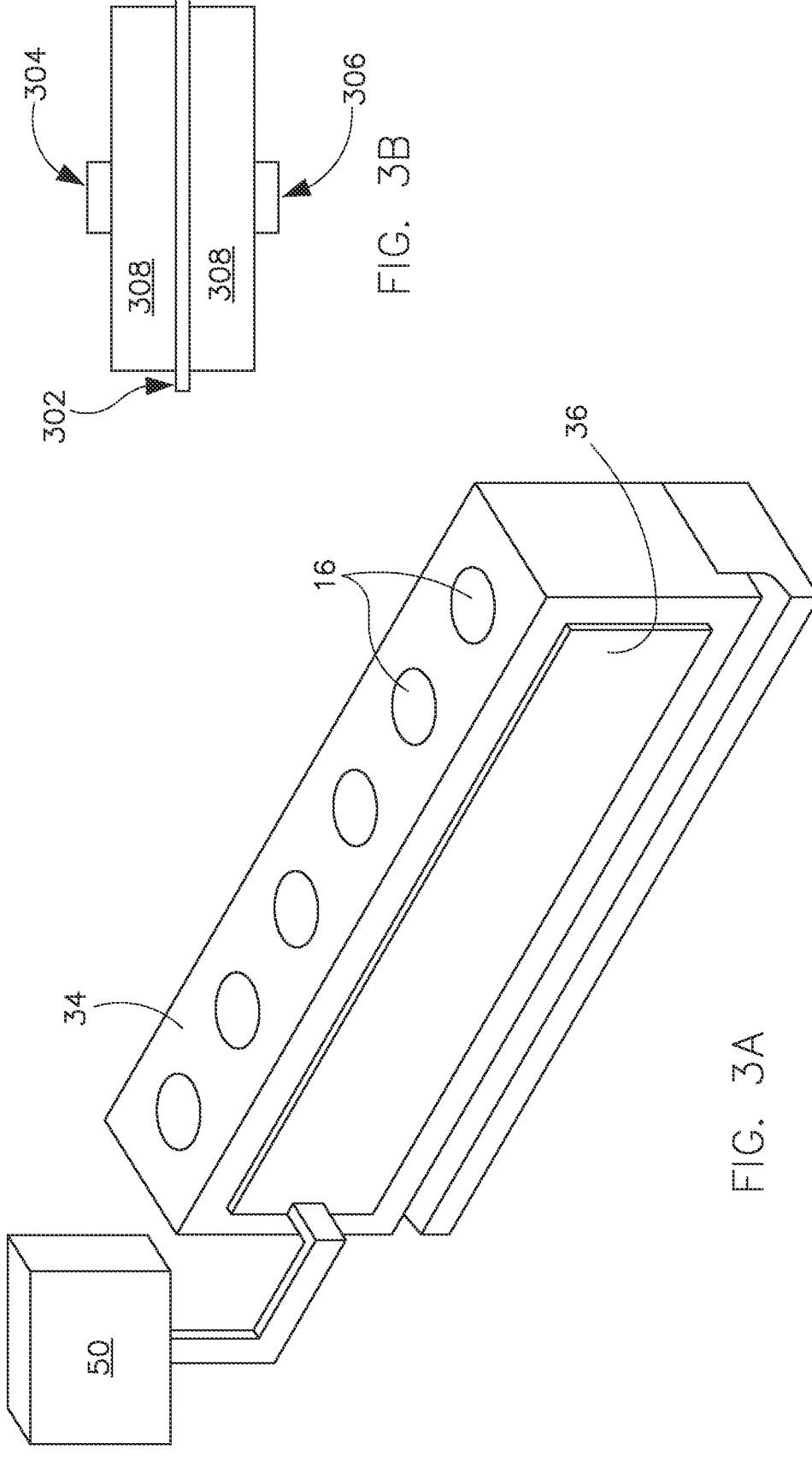
FIG. 3A is a perspective view of one embodiment of a biological indicator reader showing a block of six (6)

FIG. 3B illustrates an embodiment of a heater control.

FIG. 4A is an enlarged view of a biological indicator crusher.

FIG. 4B is a perspective view of a growth media ampoule.

FIG. 4C is a perspective view of three (3) biological indicators.

FIG. 4D is a dissembled view of a biological indicator.

Figure 5:
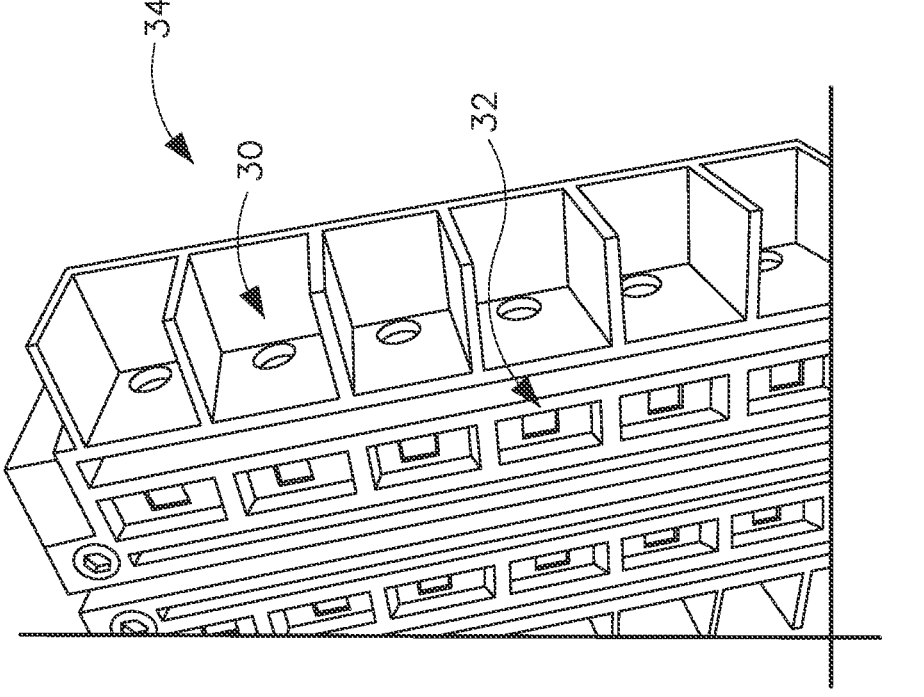

FIG. 5 is a perspective bottom view of a block of biological indicator holders.

Figure 6:
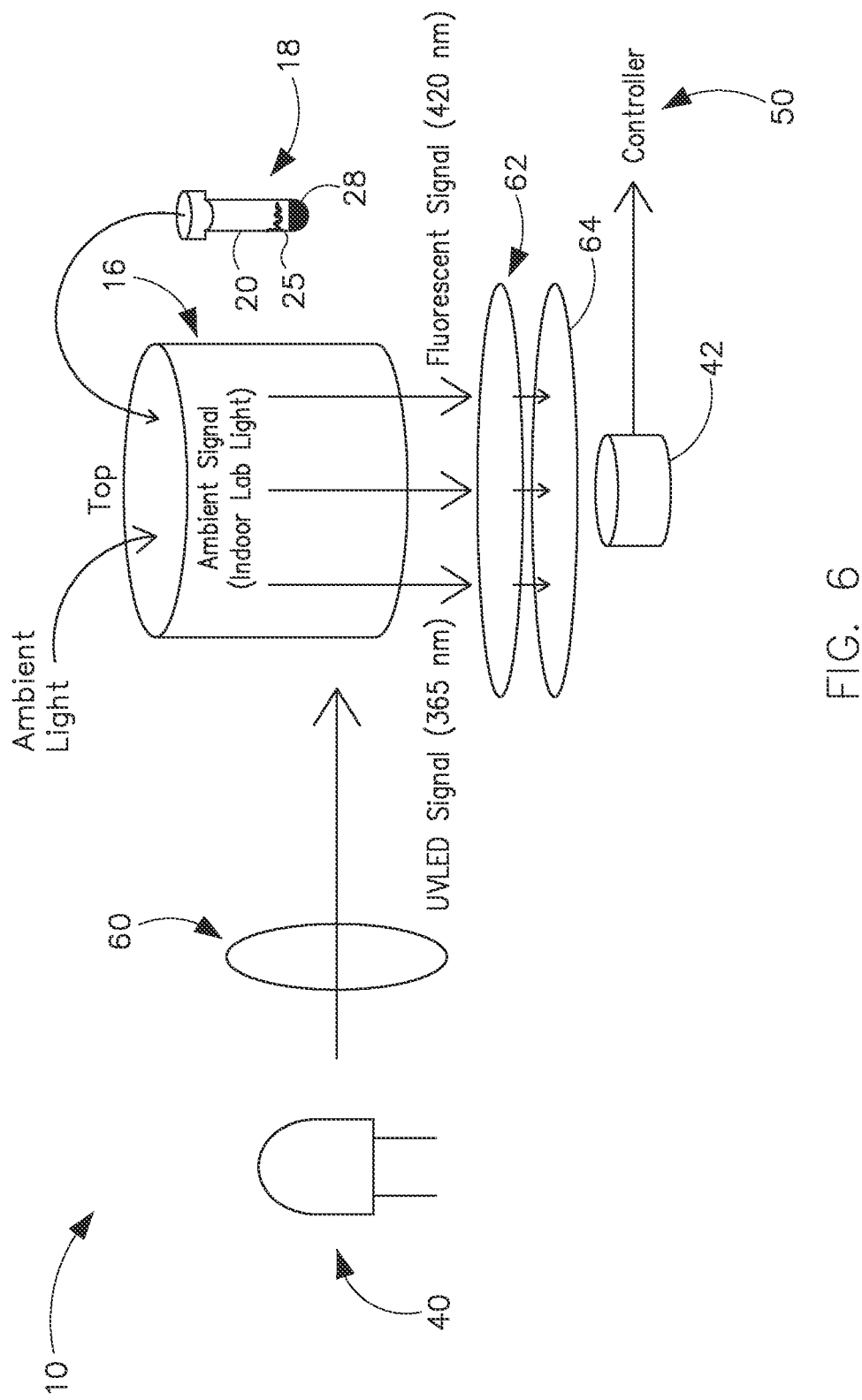

FIG. 6 is a schematic of one embodiment of a biological indicator holder or well of a biological indicator reader.

Figure 7:
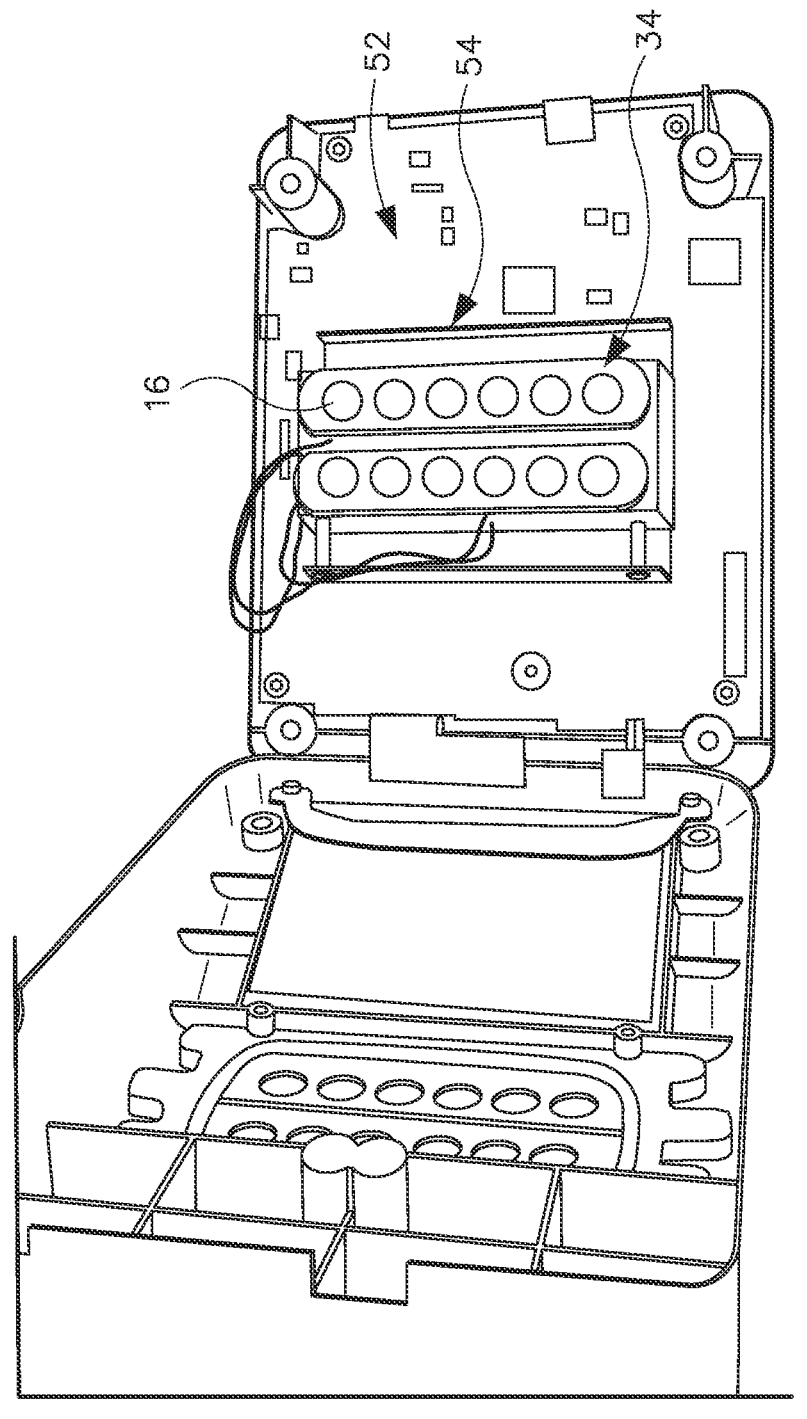

FIG. 7 is a perspective top view of a biological indicator reader.

Figure 8:
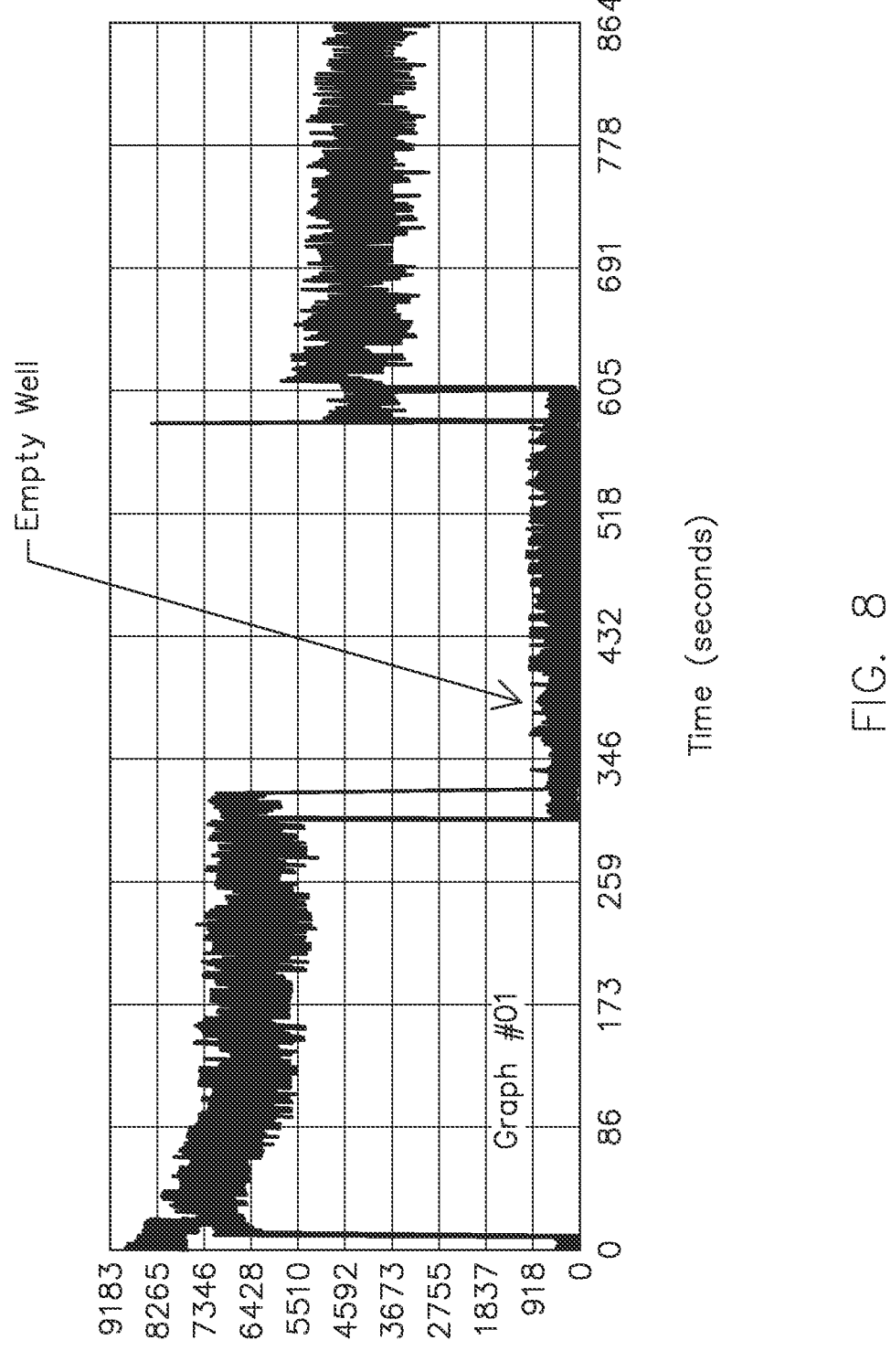

FIG. 8 is fluorescent data taken with the UV LED emitter on.

Figure 9:
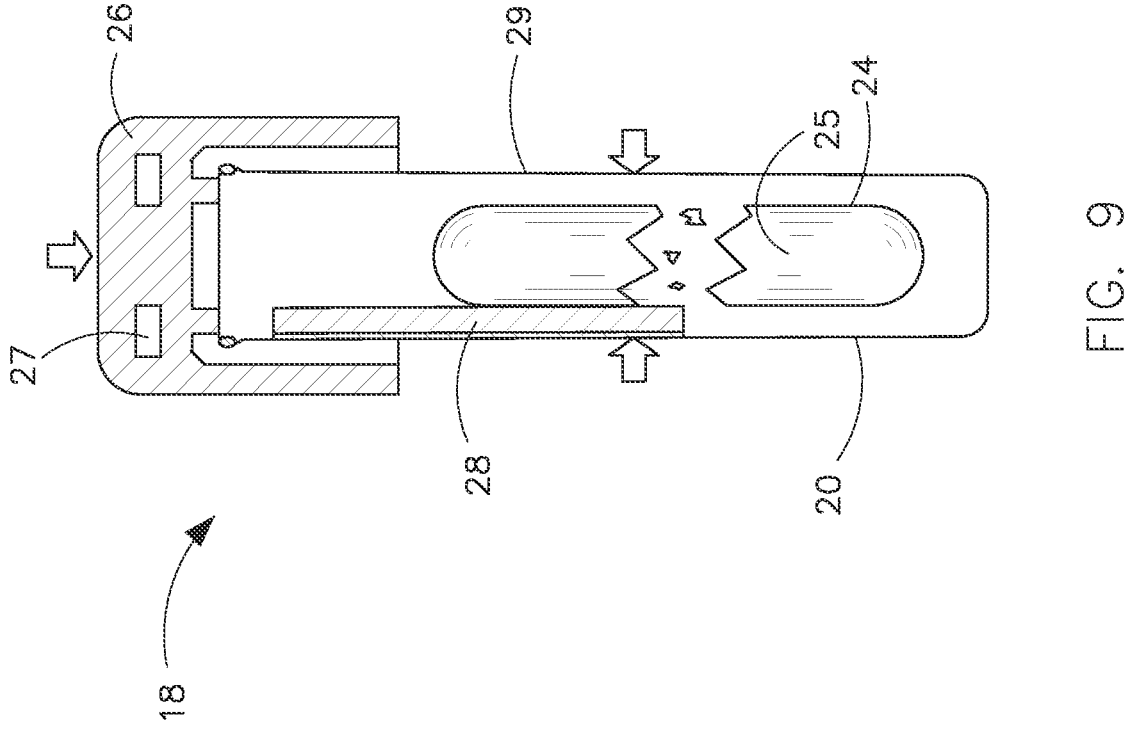

FIG. 9 is a is a front view of one embodiment of the components of the biological indicator.

Figure 10:
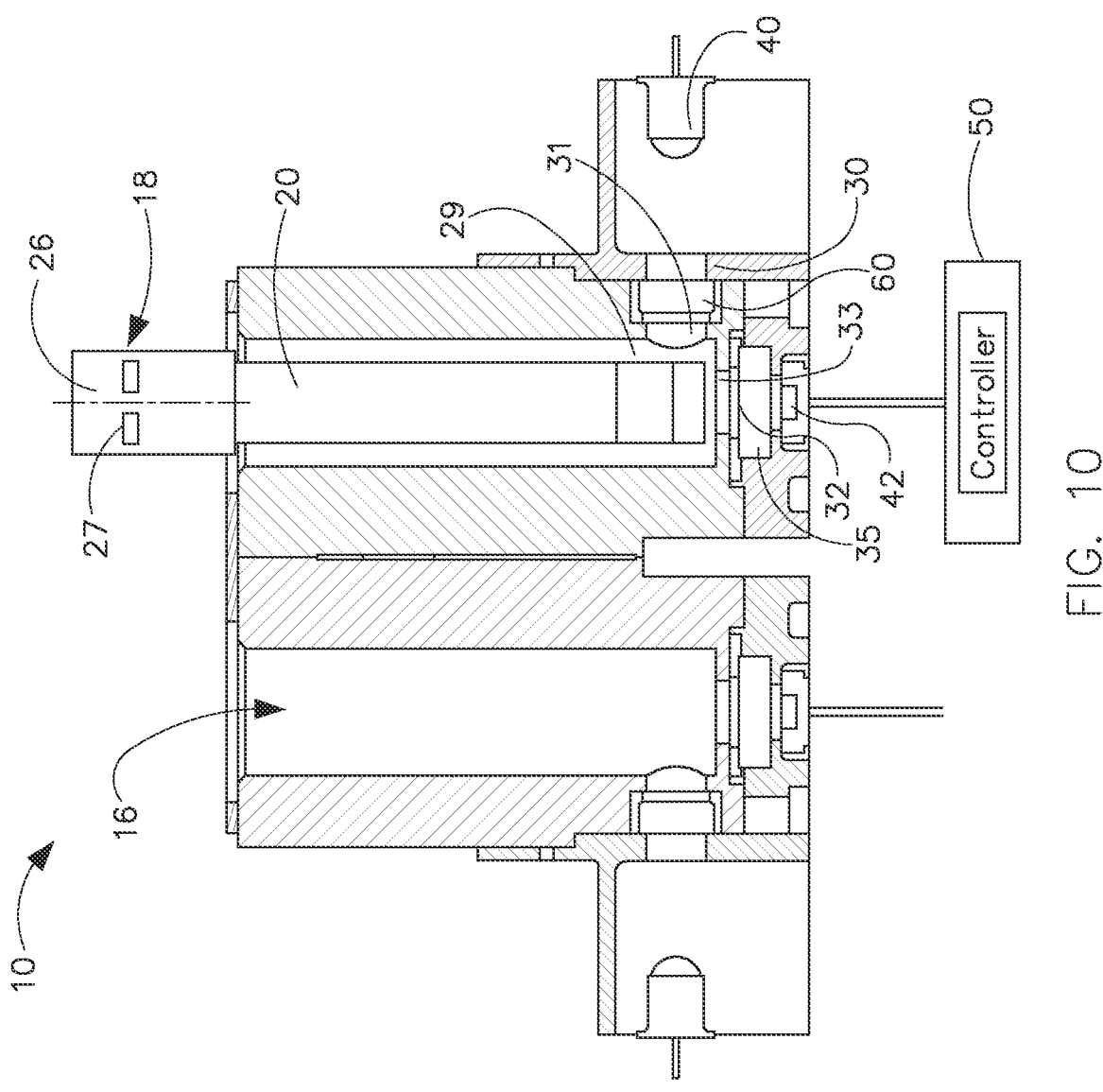

FIG. 10 is a partial cross-sectional side view of a biological indicator system according to an embodiment of the present disclosure, the biological sterilization indicator system including a biological sterilization indicator shown in a perspective view.

Figure 11:
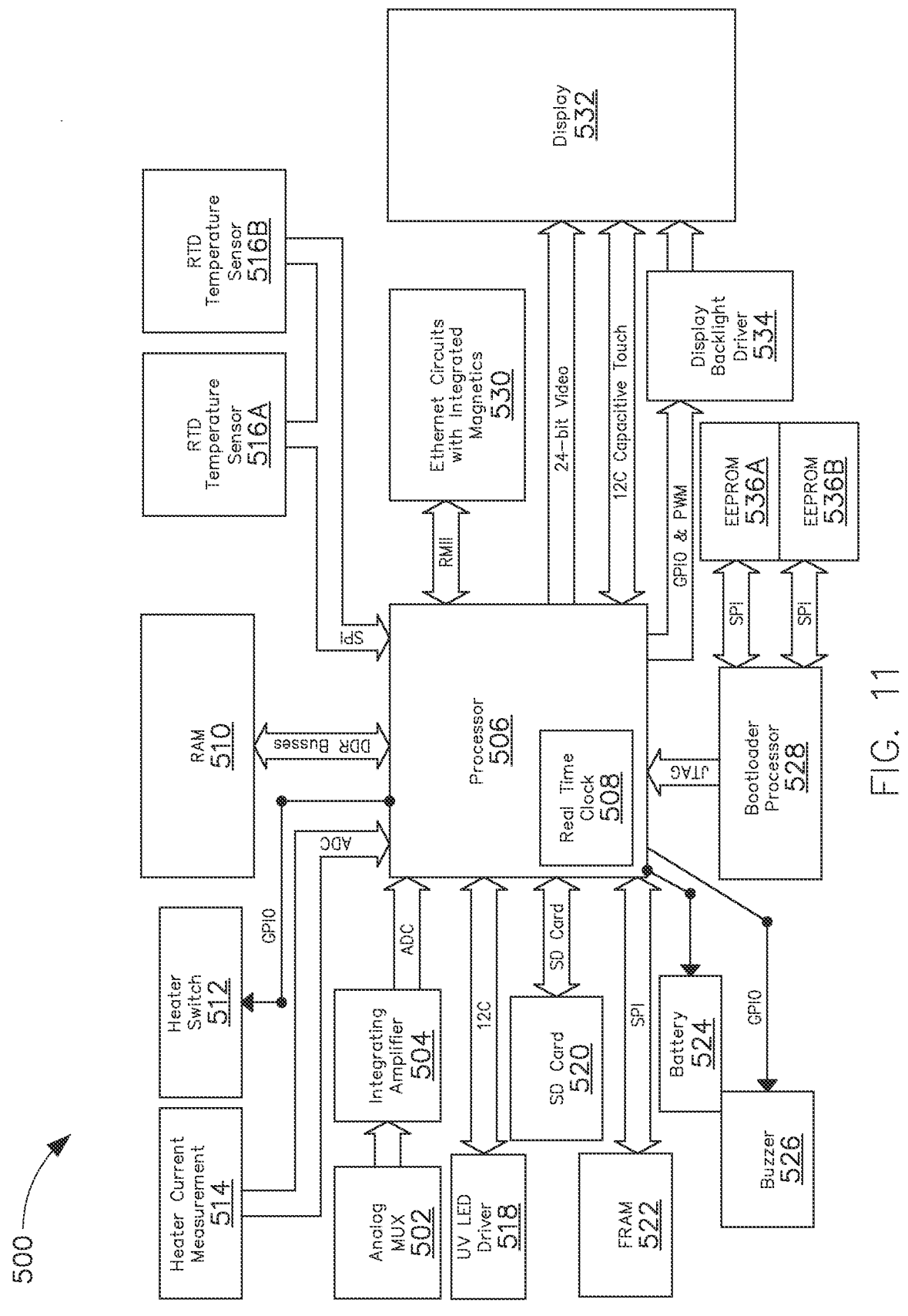

FIG. 11 is an embodiment of the electronic controller system and its associated components.

Figures 12, 13:
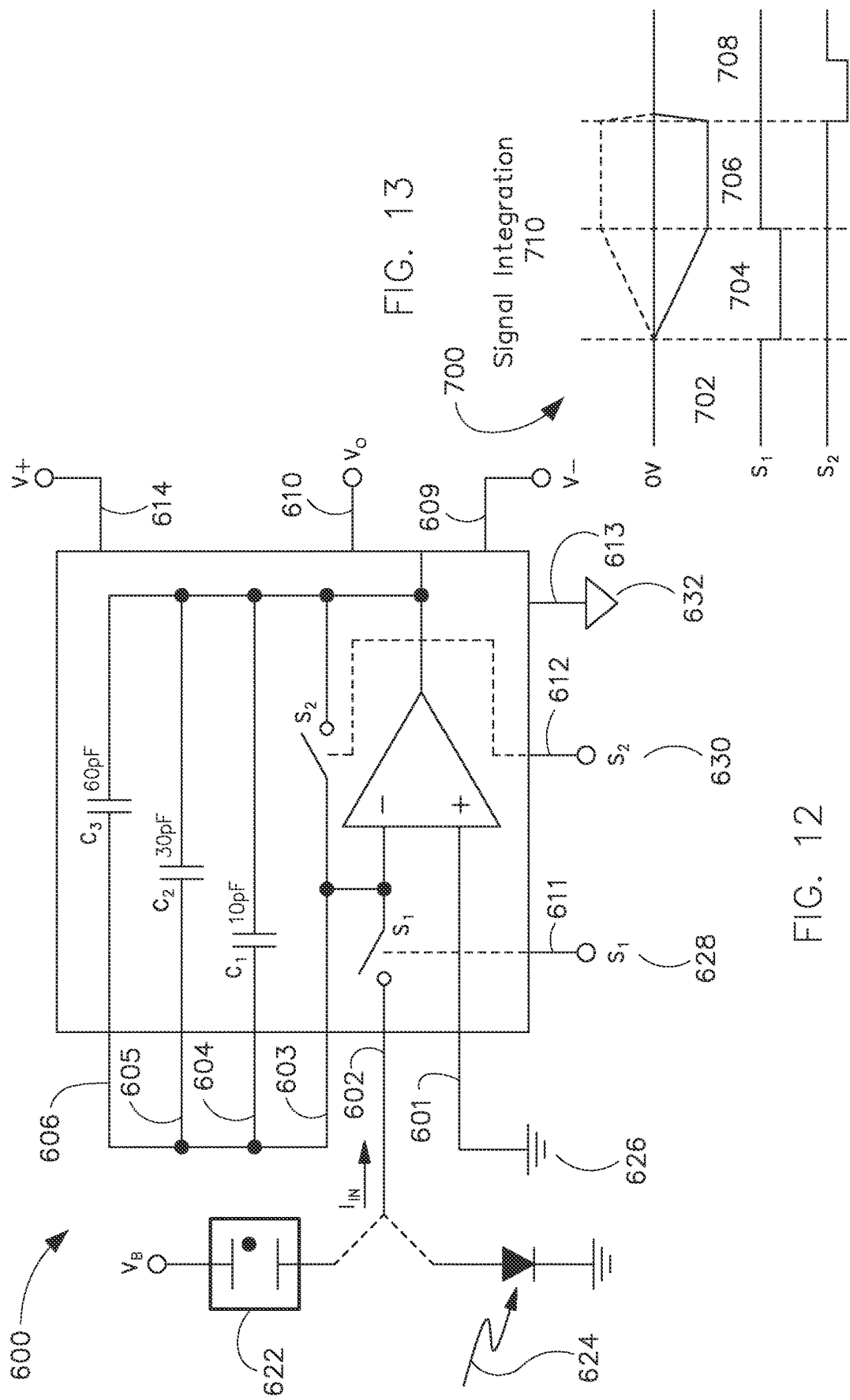

FIG. 12 shows an exemplary integrated amplifier circuit associated with the electronic controller system.

FIG. 13 shows an exemplary signal integration of an integrated amplifier circuit.

Figure 14:
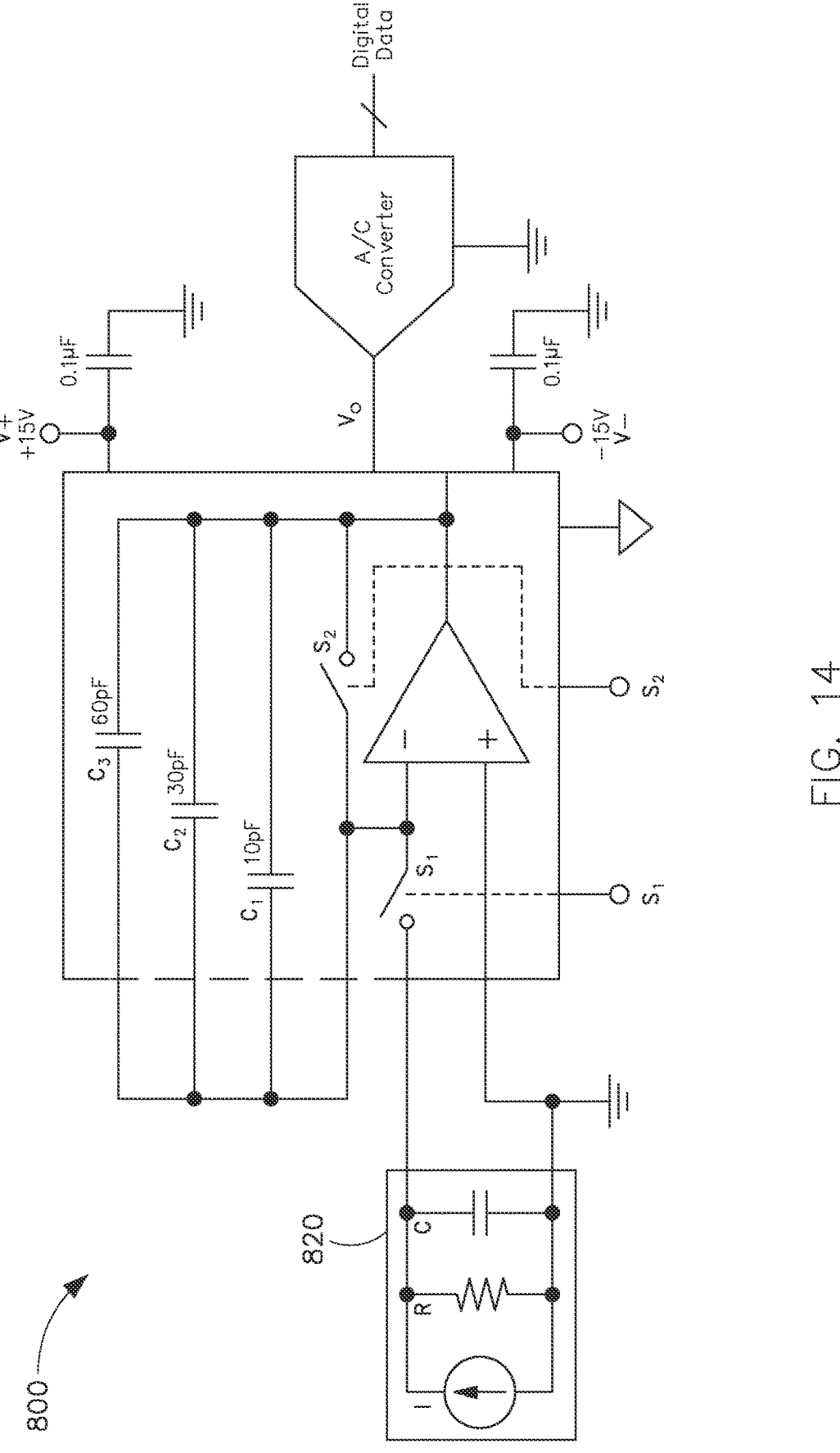

FIG. 14 shows another exemplary integrated amplifier circuit associated with the electronic controller system.

Figure 15:
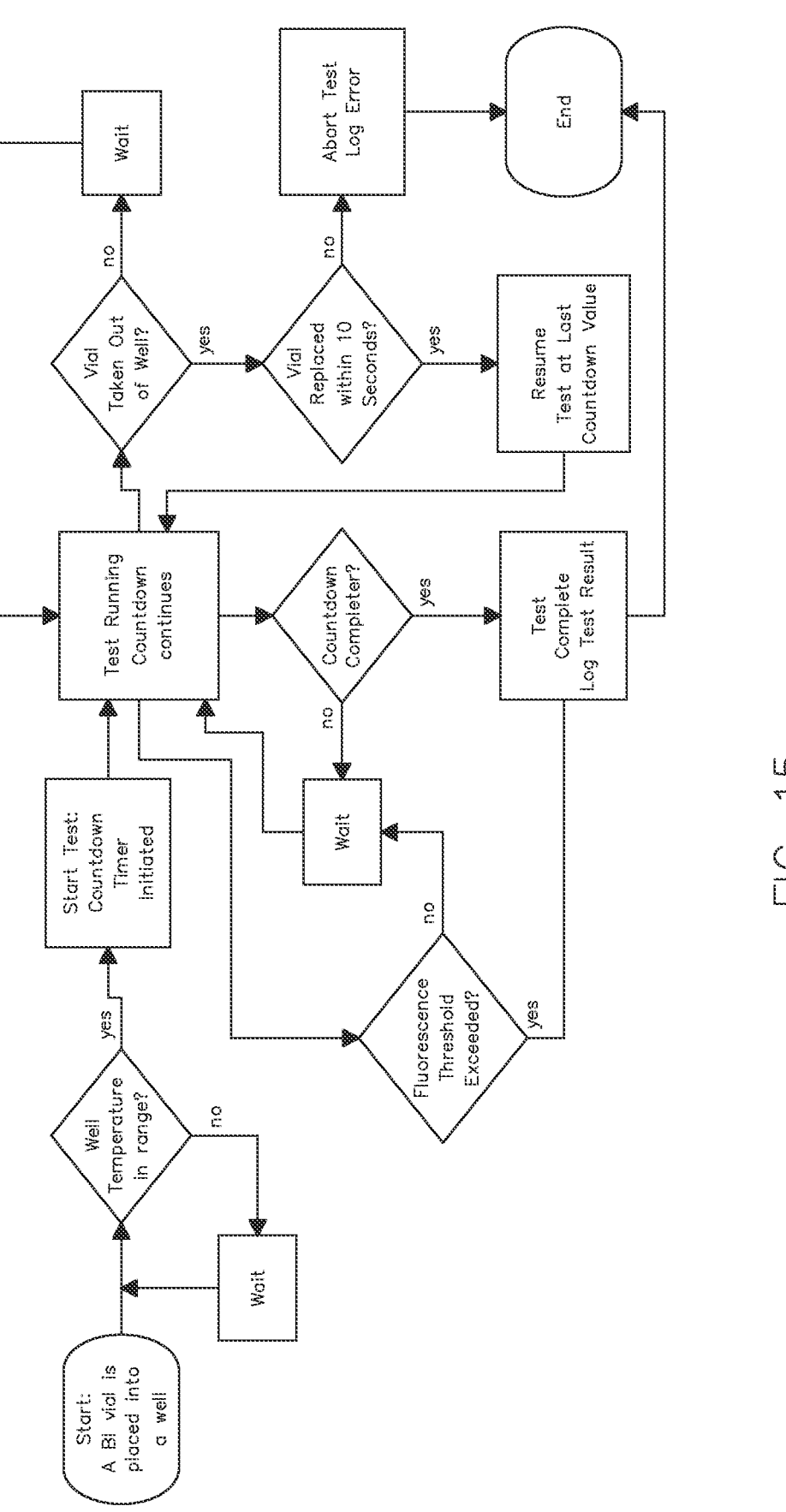

FIG. 15 shows an exemplary embodiment of the logic steps that the controller performs for a well test.

Figure 16:
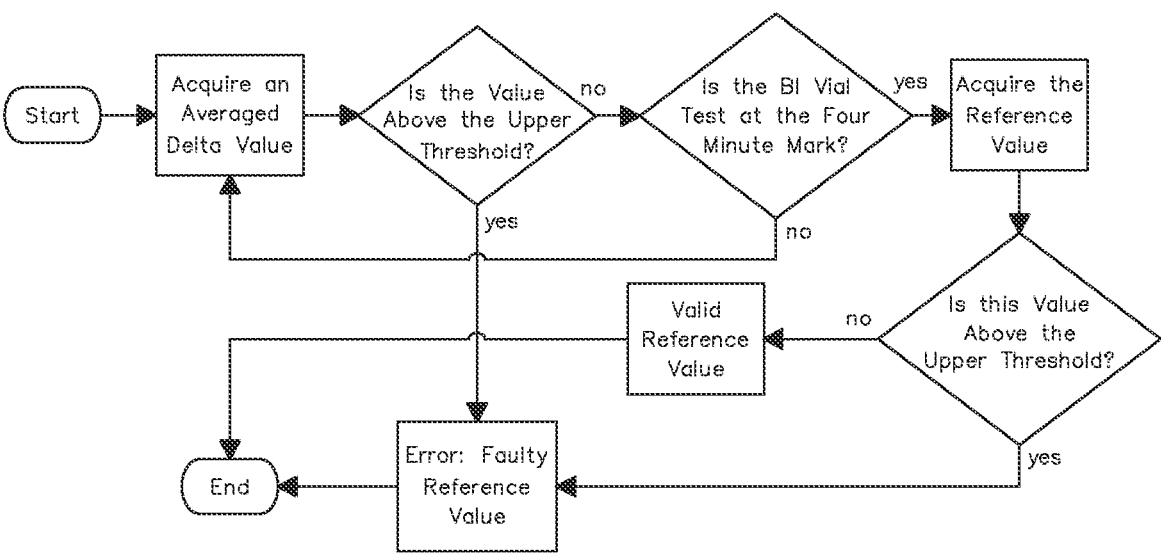

FIG. 16 shows an exemplary embodiment of the logic steps that the controller performs for a biological indicator vial test.

Figure 17:
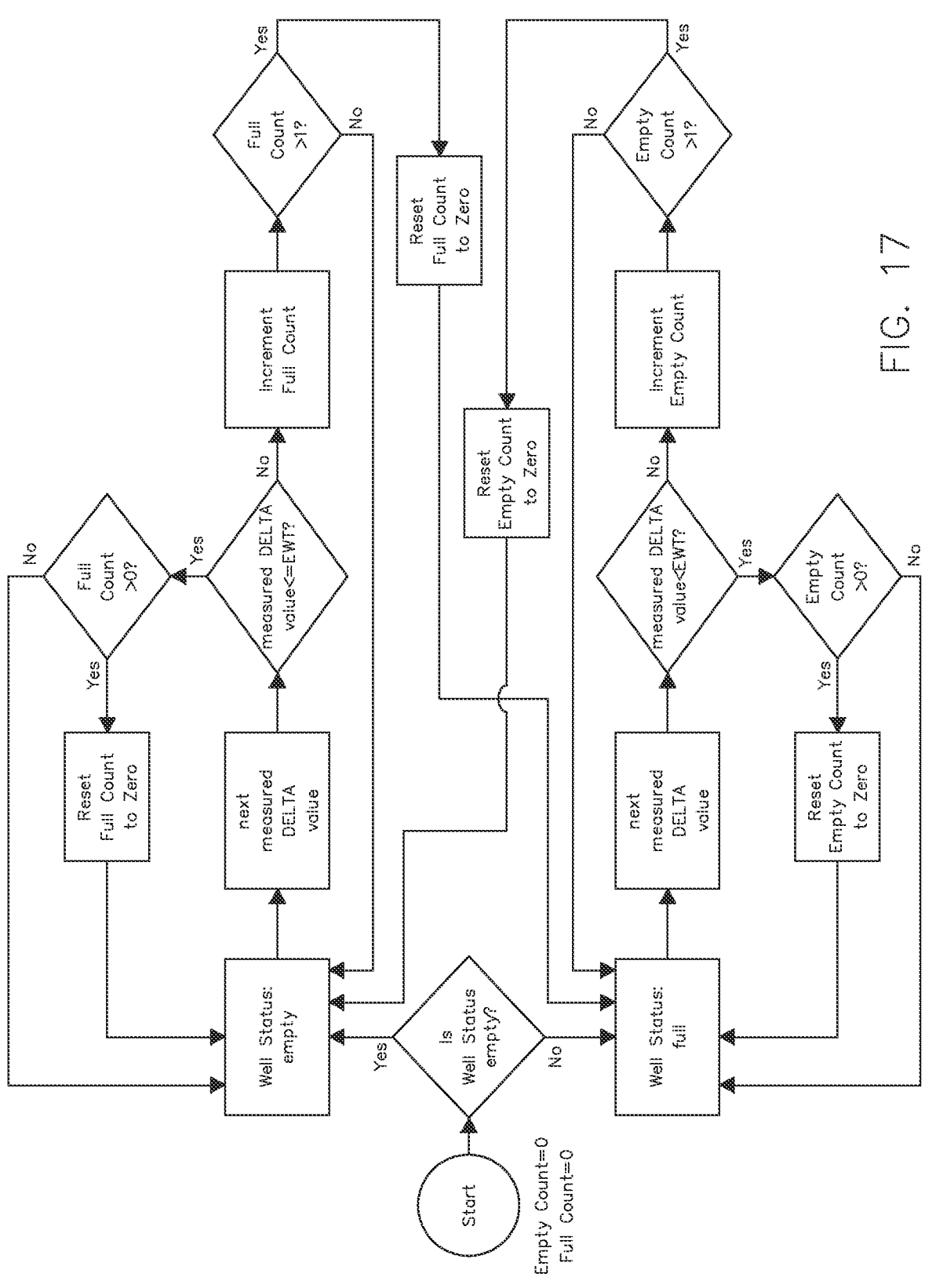

FIG. 17 shows another exemplary embodiment of the logic steps that the controller performs for a biological indicator vial test.

Figure 18:
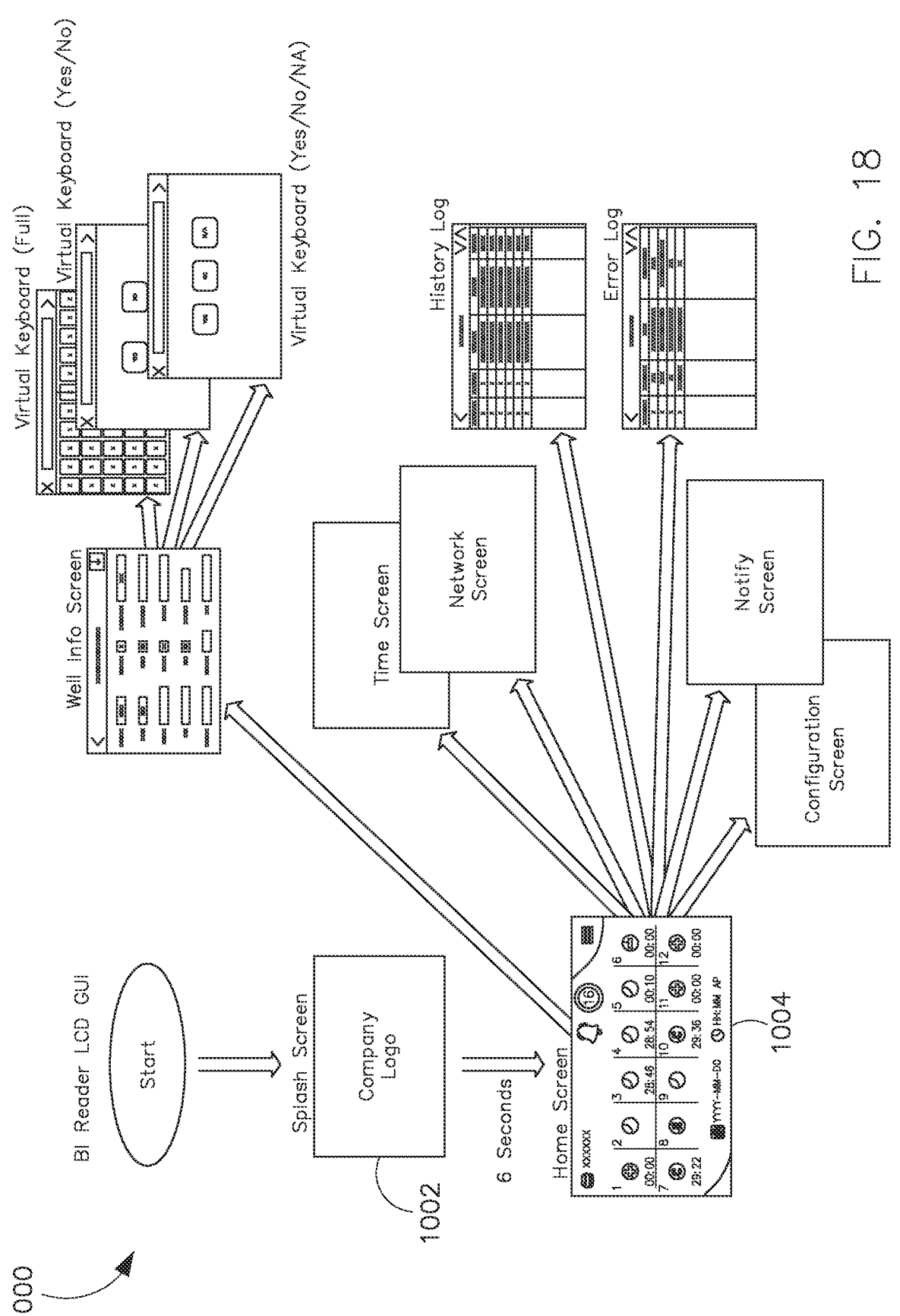

FIG. 18 illustrates various display screens and their sequence that are liquid crystal display touch screens of the graphical user interface of the biological indicator reader.

Figure 19:

FIG. 19 illustrates an exemplary embodiment of the home screen.

Figure 20:
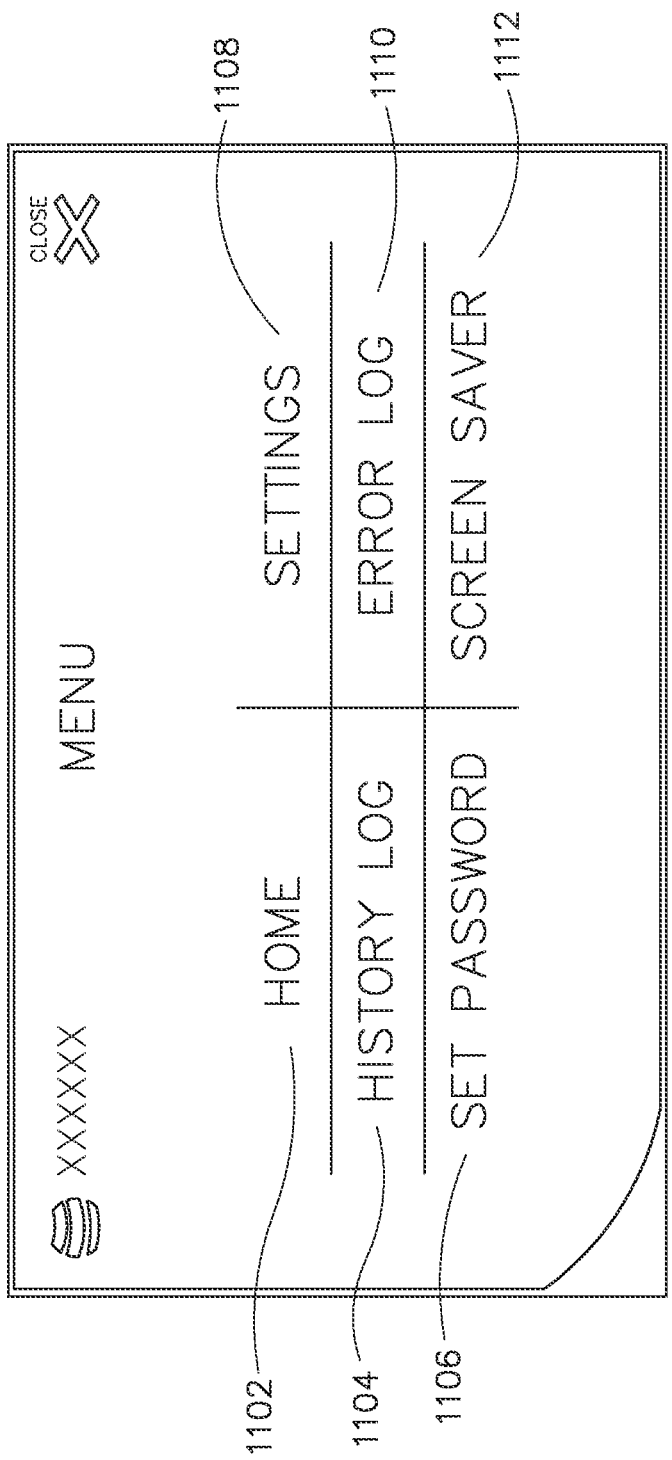

FIG. 20 illustrates an exemplary embodiment of the screen when the menu icon is pressed.

FIG. 21A illustrates an exemplary embodiment of the user input textboxes.

FIG. 21B illustrates another exemplary embodiment of the textbox.

Figure 22:
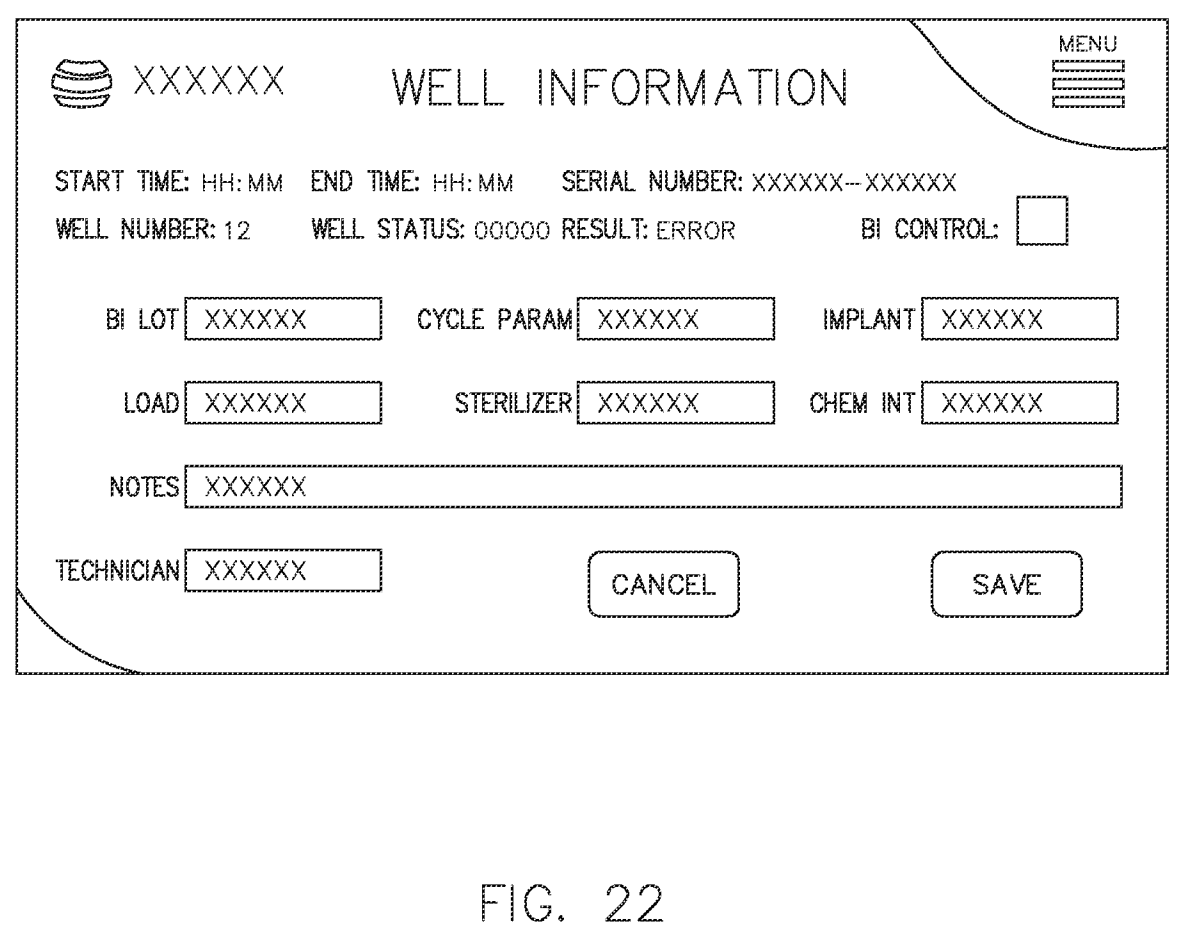

FIG. 22 illustrates an exemplary embodiment of a well information screen concerning well information.

Figure 23:
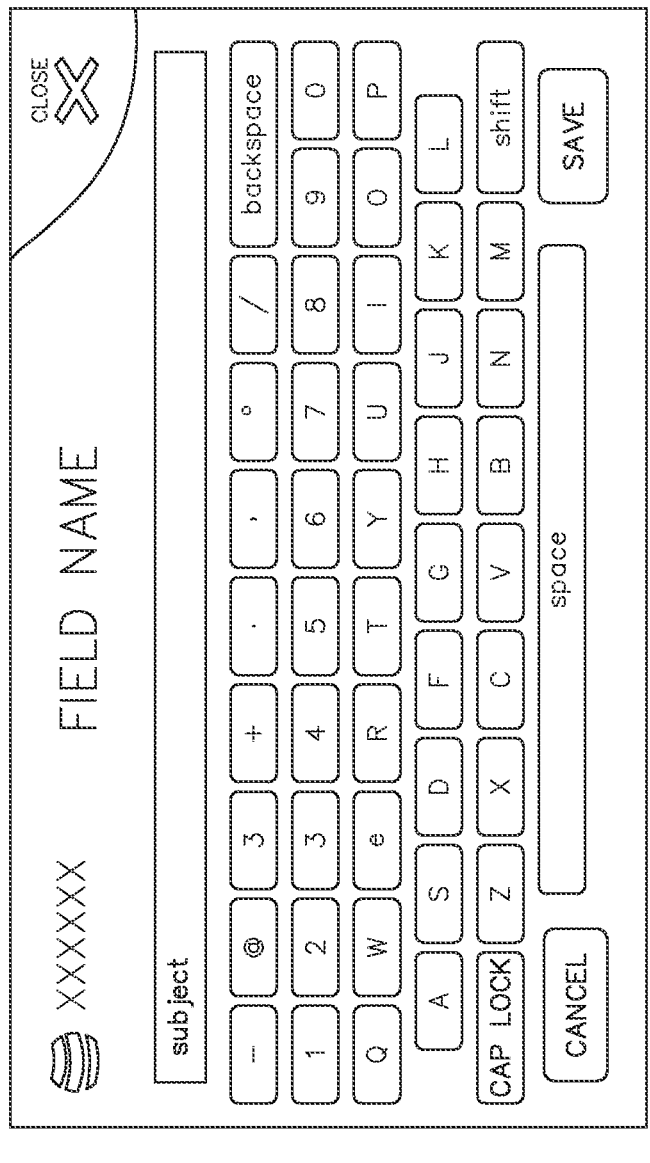

FIG. 23 illustrates an exemplary embodiment of a virtual touch screen keyboard.

Figure 24:
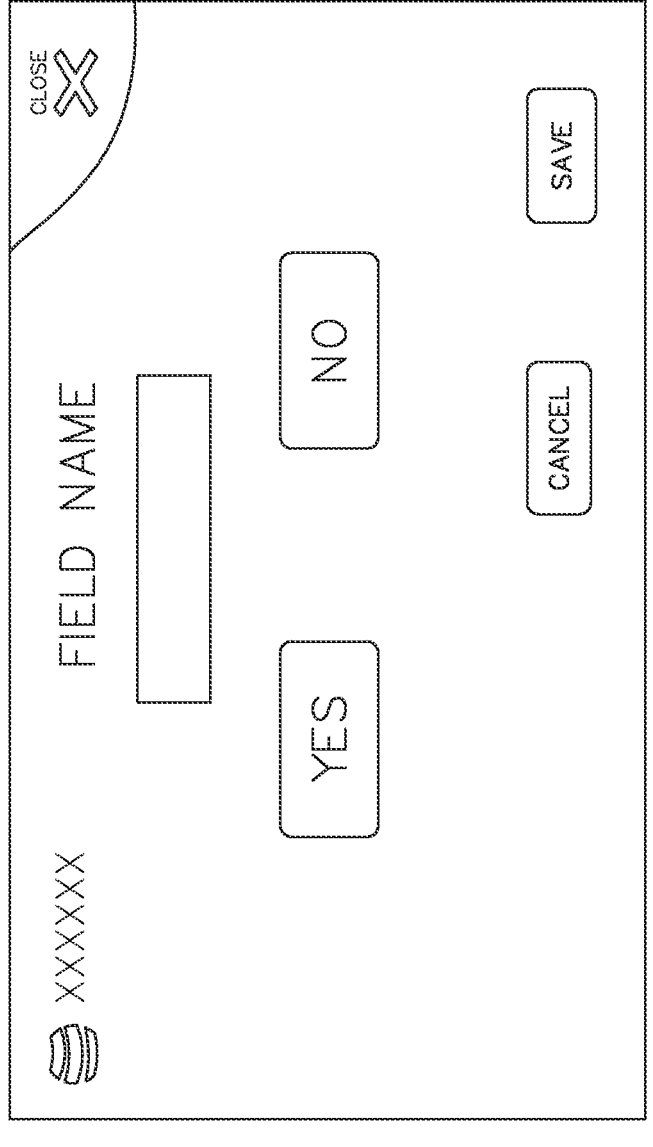

FIG. 24 illustrates another exemplary embodiment of the textbox for a control parameter.

Figure 25:
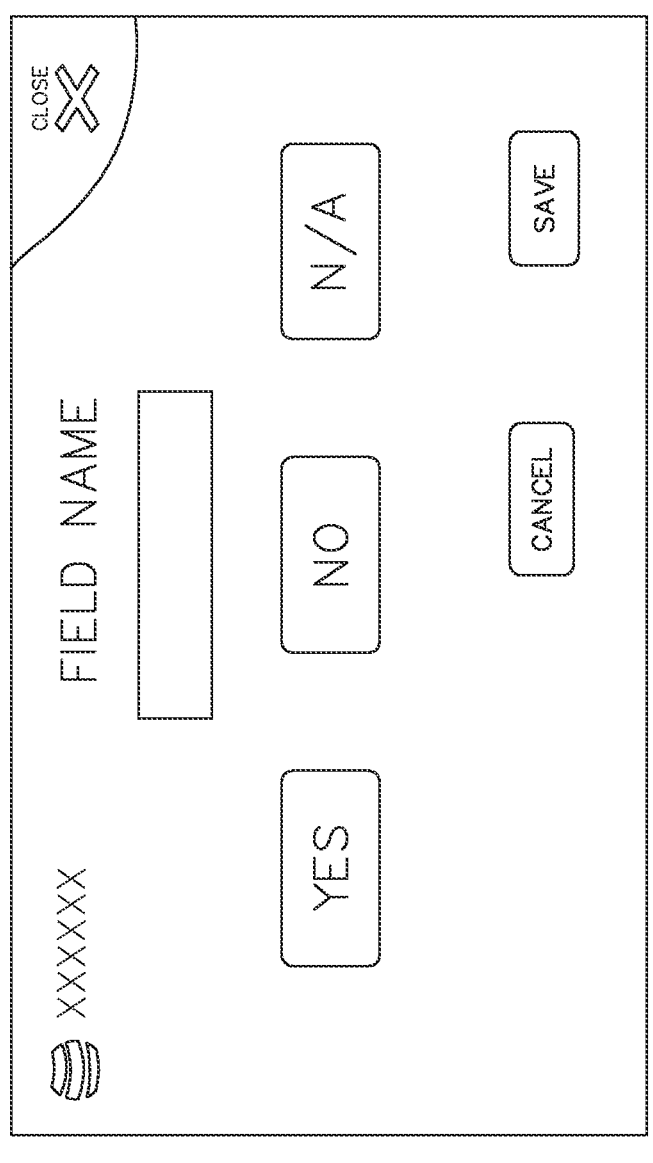

FIG. 25 illustrates another exemplary embodiment of the textbox.

Figure 26:
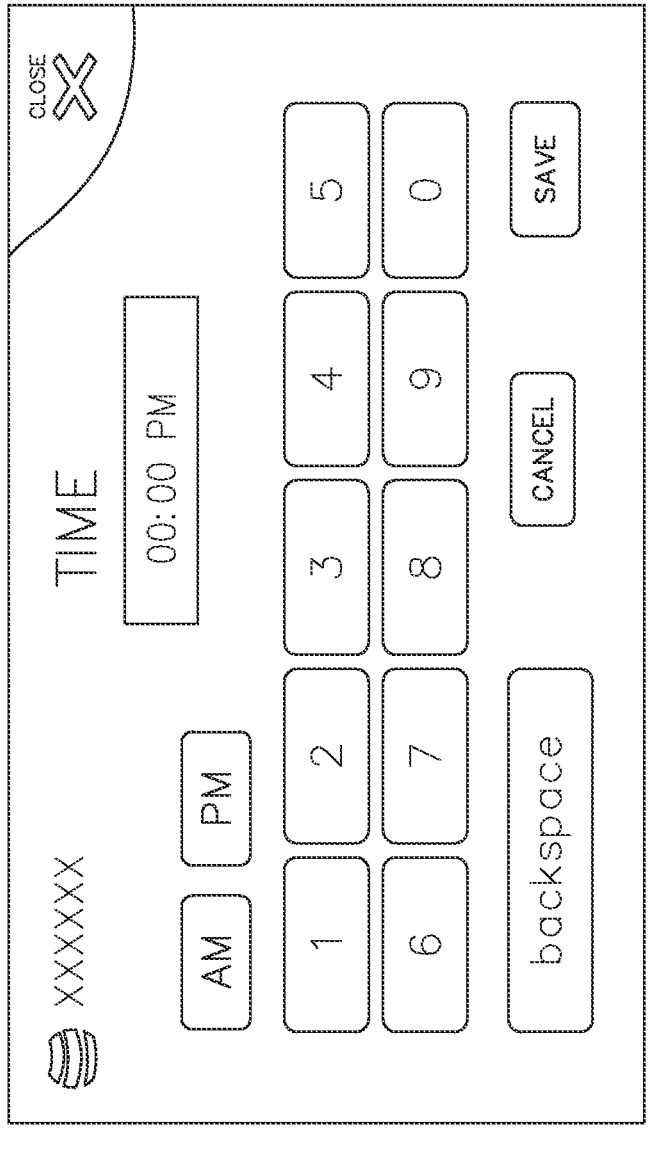

FIG. 26 illustrates another exemplary embodiment of a virtual keyboard to enter in the time.

Figure 27:
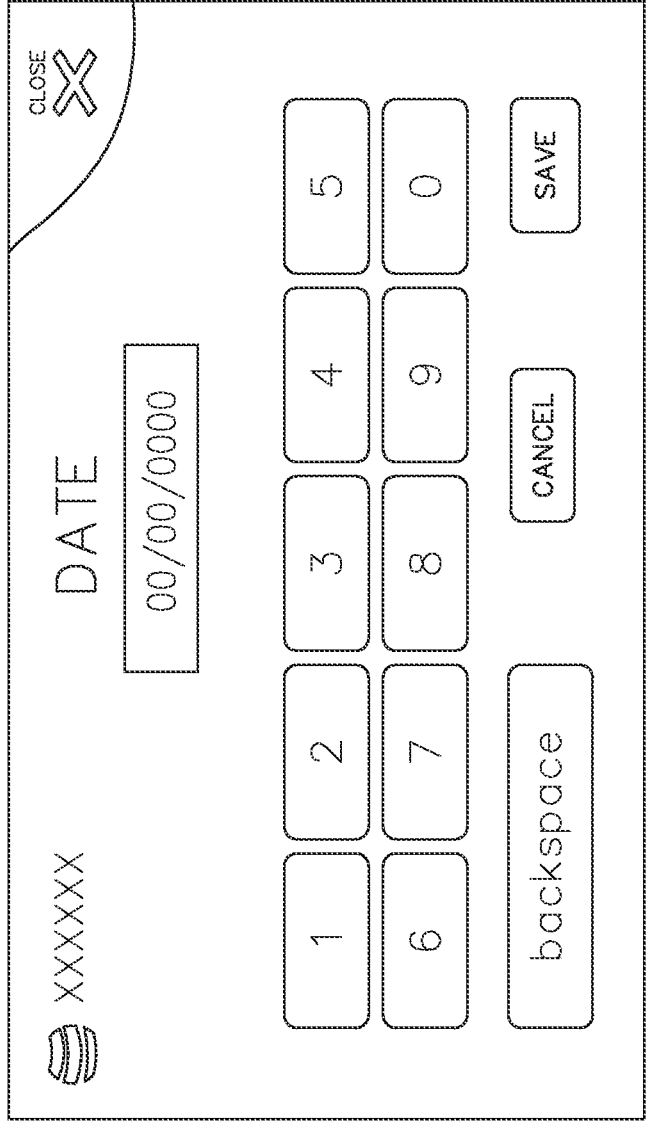

FIG. 27 illustrates another exemplary embodiment of a virtual keyboard.

Figure 28:
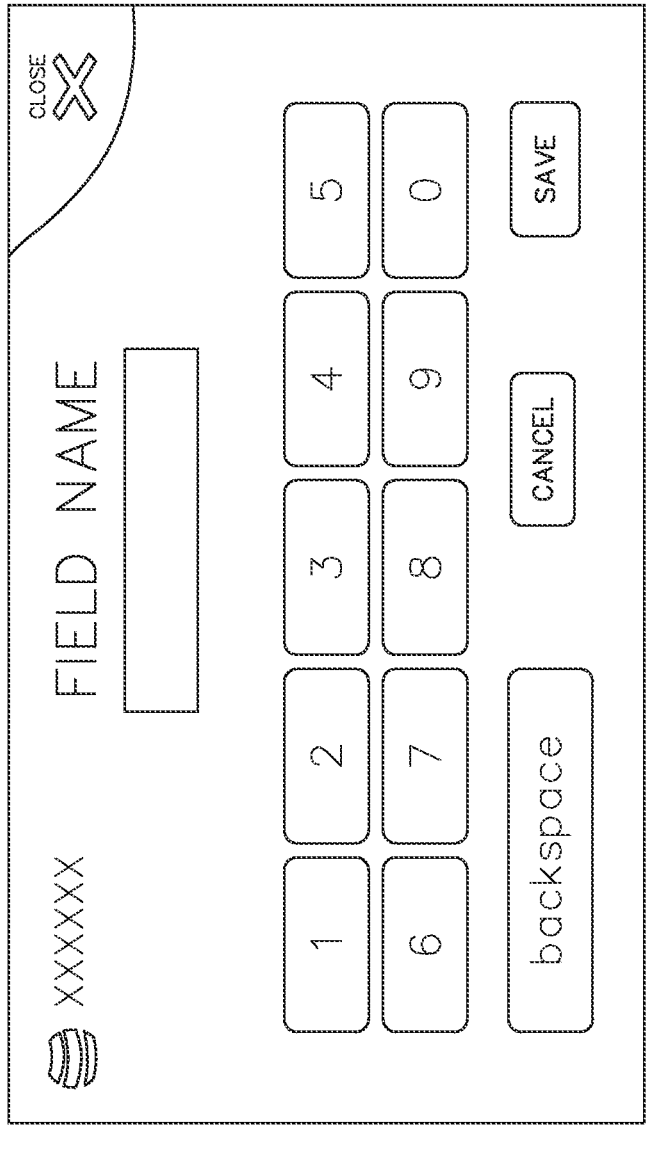

FIG. 28 illustrates another exemplary embodiment of a virtual keyboard to enter numeric information.

Figure 29:
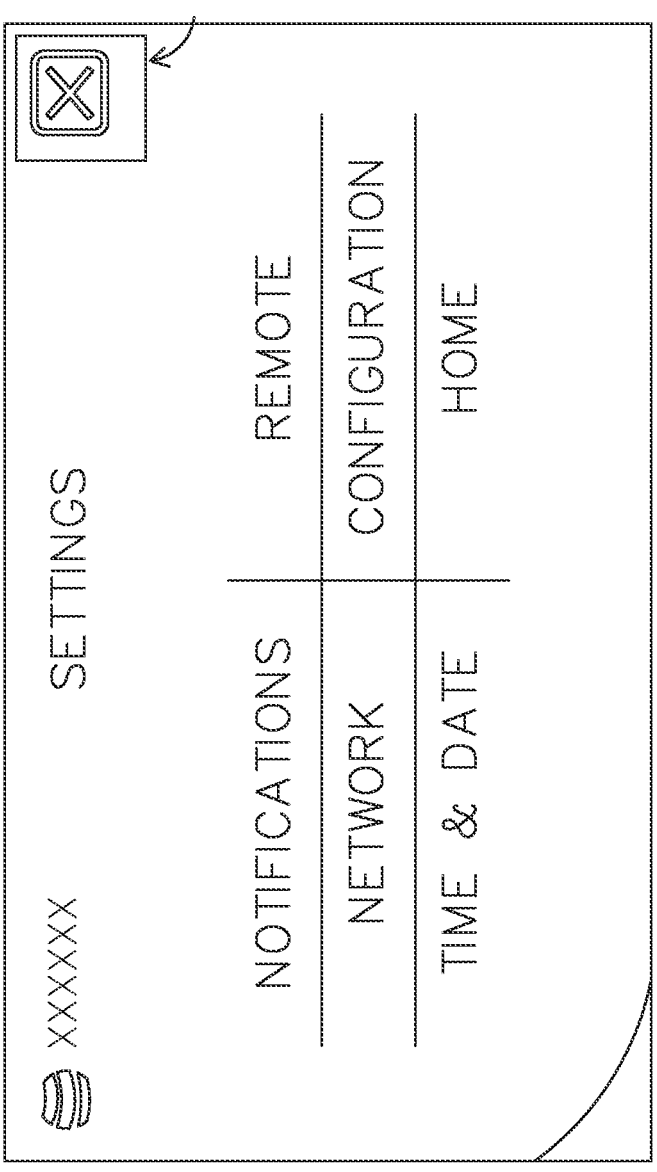

FIG. 29 illustrates an exemplary embodiment of a navigation bar.

7

8

FIG. 30 illustrates an embodiment of a history screen to record results of the vial for the biological indicator.

Figure 31:
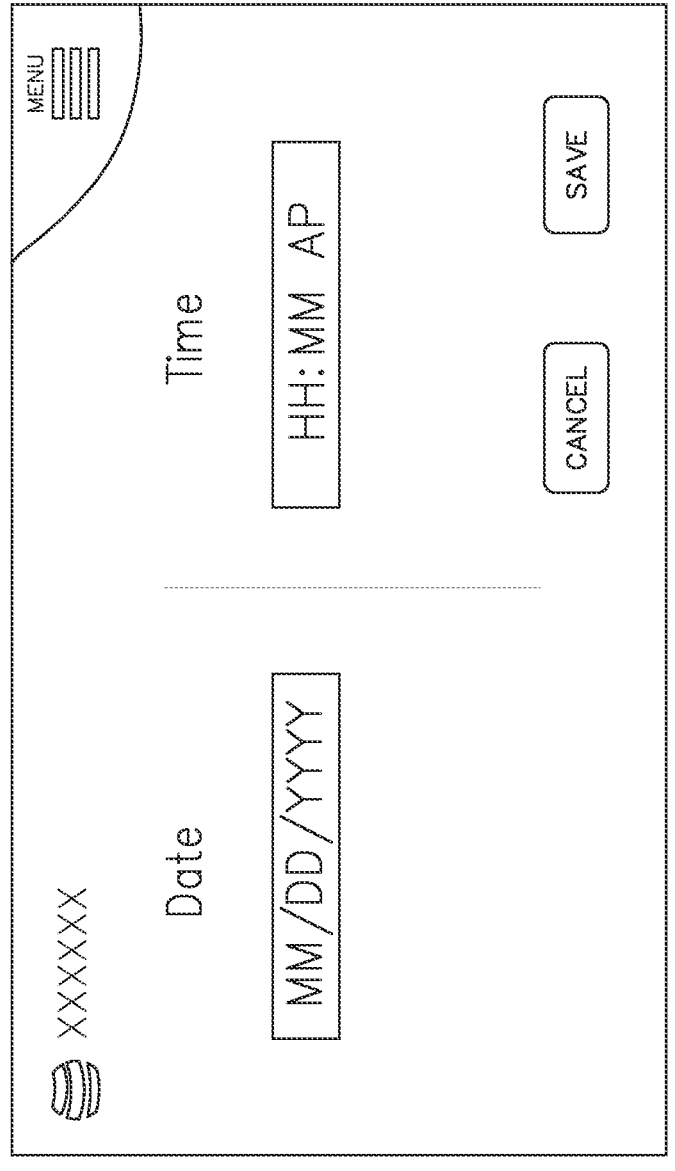

FIG. 31 illustrates an embodiment of a screen to enter time and date.

Figure 32:
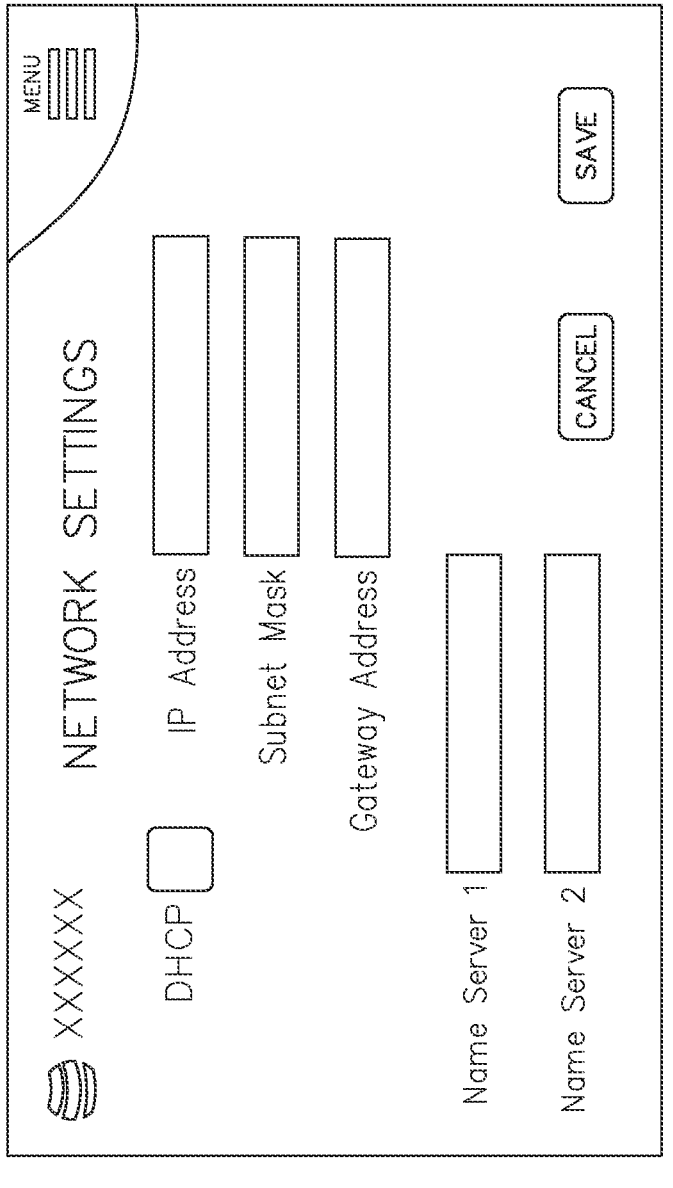

FIG. 32 illustrates an embodiment of a screen to enter in network setting.

Figure 33:
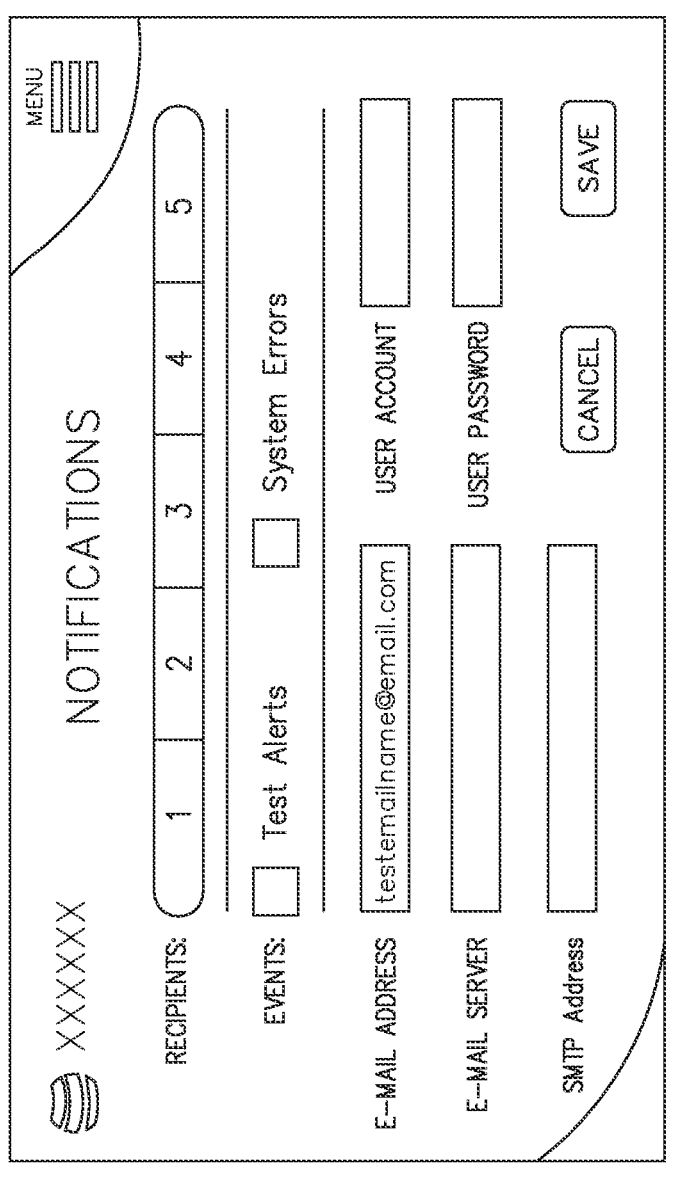

FIG. 33 illustrates an embodiment of a notify screen, where data can be entered for a user to be notified of a positive results or a system error.

FIG. 34 illustrates an embodiment of error log screen.

Figure 35:
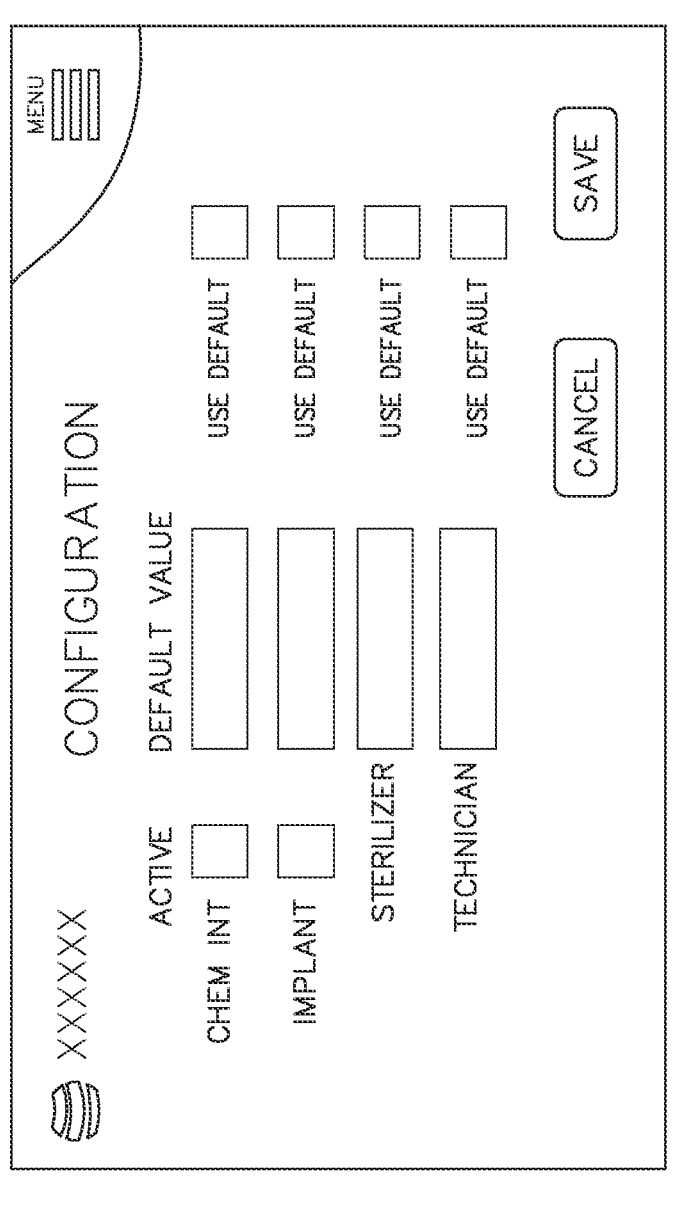

FIG. 35 illustrates an embodiment of a configuration screen.

Figure 36:
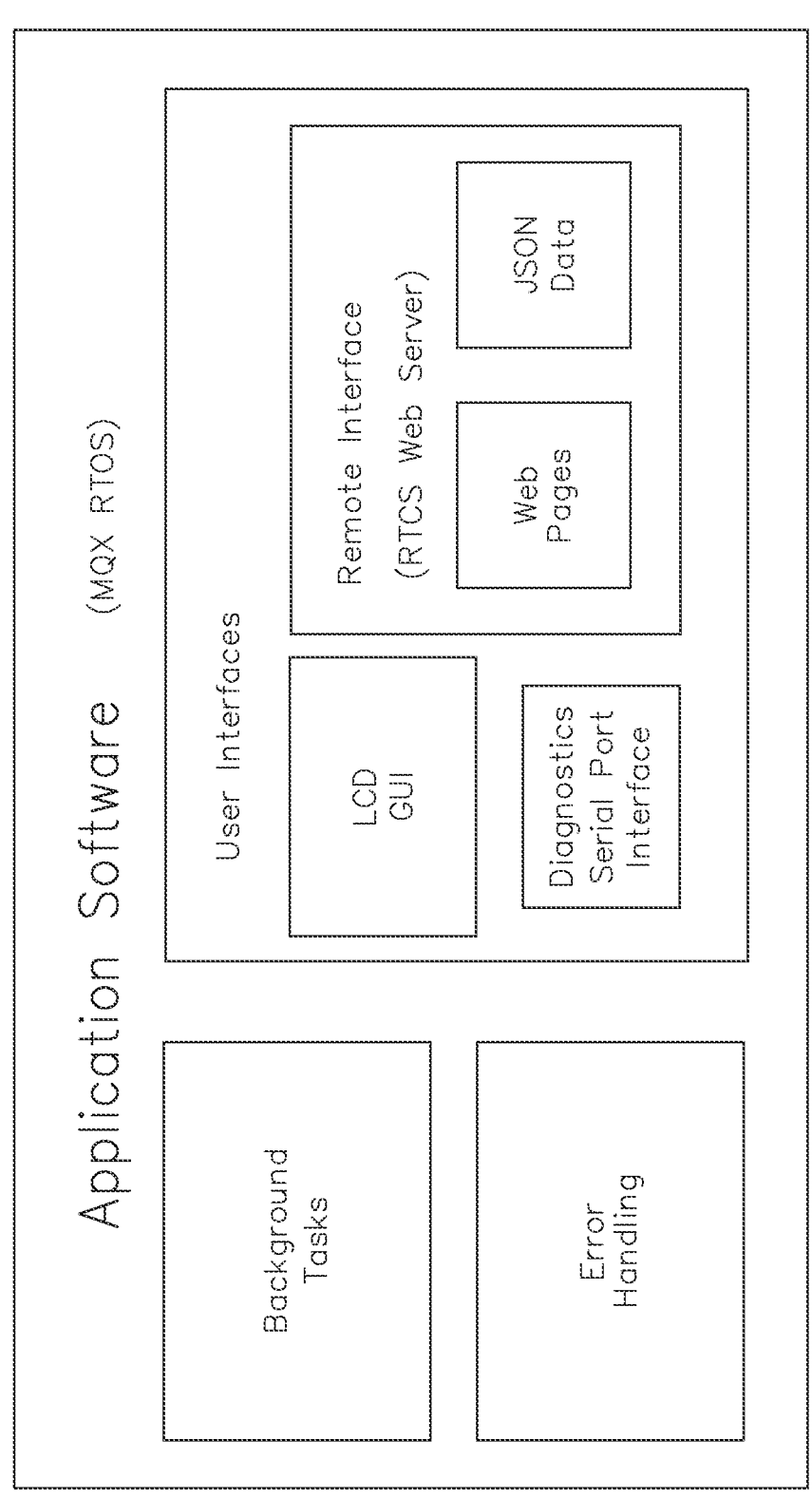

FIG. 36 illustrates an embodiment of reader's software components.

Figure 37:
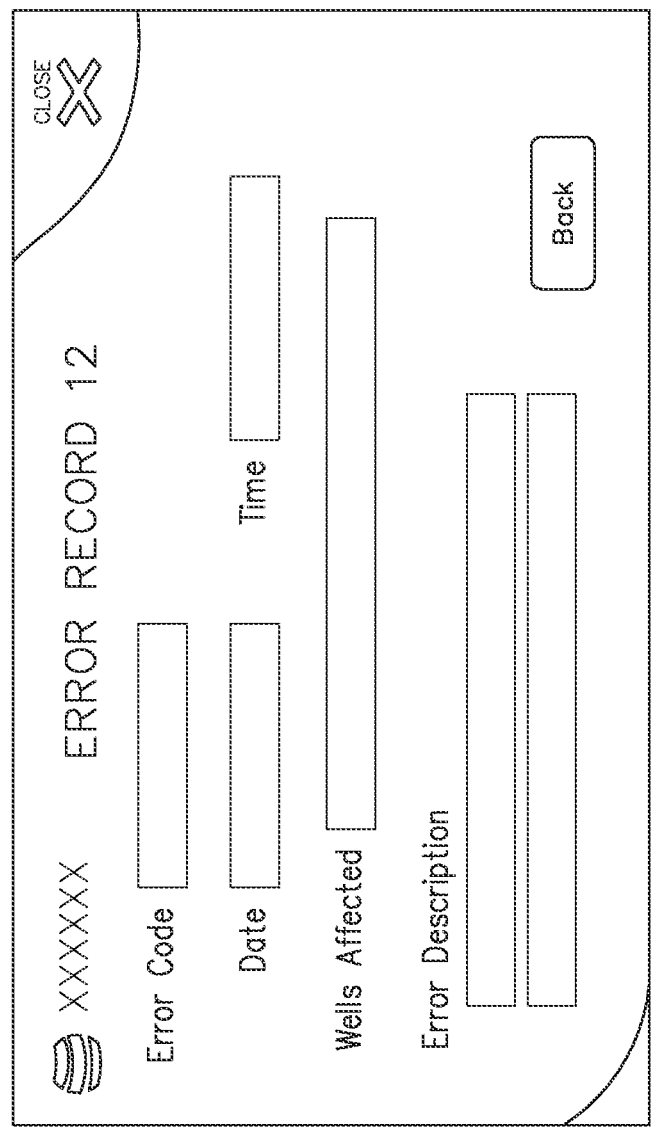

FIG. 37 illustrates an embodiment of an error record screen.

Figure 38:
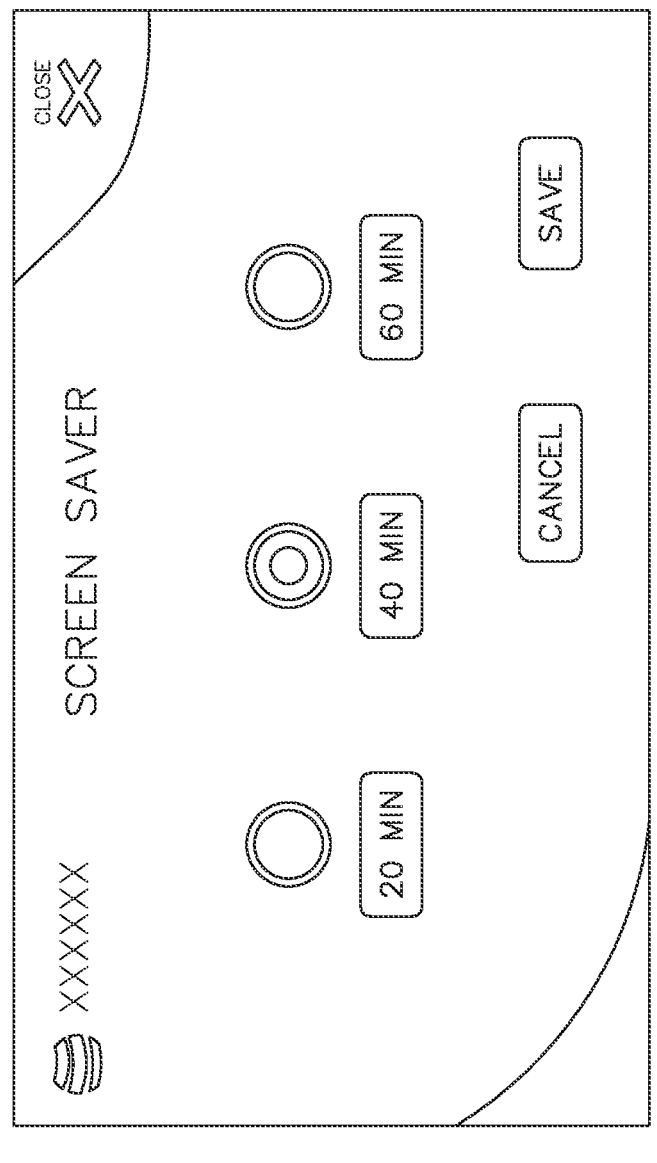

FIG. 38 illustrates an embodiment of a screen saver screen.

Figure 39:
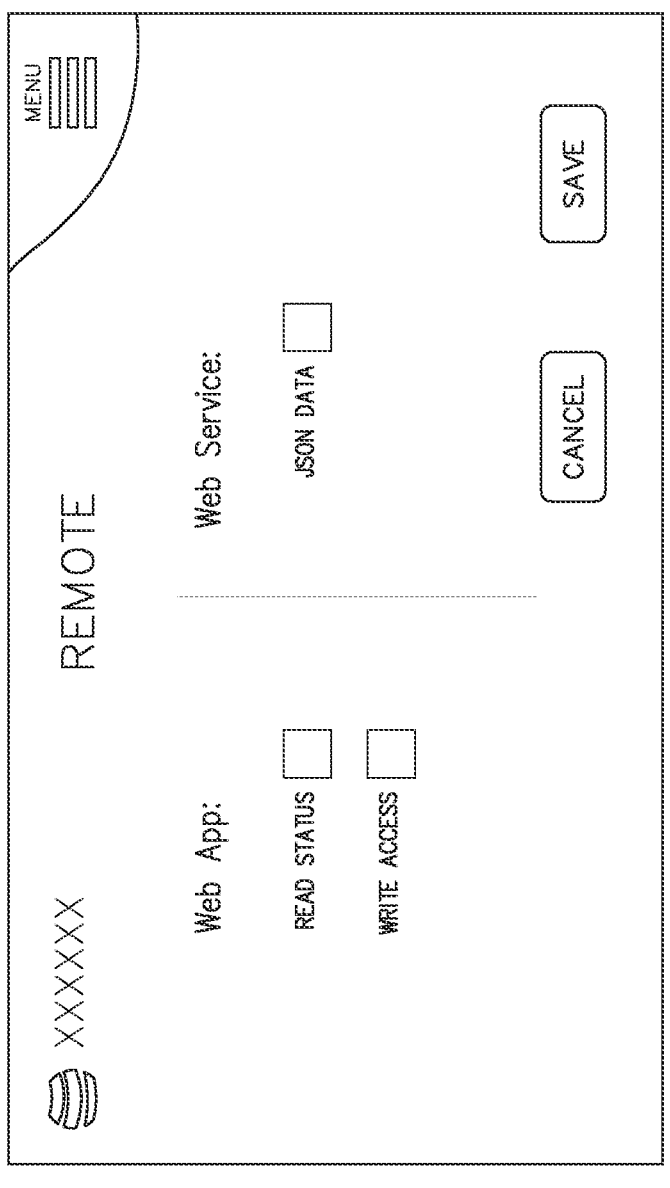

FIG. 39 illustrates an embodiment of a remote screen.

Figure 40:
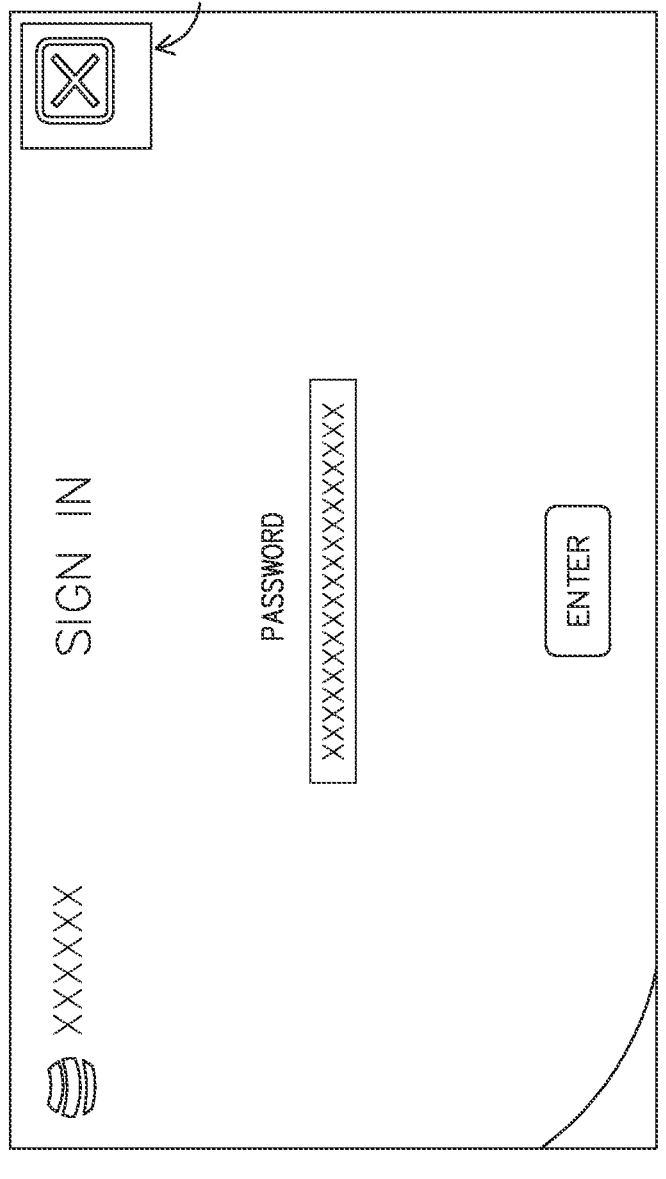

FIG. 40 illustrates an embodiment of a password screen.

Figure 41:
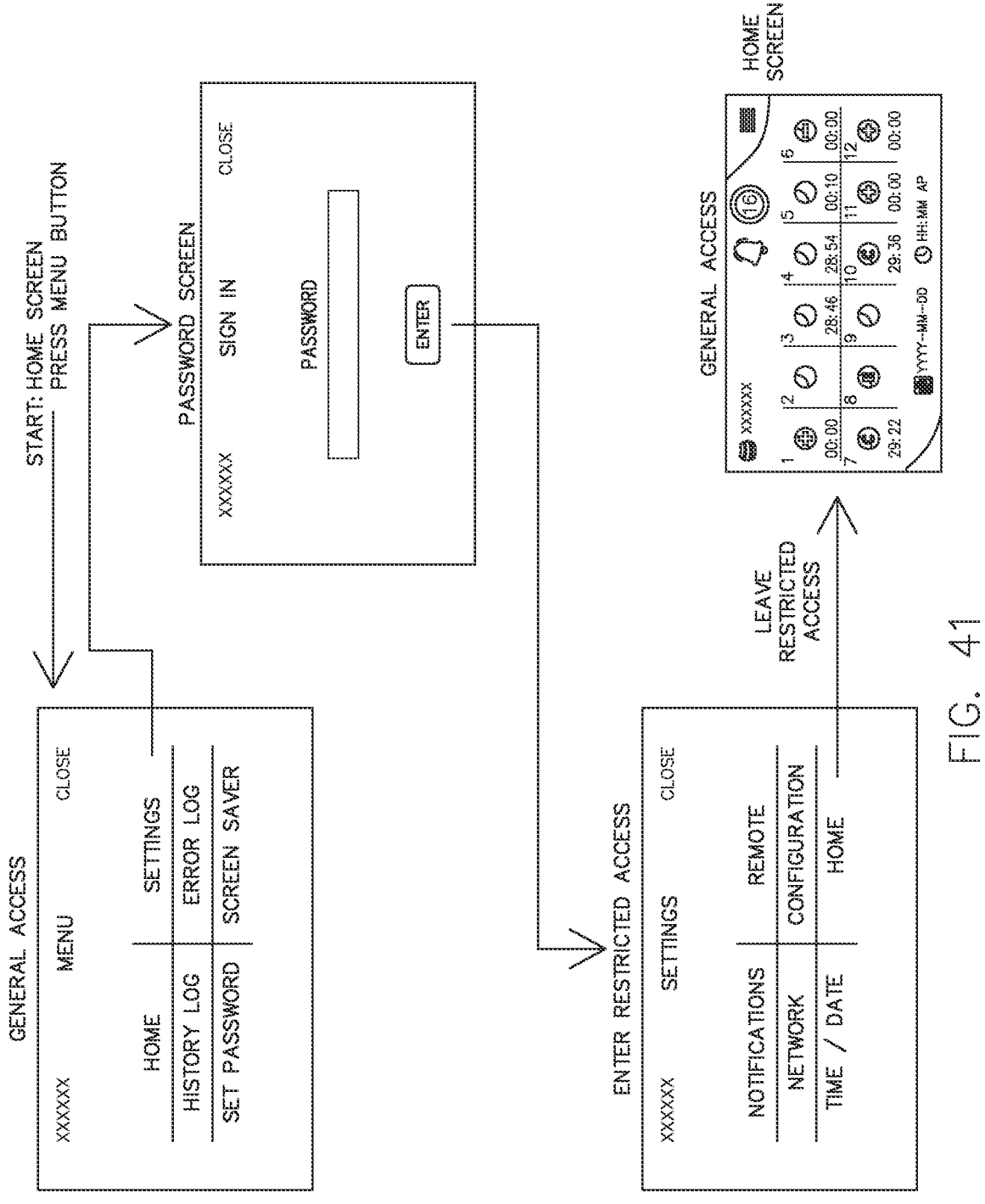

FIG. 41 illustrates an embodiment of navigation between general access screens and restricted access screens.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a vial" includes one, two, three or more vials.

Definitions

The term "sterilization" includes, but is not limited to, rendering a substance incapable of reproduction, metabolism and/or growth. While this is often taken to mean total absence of living organisms, the term may also be used to refer to a substance free from living organisms to a degree previously agreed to be acceptable. Unless otherwise indicated, the term sterilization may also include methods and procedures less rigorous than sterilization, for example, disinfection, sanitization, or the like. The sterilization indicator or biological indicator and the methods, and apparatus described herein may be used in health care fields, scientific fields, or the like. These may be used in commercial and industrial applications where sterilization, disinfection, sanitization, or the like, may be desired, for example, sterilization, disinfection and sanitization of medical, dental and/or surgical instruments and/or implants, food processing, pharmaceutical manufacturing, or the like.

The biological indicator or sterilization indicator described may be used in any sterilization process. These may include sterilization processes where the sterilization medium or sterilant may be steam or dry heat, as well as one or more gaseous sterilants, one or more liquid sterilants, or the like. The gaseous sterilants may comprise ethylene oxide, gaseous hydrogen peroxide, gaseous peracetic acid or the like. The liquid sterilants may comprise formalin (formaldehyde gas dissolved in water and optionally containing methanol to inhibit the formation of toxic substances), glutaraldehyde, peracetic acid, liquid hydrogen peroxide, or the like.

The sterilization indicator or biological indicator may be used to examine the lethality of sterilants against any microorganism with less resistance to the sterilization process.

The term "microorganism" or "microorganisms" refers to bacteria, viruses or fungi. The microorganism can be in a spore form or vegetative state. In some embodiments, *Bacillus, Clostridium, Neurospora*, and/or *Candida* species of microorganisms are applied to the SCBI. In various embodiments, *Bacillus* and *Clostridia* species are used to monitor sterilization processes utilizing saturated steam, dry heat, gamma irradiation, and ethylene oxide. In some embodiments, microorganisms such as *Geobacillus stearothermophilus* and *Bacillus atrophaeus* monitor sterilization conditions. *Geobacillus stearothermophilus* is particularly useful to monitor sterilization under steam sterilization conditions. In various embodiments, microorganisms may include bacteria such as *Escherichia coli, Legionella* sp., *Campylobacter* sp., and other enteric bacteria. The bacteria can include *Staphylococcus* and *Streptococcus* species and other human pathogenic microorganisms such as *Cryptosporidium*.

The term "spore" refers to an asexual reproductive cell capable of developing into a new individual without fusion with another reproductive cell. The term "spore" is used throughout the present disclosure for simplicity, but it should be understood that microorganisms (e.g., bacteria, fungi, viruses, etc.), spores (e.g., bacterial, fungal, etc.), enzymes, substrates for enzymatic activity, ATP, microbial metabolites, or a combination thereof, can be used in the biological indicator of the present disclosure. In one aspect, the spores of the present disclosure are produced by bacteria and fungi. Bacterial spores serve largely as a resting, or dormant stage in the bacterial life cycle, serving to preserve the bacterium through periods of unfavorable conditions. Many bacterial spores are highly durable and can germinate even after years of dormancy. The bacterial spore is recognized as the most resistant form of microbial life. It is the life form of choice in all tests for determining the sterilizing efficacy of devices, implants, chemicals and processes. In one embodiment, one way of detecting whether bacteria are still present on a carrier of the biological indicator is through enzyme activity. The enzyme alpha-D-glucosidase has been identified in spores of *Geobacillus stearothermophilus*, such as those commercially available as "ATCC 7953" from American Type Culture Collection, Rockville, MD. *Bacillus atrophaeus* is particularly useful to monitor conditions of gas and dry heat sterilization. The enzyme beta-D-glucosidase has been found in *Bacillus atrophaeus* (e.g., commercially available as "ATCC 9372" from American Type Culture Collection). In various embodiments, the spores comprise *Bacillus, Clostridium, Neurospora, Candida*, and, and/or *Cryptosporidium*. In some embodiments, the spores comprise *Geobacillus stearothermophilus* and/or *Bacillus atrophaeus*.

The term "endospore" refers to a dormant, tough, and non-reproductive structure produced by certain bacteria from the Firmicute phylum. Examples of endospores include, but are not limited to, *Geobacillus stearothermophilus, Bacillus subtilis, Bacillus subtilis globigii, Bacillus atrophaeus, Clostridium sporogenes, Bacillus cereus*, and *Bacillus circulans*. Examples of fungi include *Aspergillus niger, Candida albicans, Trichophyton mentagrophytes*, and *Wangiella dermatitis*. Examples of mycobacteria which can be utilized in the present disclosure include *Mycobacterium chelonae, Mycobacterium gordonae, Mycobacterium smegmatis*, and *Mycobacterium terrae*.

The term "vegetative bacteria" refers to a state of bacteria in which growth and reproduction occurs and where spore formation does not occur. Examples of vegetative bacteria include, but are not limited to, *Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis*, and *Stenotrophomonas maltophilia*.

The phrase "biological activity" generally refers to any specific catalytic process or groups of processes associated with a biological cell. Nonlimiting examples of biological activities include catabolic enzyme activities (e.g., carbohydrate fermentation pathways), anabolic enzyme activities (e.g., nucleic acid, amino acid, or protein synthesis), coupled reactions (e.g., a metabolic pathway), biomolecule-mediated redox reactions (e.g., electron transport systems), and bioluminescent reactions. "Predetermined" biological activity means that the method is directed toward the detection of a specific biological process (e.g., an enzyme reaction) or group of biological processes (e.g., a biochemical pathway). It will be appreciated by a person having ordinary skill in the art that certain predetermined biological activities may be associated with a particular type of cell (e.g., microorganism) or a pathological process.

Similarly, it should be understood that phrases used in the present disclosure that include the term "spore," such as "spore carrier," "spore reservoir," "spore region," "spore growth chamber," and the like, are used merely for simplicity, but that such components, elements or phrases equally apply to other sources of biological activity and are not intended to refer only to spores. For example, the above phrases can also be referred to as a "source carrier," a "source region," a "source reservoir," a "source growth chamber," and the like.

The process of bringing the spores and medium together can be referred to as "activation" of the biological indicator. That is, the term "activation" and variations thereof, when used with respect to a biological indicator, can generally refer to bringing spores of the biological indicator in sterilant communication with a liquid or medium (e.g., an aqueous mixture comprising a nutrient medium for the spores). For example, when a frangible container within the biological indicator that contains the medium is at least partially fractured, punctured, pierced, crushed, cracked, or the like, such that the medium has been put in sterilant communication with the spores, the biological indicator can be described as having been "activated." Said another way, a biological indicator has been activated when the spores have been exposed to the medium which was previously housed separately from the spores.

Suitable enzymes can include hydrolytic enzymes and/or enzymes derived from spore-forming microorganisms, such as *Bacillus stearothermophilus* and *Bacillus subtilis*. Enzymes from spore-forming microorganisms that can be useful in the biological indicators of the present disclosure can include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase and fatty acid esterases.

Some embodiments of the biological indicator can include chromogenic and/or fluorogenic substrates that react with enzymes to form detectable products. These substrates may be classified in two groups based on the manner in which they create a visually detectable signal. The substrates in the first group react with enzymes to form enzyme-modified products that are themselves chromogenic or fluorescent. Substrates in the second group form enzyme-modified products that can react further with an additional compound, or compounds, to generate a color or fluorescent signal. Examples of fluorogenic substrates include, for example, 4-methylumbelliferyl-α-D-glucopyranoside (MUG) or para-nitrophenol-α-D-glucoside (PNPG). These include fluorescent moieties that when metabolized allow fluorescence and detection.

As a result, the phrase "detectable product" can refer to any molecule, compound, substance, substrate, or the like, or combinations thereof, that can be detected by any of the detection methods or processes described below. For example, such detectable products can be a sign of the viability of a source of biological activity, and detection of such products can generally indicate the failure or inadequacy of a sterilization process.

In some embodiments, the source of active enzyme can be (1) the purified, isolated enzyme derived from an appropriate microorganism; (2) a microorganism to which the enzyme is indigenous or added by genetic engineering; and/or (3) a microorganism to which the enzyme has been added during sporulation or growth, such that the enzyme is incorporated or associated with the microorganism, e.g., an enzyme added to a spore during sporulation which becomes incorporated within the spore. In some embodiments, the microorganisms which may be utilized as the source of an enzyme include bacteria or fungi in either the spore or vegetative state. In some embodiments, the enzyme source includes *Bacillus, Clostridium, Neurospora, Candida*, or a combination of such species of microorganisms.

The enzyme alpha-D-glucosidase has been identified in spores of *Bacillus stearothermophilus*, such as those commercially available as "ATCC 8005" and "ATCC 7953" from American Type Culture Collection, Rockville, Md. The enzyme beta-D-glucosidase has been found in *B. subtilis* (e.g., commercially available as "ATCC 9372" from American Type Culture Collection).

In the event that an isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. In such a case, the method of the present disclosure may include the step of incubating any viable microorganism remaining after the sterilization cycle with an aqueous nutrient medium to confirm the sterilization efficacy.

In general, monitoring the effectiveness of the sterilization process can include placing the biological indicator of the present disclosure in a sterilizer. In some embodiments, the sterilizer includes a sterilization chamber that can be sized to accommodate a plurality of articles to be sterilized and can be equipped with a means of evacuating air and/or other gases from the chamber and a means for adding a sterilant to the chamber. The biological indicator of the present disclosure can be positioned in areas of the sterilizer that are most difficult to sterilize (e.g., above the drain). Alternately, the biological indicator of the present disclosure can be positioned adjacent (or in the general proximity of) an article to be sterilized when the biological indicator is positioned in the sterilization chamber. In addition, the biological indicator can be positioned in process challenge devices that can be used in sterilizers.

The sterilization process can further include exposing the article(s) to be sterilized and the biological indicator to a sterilant. In some embodiments, the sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological indicator.

In general, after the biological indicator has been exposed to a sterilization cycle, a liquid (e.g., a growth media, water that can be mixed with a solid growth media, etc., or combinations thereof) can be introduced to the spores. As mentioned above, the step in which the liquid is introduced to the spores can be referred to as "activation" of the biological indicator or the "activation step." If the spores have survived the sterilization cycle, the liquid will facilitate metabolic activity and/or growth of the spores, and such activity and/or growth can be investigated. If growth is observed, the sterilization cycle is generally deemed ineffective.

Reference will now be made in detail to various embodiments of the present disclosure, examples of which are illustrated in the accompanying drawings. While the embodiments of the present disclosure will be described in conjunction with the illustrated embodiments, it will be understood that they are not intended to limit the disclosure to those embodiments. On the contrary, the disclosure is intended to cover all alternatives, modifications, and equivalents, which may be included within the disclosure as defined by the appended claims.

The headings below are not meant to limit the disclosure in any way; embodiments under any one heading may be used in conjunction with embodiments under any other heading.

Biological Indicator Reader

The biological indicator reader of this disclosure is designed, in one embodiment, to provide two primary functions, namely, incubating a biological indicator (BI) and detecting a possible sterilization failure. The incubation is typically conducted in a constant temperature BI holder or receiving BI holder at about 60° C. A small cylindrical BI is placed in the receiving BI holder to incubate the test sample (inside the BI) at 60° C. for a fixed amount of time, for example, about 30 minutes. During this time, an optical system, for example, a UV light emitter can expose the test sample to short bursts of ultra-violet light (UV), the optical system is configured to detect a fluorescent light signal from the sample. During alternate time intervals, when the UV light is off, the optical system also is configured to detect a fluorescent light signal from the sample. The difference between these two signals are data measured and recorded. The fluorescence is produced by an enzymatic reaction involving 4-methylumbelliferyl-α-D-glucopyranoside (MUG) or para-nitrophenol-α-D-glucoside (PNPG), which is associated with spore growth inside the self-contained BI. Over the duration of the test, if enough fluorescent signal is detected, the BI test is considered positive and a sterilization failure is detected. On the other hand, if the test has not detected enough fluorescent signal, the test is negative, and the sterilization is valid and confirmed.

The BI reader is one component of a larger Rapid Read Biological Indicator System (RRBIS) which comprises, consists essentially of or consists of the BI reader and multiple biological indicators (BI). The Rapid Read Biological Indicator System provides a rapid monitoring of steam sterilization processes performed at health care facilities. For example, a BI can be placed in the same sterilization environment as medical, dental or surgical instruments being sterilized. After the sterilization sequence is complete, the BI is then placed in the BI reader to verify that sterilization of the medical instruments was successful. If the BI sample is sterilized, then the medical instruments would also be sterilized. In some aspects, the BI reader is designed to incubate and automatically read a 3-hour rapid read BI for steam at about 60° C. for a final fluorescence result at about one (1) hour or less. In many aspects, the expected test time can be about 30 minutes. The BI reader is also designed to allow for further incubation of the above mentioned BI for a pH color change result after 48 hours. A positive fluorescence reading, or a pH color change indicates a steam sterilization process failure.

Examples of conventional biological indicators that can be used with the BI reader of the current disclosure are described in U.S. Pat. Nos. 5,252,484; 6,025,189; and 6,063,591, which are incorporated herein by reference as if set forth in full. As described in more detail in this application, the BI reader of this disclosure differs in many respects from conventional BI readers. Biological indicators that can be used in the BI reader of the current application can be obtained from Crosstex International, Inc. Hauppauge, New York, USA.

Figure 1:
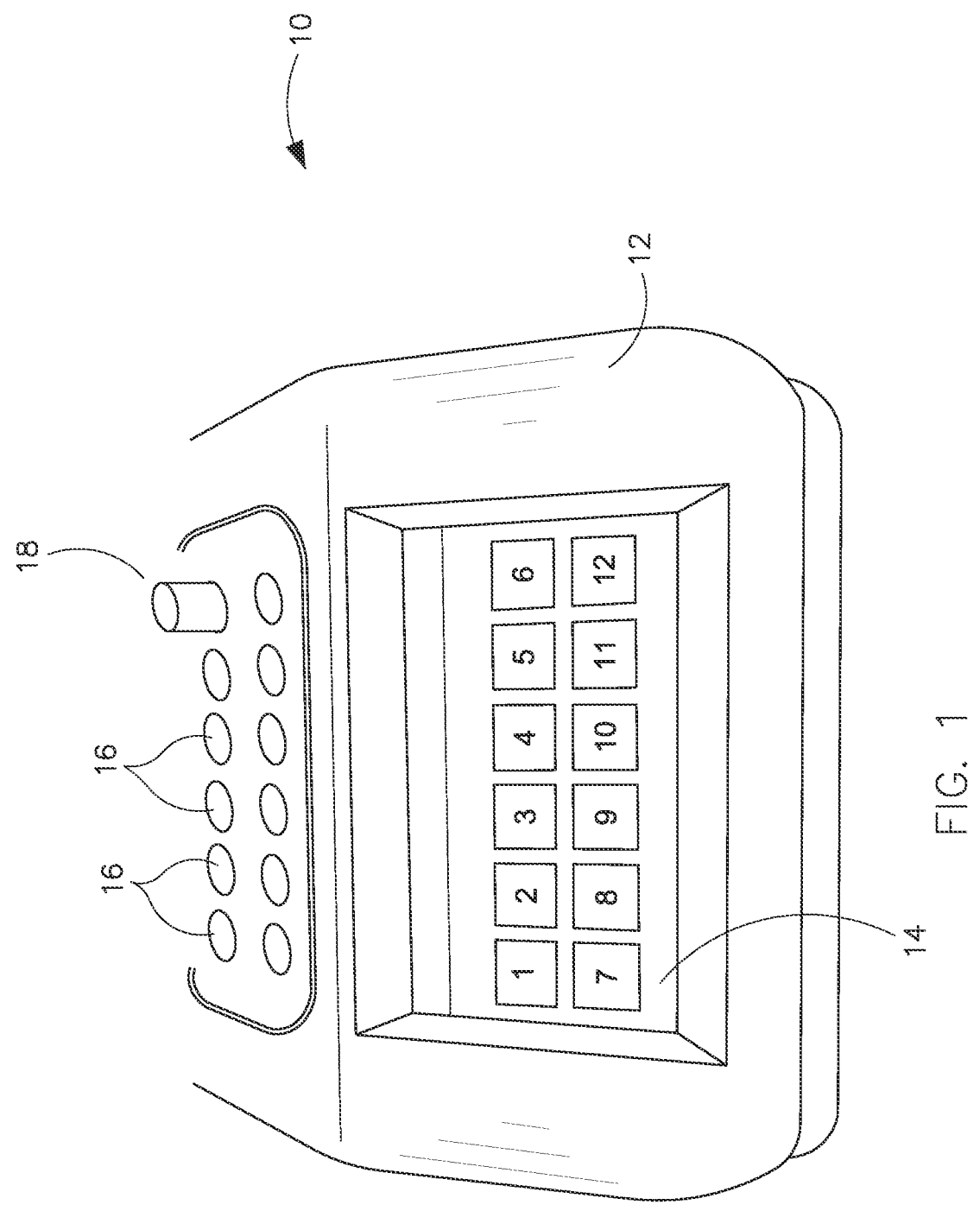
FIG. 1 is a perspective view of a biological indicator reader according to one embodiment of the present disclosure, the biological indicator reader comprising at least one biological indicator positioned in each biological indicator holder.

FIG. 1 illustrates a biological sterilization or indicator (BI) reader 10 according to one embodiment of the present disclosure. The BI reader 10 includes a housing 12, a display panel 14, twelve (12) receiving BI holders 16, each BI holder 16 dimensioned to receive at least a portion of a biological indicator 18.

As further illustrated in FIGS. 1-4A, 4B and 4C, in several embodiments, BI reader 10 comprises twelve (12) BI holders 16 each for receiving a BI 18. Each BI holder 16 operates independently. After the BI is removed from a sterilization chamber along with medical, dental and/or surgical instruments, after a sterilization process has occurred (not shown), the BI 18 is activated by crushing the vial to mix the carrier containing spores with the growth medium. The BI 18 is then placed in a BI holder 16 where, in some embodiments, a 30-minute countdown begins. In this embodiment, all twelve BI holders are maintained at a constant temperature of about 60° C., and the 30-minute countdown is the incubation period for the growth media 25 present on the BI carrier 28. At the end of the incubation period, UV light is emitted at the BI and the BI reader 10 will indicate a positive or negative result by the amount of fluorescent signal received from the BI carrier 28. The test result is then displayed on a display panel 14, which can be an LCD touch screen and a record of the test is added to a software file called the history log.

Figure 2:
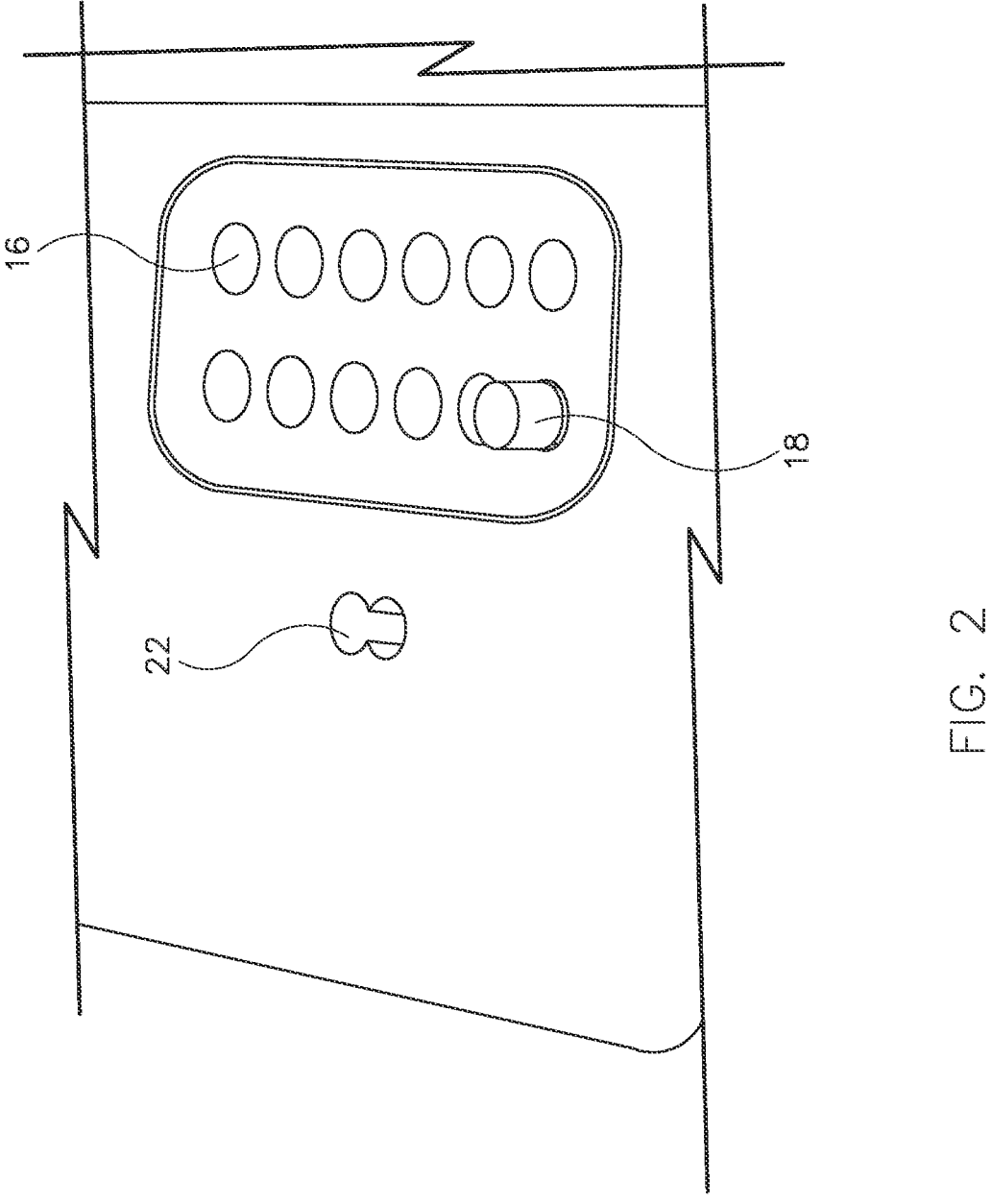
FIG. 2 is a top view of the biological indicator reader according to one embodiment of the present disclosure showing twelve (12) biological indicator holders and one (1) biological indicator crusher.

In many aspects of the present application, as illustrated in FIGS. 2, 4A and 4B, housing 12 of the BI reader 10 further comprises a BI crusher 22 disposed proximately to the biological indicator holders 16. BI crusher 22 is sized to crush the crushable ampoule 24 inside BI container 20 and release the growth medium 25 within each BI 18. In some aspects, BI reader 10 includes a cover (not shown) for the plurality of biological indicator holders 16. The BI reader 10 also contains a display panel 14 in FIG. 1, which is coupled to the electronic controller system 50 and is configured to provide an indication of the effectiveness of the sterilization process associated with each biological indicator. Although the electronic controller system 50 is shown as separate, it may be part of the housing or combined in one or more computer systems. Indeed, the electronic controller system may be one or more hardware, software, or hybrid components residing in (or distributed among) one or more local or remote computer systems. FIG. 4D illustrates an embodiment of a dissembled biological indicator. The biological indicator, or a BI vial comprises cap 26, cap filter 21, ampoule 24, BI carrier support 23, BI carrier 28, sleeve 29 and label 290. In some embodiments, the ampoule can be a crushable glass media ampoule. The BI carrier can be a spore strip. The BI carrier support can be a spore strip support. The sleeve can be a plastic sleeve containing ampoule, BI carrier and BI carrier support. The label can contain information about the vial and/or its contents, which can be inputted in the BI reader. The plastic outer sleeve can be soft and pliable. To activate the BI vial, the glass ampoule is broken ("crushed") to allow the liquid media inside the ampoule to wet the spore strip. The BI crusher can match the shape of the biological indicator holder or well of the BI reader. When placing a BI vial in the crusher, it is pushed from one side to the other to break the glass ampoule and activate the BI vial. When the ampoule liquid media makes contact with the spore strip, if the spores are still alive after sterilization, they produce a fluorophore byproduct, such as for example, a 4 MU byproduct. If the BI spores are dead, then no fluorophore byproduct is produced.

It also should be readily apparent that the components of the biological indicator as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (e.g., recording medium or other memory units) to produce the functionality referred to herein may be utilized to implement the illustrated embodiments. It also will be understood that a plurality of computers or servers can be used to allow the biological indicator to be a network based system having a plurality of computers linked to each other over the network or Internet or the plurality of computers can be connected to each other to transmit, edit, and receive data via cloud computers.

FIG. 3A is a perspective view of an embodiment of a BI holder block 34 of the BI reader 10. In this embodiment, the BI reader further includes a heater subsystem which comprises a heater element 36, an electronic switch, an electronic current measurement circuit, temperature sensors, all connected to an electronic controller system 50, which can be a microprocessor. In one embodiment as illustrated in FIG. 3A, BI holder block 34 of the BI reader includes six (6) BI holders which are heated by heater element 36, which in turn is connected to electronic controller system 50. In some embodiments, the goal of the heater subsystem is to maintain the twelve BI holders at about 60° C. When first powered on at room temperature, the expected time to reach 60° C. is about 30 minutes. Afterwards, the power is left on, and the well temperature remains constant until the BI reader is disconnected from power. Electronic controller system 50, which can be a microprocessor, monitors the well temperature using two temperature sensors and adjusts the current delivered to the heater element 36 to keep the temperature constant. FIG. 3B illustrates an embodiment of heater control. The heater control comprises heater element 302 and heater block 308 are placed in the middle of and adjacent two temperature sensors 304, 306. There are two temperature sensors for twelve BI holders, one for each BI reader block; during operation, the two temperature sensors of the BI reader should read the same value. In some embodiments, temperature readings from the two temperature sensors are within 4 degrees Celsius.

As illustrated in FIG. 5, in some embodiments, each BI holder 16 includes a first side aperture 30 and a second aperture 32 at the bottom of the BI holder, which has a square shape here. It will be understood that the apertures can have any shape, for example, round, square, triangular, rectangular, oval or the like. In one embodiment, first side aperture 30 is round and second aperture 32 at the bottom of the BI holder, which has a square shape.

FIG. 6 is a schematic of one embodiment of BI holder 16 of biological indicator reader 10. Each BI holder 16 has a UV light emitter 40 incident upon the BI container 20 from the side and a single optical detector 42 directly below. In one aspect, the UV light emitter can be a UV light emitting diode (LED) having a wavelength of from about 345 nm to about 425 nm. In one embodiment, the wavelength has a peak power at 365 nm. Each BI holder also comprises a well to receive a biological indicator.

UV light emitter 40 can be used in two ways. In one way, UV light emitter 40 excites the growth media 25 inside the BI container 20 including the excitement of a fluorophore called 4-methylumbelliferone or 4 MU to emit a fluorescent light signal. In the second way, the UV light emitter is used to detect when a BI container 20 is placed into BI holder 16.

For both functions, the BI reader 10 of this disclosure utilizes only one optical detector 42, for example, a UV photodetector.

Unlike, BI readers in the prior art, the current BI reader, in some embodiments, uses only one photodetector or optical detector and this photodetector or optical detector is positioned at the bottom of the well. In addition, because there is only one photodetector or optical detector per well, in some embodiments, there is likewise only one corresponding aperture at the bottom of each well that allows the transmitted UV light from the activated BI through the aperture and to the photodetector or optical detector. In this way, the BI reader has a reduced number of components compared to conventional BI readers having a plurality of photodetectors or optical detectors per well.

In various embodiments, the geometry of the BI holder allows the same optical detector 42 to sense when a BI container 20 is placed in it. As further illustrated in FIGS. 4C, 5 and 6, the UV light enters the BI holder 16 from the side through first side aperture 30, which has a circular shape, and is incident upon the BI container 20 on the side, near the bottom of the BI container 20 of BI 18. The UV light then passes through the outer sleeve 29 of BI container 20 and is transmitted from the BI carrier 28 (shown in 4C). A portion of the transmitted light then transmits through the bottom of outer sleeve 29 of the BI container 20, through the second aperture 32 (which has a square shape) at the bottom of the BI holder 16 and arrives at the optical detector 42.

Optical detector 42 receives light from three sources, namely, UV light emitter 40, fluorescent light from biological sample, if any, and room light that has leaked through the gap of the wall of BI holder 16 and the BI container 20. In many aspects, optical detector 42 is a UV photodetector and is configured to detect (i) the presence or absence of a BI 18 in the BI holder 16 and/or (ii) any fluorescence emitted by the BI 18.

In various aspects, each BI holder 16 has a dedicated ultra-violet (UV) light emitter 40 with optical wavelength centered at 365 nm. An optical path exists from the UV light emitter 40, through the BI vial, and last to exit to the optical detector 42, which, in many embodiments, is a UV photodiode. To limit the bandwidth of the UV light, a first optical bandpass filter 60 (290 nm to 390 nm) is present in the path of the UV light before it enters the BI holder through first side aperture 30. Each UV optical path is isolated from other UV paths by mechanical design of optical barriers. The intensity of UV light emitted from each UV LED is controlled electronically by an electronic controller system 50. In many aspects, electronic controller system 50 is a microprocessor having a memory coupled to the electronic controller system and configured to receive and store data indicative of the fluorescence of each BI 18 based on fluorescence intensity signals received by electronic controller system 50.

In other aspects, each BI holder 16 is also equipped with optical detector 42, in some aspects, a photodiode that can detect UV signals of 430 nm, that is, the fluorescent signal. The output of each optical detector 42 is transmitted through an analog multiplexer (not shown) then electronically amplified and integrated. The readings from all 12 BI holders are then time multiplexed and fed to the analog-to-digital converter inside the electronic controller system 50, which can be a microprocessor. Electronic controller system 50 can then measure the intensity of each of the fluorescent signals. Each UV photodiode is optically isolated from all others so that there is no overlap of received fluorescent signals. Additionally, each optical detector 42 has two optical filters, a second optical filter 62 and a third optical filter 64 below second optical filter 62 and in the path to optical detector 42 used to limit the bandwidth of the detected signal to a bandpass from about 410 nm to about 560 nm and block the excitation wavelength of 365 nm. In some embodiments, the bandpass is from about 412 nm to about 418 nm. In some aspects, third optical filter 64 is positioned below second optical filter 62. Each UV photodiode also has an O-ring that mechanically seals its top surface to the enclosure to prevent any sterilant ingress.

As illustrated in FIG. 8, in one embodiment, data is taken with the UV light emitter 40 on and off. The difference between these two values is used as the measured data. When a crushable ampoule 24 (illustrated in FIG. 4B) is present in BI holder 16, the data values are above 900 relative fluorescent units (RFU). When a BI holder is empty, the data values are below 900 RFU In FIG. 8, graph #01 is an embodiment of a data record where the BI holder starts out containing a BI. The BI is then taken out of the BI holder at about 300 seconds and then placed back in the BI holder at about 600 seconds. This graph can be displayed on the BI reader or on a display of a computer linked with the BI reader.

In various aspects, BI reader 10 is controlled by an electronic controller system 50 which is coupled to the optical detector 42. In some aspects, electronic controller system 50 is configured to receive an input signal emitted when optical detector 42 receives light exiting each biological indicator holder 16 and to provide an output signal indicating sterilization process failure or success.

FIG. 7 illustrates an embodiment of the BI reader 10 wherein the BI reader further comprises a horizontal circuit board 52 positioned under the plurality of biological indicator holders 16 and a vertical circuit board 54 orthogonal to the horizontal circuit board and proximate the biological indicator holders. In this embodiment, UV light emitter 40 is mounted on the vertical circuit board 54 and the optical detector 42 is mounted on the horizontal circuit board 52.

Biological Indicator

A typical biological indicator being used today is a self-contained biological indicator (SCBI), which contains, among other things, microorganisms, culture medium, carrier, and a crushable container (e.g., vial). Examples of various features that may be employed in an example of a BI 18 are described in U.S. application Ser. No. 15/513,887, assigned to SPS medical Supply Corp., NY, USA, which is incorporated herein by reference as if set forth in full. Biological indicators that can also be used in the BI reader of the current application can be obtained from Crosstex International, Inc. Hauppauge, New York, USA.

In various embodiments, BI 18 can be read by BI reader 10. As illustrated in FIGS. 4C and 9, BI 18 has a BI container 20 which comprises a cylindrical outer sleeve 29, a glass media vial or crushable ampoule 24 which comprises growth media 25 (that can have, for example, 4-methylumbelliferyl-α-D-glucopyranoside (MUG) or para-nitrophenol-α-D-glucoside (PNPG)) and a BI carrier 28 for the biological sample or microorganisms, in which the carrier is separated from crushable ampoule 24 but is available within the BI container 20. The BI container 20 is configured to encase or self-contain the multiple components of the biological indicator. In various embodiments, the BI and its components are disposable.

In some aspects, BI container 20 can be made of semitransparent plastic. In other embodiments, the BI container can be made from other materials. For example, the container comprises a glass, a metal (e.g., foil), a polymer (e.g., polycarbonate (PC), polypropylene (PP), polyphenylene (PPE), polythyene, polystyrene (PS), polyethylene, polypropylene, polyester (e.g., polyethylene terephthalate (PET)), polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof.

In various aspects, BI 18 comprises a BI carrier 28 as illustrated in FIG. 9. In the embodiment shown, the BI carrier is shown as 28 and is disposed within the BI container 20. In some embodiments, BI carrier 28 is fixed to a section of container 20. In some embodiments, BI carrier 28 is fixed to the container via a slit in the container, a ledge in the container, a ridge in the container, clips, snaps, adhesive, anchors, buttons, staples, posts, and/or fixation plates. In some embodiments, the carrier is inserted into a bifurcated section of the container. In some embodiments, the carrier is disposed in a breakable chamber of the container separated from another section of the container. In some embodiments, the carrier is freely moving in the container.

In various embodiments, the carrier can be made from a variety of materials. The carrier is configured to be inoculated with a microorganism and other components, for example, a humectant, anti-agglomerating agent or surfactant. The carrier will hold the microorganism and other components on it. The carrier will allow contact with the growth media in the biological indicator after the sterilization procedure so that any surviving microorganisms can grow and/or metabolize the nutrients in the growth media, which will cause a detectable signal that can be read by eye or machine.

Although, in some aspects, the plastic outer sleeve 29 of BI 18 attenuates light intensity, it allows a percentage of light through. Inside the vial, near the bottom, is BI carrier 28 for the biological sample as shown in FIG. 4C. Biological indicator 18 is activated by crushing the crushable BI container 20 with BI crusher 22 prior to insertion into the BI holder 16, wherein fluorescence is detected when a viable enzyme from a viable microorganism digests the culture medium. When UV light shines on biological sample of BI carrier 28, it emits fluorescent light in proportion to the biological population. The fluorescent light then transmits through the bottom of the outer sleeve 29 to the optical detector 42.

In some embodiments, the detection method of the effectiveness of at least a sterilization process may be selected based on the property of interest and may include, for example, fluorometric, visual, pH, and spectroscopic detection methods. The detection of a measurable change in an indicator property within an established period of time indicates viability of microorganisms and inadequate sterilization. The absence of a measurable change within the established period of time demonstrates that the sterilization process was lethal to the test microorganisms and, thus, adequate. In some embodiments, the detection can be determined by measuring turbidity of the growth media by eye or machine.

In one embodiment, the BI growth media 25 contains 4-methylumbelliferyl α-D-glucoside (MUG). MUG is an enzyme substrate. In various aspects, the spores used in BI 18 contain the enzyme α-glucosidase. Any surviving spores will make the α-glucosidase enzyme. When MUG and α-glucosidase contact each other in the BI container 20, α-glucosidase digests the MUG to release a fluorophore called 4-methylumbelliferone or 4 MU. Esters of 4-methylumbelliferone (4-MU) do not fluoresce unless cleaved to release the fluorophore. Fluorometric enzyme assays are based on the hydrolysis of 4-MU-containing substrates such as β-4-MU-glucuronide by β-glucuronidase (GUS), or b-4-MU-galactose by β-galactosidase (GAL). Cleavage of 4-methylumbelliferyl-b-D-galactoside by β-galactosidase enzyme yields the fluorescent molecule 4-MU that emits light at 460 nm when excited by 365 nm UV light. In short, when UV light having a wavelength of about 365 nm shines on 4 MU, it excites the molecule and causes it to emit light or fluoresce at a specific wavelength about 430 nm. It is the light emitting feature of 4 MU that enables a very small amount of it to be detected by a UV light optical detector 42. Detection of a sufficient level of fluorescence during incubation constitutes a positive result, that is, it indicates the presence of viable biological material. A positive result indicates the failure of the associated sterilization process.

In various aspects, with further reference to FIG. 9, each BI 18 comprises a BI container 20 which can have an outer sleeve 29, a crushable ampoule 24 inside the outer sleeve and a cap 26. In some aspects, crushable ampoule 24 can be a vial containing growth media for the microorganisms contained in the outer sleeve 29. Prior to sterilization, the outer sleeve 29 comprises viable microorganisms containing an enzyme and crushable ampoule or vial that contains a culture medium capable of promoting growth of the microorganisms present in outer sleeve 29.

In some embodiments, cap 26 is disposed at an end of BI container 20. In other embodiments, cap 26 is configured to facilitate penetration of the sterilant from the sterilizing chamber into the biological indicator during the sterilization process. In some embodiments, the cap comprises openings, such as, for example, vents 27 and/or slits. In some embodiments, the cap is friction fitted into the end of the biological indicator. In some embodiments, the cap is configured for threaded engagement with the end of the container. In some embodiments, the cap is adhered to the end of the biological indicator via adhesive, clips, snaps and/or flanges. In some embodiments, the cap is made from various materials including, but not limited to polycarbonate, polyolefins, polyamide, polymethacrylates, polymethylpentenes, and/or polyesters.

The culture medium within the crushable ampoule 24 comprises 4-methylumbelliferyl-α-D-glucopyranoside (MUG) or para-nitrophenol-α-D-glucoside (PNPG). In many aspects, crushable ampoule 24 further comprises a pH indicator in the culture medium, which can show a positive indication of spore growth by changing color in the growth media.

In various embodiments, the carrier can be made from a variety of materials. In some embodiments, the carrier can be made from any inorganic material such as silicon including crystalline silicon; various types of glasses including soda-lime, borosilicate glass, phosphate glass, borophosphate glass, boroaluminosilicate glass, or the like; various ceramics which can be defined as earthly raw materials in which silicon and its oxide and complex compounds known as silicates occupy a predominate portion and which have been heated to high temperatures such as structural clay products including tile and terra cotta, various porcelains, porcelain enamels, or the like; metal such as stainless steel, iron, copper; various inorganic substrates containing metalized surfaces such as those immediately set forth, or various metal oxides of groups 4 through 14 of the Periodic Table including titanium oxide, zirconium oxide, iron oxide, copper oxide, aluminum oxide, silica such as quartz, sapphire, and any combination thereof. In some embodiments, the carrier comprises metal oxide.

In various embodiments, the carrier can be made from stainless steel. The stainless-steel carrier is configured to interact with the humectant, anti-agglomerating agent or surfactant, such that microorganisms inoculated onto the carrier will not clump together on the surface of the carrier, thereby causing a uniform distribution of the microorganisms. In some embodiments, an indent is defined within an end of the stainless-steel carrier that is configured for engagement with the microorganisms.

In some embodiments, the carrier can be made from various organic compounds including cellulose in various forms such as paper, filter paper, chromatography paper, blotter paper cardboard, or the like. In some embodiments, the carrier can comprise of polymers, including, but not limited to, acrylic polymers including acrylic acid and acrylate polymers, various polyolefins such as polyethylene and polypropylene, polyvinyl alcohol polymers; polystyrene; and any combination thereof. In various embodiments, the carrier can be made from a combination of inorganic and organic compounds. In some embodiments, the carrier is made from only inorganic compounds. In some embodiments, the carrier is made from only organic compounds.

In some embodiments, the carrier is configured to be inoculated with the microorganism and a humectant, anti-agglomerating agent or surfactant. The carrier will hold the microorganism and the humectant, anti-agglomerating agent or surfactant on it. The carrier will allow contact with the growth media in the biological indicator after the sterilization procedure so that any surviving microorganisms can grow and/or metabolize the nutrients in the growth media, which will cause a detectable signal that can be read by eye or machine.

In some embodiments, the carrier is inoculated with the microorganisms. In various embodiments, the types of microorganisms include, but are not limited to spores, endospores, bacteria, vegetative bacteria, mycobacteria and/or fungi. In some embodiments, the microorganisms include, but are not limited to *Bacillus, Clostridium, Neurospora,* and/or *Candida* species of microorganisms, which are applied to the SCBI.

In various embodiments, *Bacillus* and *Clostridia* species are used to monitor sterilization processes utilizing saturated steam, dry heat, hydrogen peroxide, peracetic acid, ethylene oxide or a combination thereof.

In some embodiments, microorganisms such as *Geobacillus stearothermophilus* and *Bacillus atrophaeus* monitor sterilization conditions. *Geobacillus stearothermophilus* is particularly useful to monitor sterilization under steam sterilization conditions and under hydrogen peroxide sterilization conditions. *Bacillus atrophaeus* is also particularly useful for ethylene oxide and dry heat sterilization. In various embodiments, microorganisms may include bacteria such as *Escherichia coli, Legionella* sp., *Campylobacter* sp., and other enteric bacteria, as BI holder as *Staphylococcus* and *Streptococcus* species and other human pathogenic microorganisms such as *Cryptosporidium.*

In some embodiments, the microorganisms are spores. In various embodiments, the spores comprise *Bacillus, Clostridium, Neurospora, Candida,* and/or *Cryptosporidium.* In some embodiments, the spores comprise *Geobacillus stearothermophilus* and/or *Bacillus atrophaeus.*

In some embodiments, the microorganisms are endospores. In various embodiments, the endospores comprise *Geobacillus stearothermophilus, Bacillus subtilis,* *Bacillus subtilis globigii, Clostridium sporogenes, Bacillus cereus, Bacillus atrophaeus* and *Bacillus circulans* or a combination thereof.

In various embodiments, the microorganisms are fungi. In some embodiments, the fungi comprise *Aspergillus niger, Candida albicans, Trichophyton mentagrophytes, Wangiella dermatitis* or a combination thereof.

In some embodiments, the microorganisms are mycobacteria. In various embodiments, the mycobacteria comprise *Mycobacterium* chelonae, *Mycobacterium gordonae, Mycobacterium smegmatis,* and *Mycobacterium terrae* or a combination thereof.

In various embodiments, the microorganisms are vegetative bacteria. In some embodiments, the vegetative bacteria comprises *Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis,* and *Stenotrophomonas maltophilia* or a combination thereof.

In some embodiments, the carrier is inoculated with one or a combination of the microorganisms. In various embodiments, the carrier comprises the microorganisms at a distal end of the carrier closest to the growth media in the container. In some embodiments, the carrier comprises the microorganisms disposed throughout the carrier.

In one embodiment, the concentration of the microorganisms may be in the range of from about 101 to about 1014 colony forming units (cfu) when disposed on the carrier. In some embodiments, the concentration of microorganisms is in the range from about 104 to about 1010 cfu. In some embodiments, the concentration of microorganisms is in the range from about 106 to about 108 cfu. In some embodiments, the concentration of microorganisms is from about 101, 102, 103 104, 105, 106, 107, 108, 109, 1010, 1011, 1012 1013 or 1014 cfu.

Methods

This disclosure also provides a method for determining the effectiveness of at least a sterilization process. In many aspects, the method comprises providing a BI reader for reading a plurality of biological indicators to determine the effectiveness of at least a sterilization process. Each biological indicator is configured to exhibit fluorescence when the sterilization process has failed. Each reader comprises a housing having a plurality of biological indicator holders and each holder is configured to receive one of the plurality of biological indicators. Each biological indicator holder has a first aperture on a side and a second aperture on a bottom of the biological indicator holder. The first aperture is positioned to face the UV light emitter and can be round and the second aperture on the bottom of the biological indicator holder and can be square. In many aspects, a heater is coupled to the housing of the BI reader. The heater is configured to heat the plurality of biological indicator holders to a preselected temperature to incubate the biological indicators. In other aspects, a UV light emitter is configured to emit UV light through the first aperture on the side of each biological indicator holder. The BI reader also includes an optical detector positioned under the second aperture on the bottom of the biological indicator holder. The optical detector of the BI reader is configured to detect fluorescence intensity indicating the effectiveness of the sterilization process. The method also includes providing a biological indicator capable of exhibiting fluorescence to indicate the effectiveness of a sterilization process. The biological indicator provided by this method also comprises a crushable container. Upon subjecting of the biological indicator to the sterilization process to obtain a sterilized biological indicator, the crushable container of the sterilized biological indicator can be crushed to activate the indicator. Upon incubating the activated biological indicator in one of the biological indicator holders of the biological indicator at a preselected temperature and for a preselected period of time, the BI will be emitting UV light through the first aperture on the side of each biological indicator holder. A fluorescence intensity will be detected by the optical detector positioned under the second aperture on the bottom of the biological indicator holder indicating the effectiveness of the sterilization process.

In various aspects, the fluorescence intensity is detected when the UV light emitter is on and when the UV light emitter is off, a baseline value for the fluorescence intensity is obtained. When the biological indicator holder is empty, the emitted UV light is below 900 RFU and when the biological indicator is in the biological indicator holder, the emitted UV light is above 900 RFU. In some aspects, the UV light emitter emits UV light at a wavelength from about 290 to about 390 nm. In some embodiments, the wavelength is from about 345 nm to about 425 nm with peak power at 365 nm.

In many aspects, the biological indicator reader further comprises an electronic controller system coupled to the optical detector to receive a signal emitted when the optical detector receives light exiting each biological indicator holder and to provide an output signal indicating sterilization process failure or success. In various aspects, the electronic controller system is a microprocessor having a memory coupled to the electronic controller system and configured to receive and store data indicative of the fluorescence of each biological indicator based on fluorescence signals received by the electronic controller system.

In other aspects, the biological indicator reader further comprises a horizontal circuit board positioned under the plurality of biological indicator holders and a vertical circuit board orthogonal to the horizontal circuit board and proximate the biological indicator holders, wherein the UV light emitter is mounted on the vertical circuit board and the optical detector is mounted on the horizontal circuit board.

In some embodiments, each biological indicator comprises a container having an outer sleeve, a crushable vial inside the outer sleeve and a cap disposed at an end of the container. In some embodiments, the cap comprises vents for allowing inflow of the sterilant into the biological indicator.

In various embodiments, the outer sleeve of the biological indicator comprises viable microorganisms containing an enzyme and the frangible container is an ampoule that contains a culture medium capable of promoting growth of the microorganisms present in the outer sleeve. The culture medium within the ampoule comprises 4-methylumbelliferyl-α-D-glucopyranoside (MUG) or para-nitrophenol-α-D-glucoside (PNPG). Spores surviving the sterilization process produce the enzyme α-glucosidase, which digests MUG or PNPG releasing the fluorescent moiety that can be detected. In some embodiments, the crushable container further comprises a pH indicator in the culture medium.

In various embodiments, the housing of the reader further comprises a crusher disposed proximately to the biological indicator holders, the crusher sized to crush the crushable container and release the culture medium within each biological indicator; a cover for the plurality of biological indicator holders; and a display coupled to the electronic controller system and configured to provide an indication of the effectiveness of the sterilization process associated with each biological indicator.

In some embodiments, the housing further comprises an optical filter disposed above the optical detector and configured to filter light other than wavelengths approximately associated with fluorescence and UV excitation. In many embodiments, the optical detector is a UV photodetector and is configured to detect (i) the presence or absence of a biological indicator in the biological indicator holder and/or (ii) any fluorescence emitted by the biological indicator.

In various embodiments, a method for determining effectiveness of a sterilization procedure with a biological indicator is provided. In various embodiments, the method comprises subjecting the biological indicator to a sterilization cycle, the biological indicator comprising a deformable container having a crushable vial disposed therein comprising growth media and a carrier separated from the crushable vial but within the deformable container; activating the biological indicator by applying pressure to said deformable container to crush the vial so as to allow the growth media and the spores of the carrier to come into contact with each other; and incubating the biological indicator for a predetermined period of time to permit any growth of the spores surviving said sterilization cycle to grow in the growth media, wherein the growth provides a determination of the effectiveness of the sterilization procedure.

In some embodiments, the biological indicator further comprises a vented cap, as described herein, which allows a sterilant from the sterilization procedure to enter the deformable container and contact the spores on the carrier during the sterilization cycle. As the sterilant (e.g., hydrogen peroxide, peracetic acid, etc.) enters through the vented cap, it contacts the microorganisms on the carrier and should be in a sufficient quantity and time to kill all or most of the microorganisms should there be successful sterilization. In this way the object (e.g., instrument, implant, etc.) to be sterilized will be subject to the same successful sterilization procedure.

In some embodiments, the method comprises the biological indicator and all of its components and/or features, as described herein. In some embodiments, the sterilization procedure comprises contacting the spores with hydrogen peroxide sterilization, steam sterilization and/or ethylene oxide sterilization. In various embodiments, the sterilization procedure comprises contacting the spores with hydrogen peroxide sterilization.

In various embodiments, the biological indicator is placed within a sterilization chamber along with objects to be sterilized. During the sterilization cycle, a portion of the sterilant (e.g., hydrogen peroxide, peracetic acid, steam, etc.) permeates through the cap's openings, infiltrating into the container where the sterilant interacts with the microorganism (e.g., spores) inoculated on the carrier.

In some embodiments, after the sterilization cycle has been completed, the biological indicator is activated by squeezing the center, sides and/or the top of the deformable container or inverting it, which causes the crushable vial to break, thereby releasing the growth media contained within the crushable vial. In other embodiments, the biological indicator is activated by crushing the crushable container prior to incubating it in the biological indicator holder. The growth media will then contact the microorganisms (e.g., spores).

The biological indicator is incubated for a predetermined time, in some aspects, 30 minutes, at an appropriate temperature of about 60° C. At the end of the incubation period, a detector, as described herein, is used to determine whether any spores survived the sterilization process. In various embodiments, a positive indication of spore growth is shown via a pH indicator and the pH indicator can change color in the growth media.

Biological Indicator System

A biological indicator system for detecting the effectiveness of a sterilization process is also provided. The BI system comprises a biological indicator reader for reading a plurality of biological indicators to determine the effectiveness of at least a sterilization process, each biological indicator configured to exhibit fluorescence when the sterilization process has failed. The BI reader comprises a housing having a plurality of biological indicator holders, each holder configured to receive one of the plurality of biological indicators, each biological indicator holder having a first aperture on a side and a second aperture on a bottom of the biological indicator holder. The BI reader also includes a heater coupled to the housing and configured to heat the plurality of biological indicator holders to a preselected temperature and a preselected period of time to incubate the biological indicators. The BI reader further includes a UV light emitter configured to emit UV light through the first aperture on the side of each holder; and an optical detector positioned under the second aperture on the bottom of the biological indicator holder, the optical detector configured to detect fluorescence intensity indicating the effectiveness of the sterilization process; and a biological indicator containing a fluorescent moiety, spores, growth media and a crushable container, the biological indicator being sterilizable and configured to receive UV light from the UV light emitter.

FIG. 10 is a partial cross-sectional side view of a biological indicator system according to an embodiment of the present disclosure, the biological indicator system including a biological indicator shown in a perspective view. FIG. 10 illustrates an embodiment of biological indicator system 70 which comprises, consists essentially of or consists of BI reader 10 and BI 18. BI 18 comprises BI container 20 having a cap 26, which cap contains vents 27. BI 18 is located in BI holder 16, which is a well. An empty well is also illustrated in FIG. 10. BI system 70 further includes UV light emitter 40 which is used to excite growth media that can be present inside the BI container 20 to emit a fluorescent light signal. UV light emitter 40 can also be used to detect whether BI container 20 was placed into BI holder 16. For both functions, the BI reader 10 of this disclosure utilizes only one optical detector 42, for example, a UV photodetector. As illustrated in the embodiment of FIG. 10, optical detector 42 is placed directly below the bottom of BI holder 16. As a result, the geometry of the BI holder allows the same optical detector 42 to sense when a BI container 20 of BI 18 is placed in it. As further illustrated in FIG. 10, the UV light from UV light emitter 40 enters the BI holder 16 from the side through first side aperture 30, which has a circular shape in some embodiments, is incident upon the BI container 20 on the side, near the bottom of the BI container 20 of BI 18. In some embodiments, the BI reader further comprises a third aperture 31, which is a well entrance aperture that is disposed between the first side aperture 30, which is also a UV aperture, and the BI container 20. The UV light then passes through the outer sleeve 29 of BI container 20 and is transmitted from the biological sample carrier (not shown). A portion of the transmitted light then transmits through the bottom of outer sleeve 29 of the BI container 20, through the second aperture 32, which has a square shape in some embodiments, at the bottom of the BI holder 16 and arrives at the optical detector 42. In some embodiments, the BI reader comprises a fourth aperture 33. The fourth aperture is a well exit aperture disposed between the second aperture, which is also the optical aperture and the optical detector. In some embodiments, the BI reader further comprises an optical detector filter 35 disposed between the well exit aperture and the optical detector.

Electronic Controller System

In some embodiments, a biological indicator reader for reading a plurality of biological indicators to determine the effectiveness of at least a sterilization process is provided. In one embodiment, the reader comprises a housing having a UV light emitter coupled to the housing, the UV light emitter configured to emit UV light for a period of time; an optical detector configured to detect UV light; a multiplexer coupled to the optical detector, the multiplexer configured to generate an input signal from the optical detector; an amplifier coupled to the multiplexer, the amplifier configured to integrate a plurality of input signals for a period of time to indicate the effectiveness of the sterilization process based on the integration of the plurality of input signals.

The biological indicator reader can have an electronic controller system and/or an optical system as illustrated in FIGS. 6 and 11. In some embodiments, the controller 50 in FIG. 6 comprises the electronic controller system. FIG. 11 illustrates an embodiment of the electronic controller system and other various components connected to the system. In some embodiments, the electronic controller system 500 comprises various components including analog multiplexer 502, integrating amplifier 504, processor 506, real time clock (RTC) 508, random access memory (RAM) 510, heater switch 512, heater current measurement 514, resistance temperature detector/sensors 516A and 516B, UV LED driver 518, a secure digital (SD) card, Ferroelectric RAM (FRAM), battery 524, buzzer (526), bootloader processor 528, ethernet circuits with integrated magnetics 530, display 532, display backlight driver 534, electrically erasable programmable read only memory (EEPROM) 536A and 536B, and/or a combination thereof. FIG. 11 illustrates an embodiment of the combination of the various abovementioned components.

In some embodiments, the processor has 1 MB of onboard flash memory and 128 KB of RAM. The processor can also be referred to as a main processor herein. The processor supports an external DDR memory interface. In some embodiments, the processor's peripheral support includes Inter-Integrated Circuit (I2C), series of peripheral interfaces (SPI), secure digital (SD) card, Graphical LCD, and Ethernet. In some embodiments, the processor has analog features including 16-bit analog-to-digital converter (ADC) and 12-bit digital-to-analog converter (DAC). In some embodiments, the processor has an internal real time clock (RTC) that can be run on a separate battery power domain. In some embodiments, the system has a second processor that is used as a bootloader for the processor. In some embodiments, the system comprises two electrically erasable programmable read-only memories (EEPROMs) that are read by the bootloader processer, which loads the code into the processer, which then boots up the main code.

In some embodiments, the heater current measurement component converts an analog signal to a digital signal and sends the digital signal to the processor. In some embodiments, the processor controls the heater switch throughout a general purpose input/output (GPIO). In some embodiments, the heater switch simply turns the heater on or off through a metal-oxide-semiconductor field-effect transistor (MOSFET)), in which a digital pin is used to turn the MOSFET on or off. In some embodiments, the heater's operation is controlled through a closed loop control system, which automatically regulates the temperature to a predetermined set point. In some embodiments, a digital-to-analog converter (DAC) is used to control the gate voltage of the MOSFET such that it allows the control well block temperature and reduces noise levels in the electronics. In some embodiments, the reader comprises a heater current measurement component that can measure the temperature and sends the signal to the processor. In some embodiments, the heater current measurement circuit monitors the health and functionality of the heater element. If the heater element is damaged, the current value will change from its normal operating conditions. In some embodiments, the operating conditions of the heater require about 1.7 Amps (12 Volts/7 Ohms)+/−15%. In some embodiments, the operating conditions of heater require a range of 1.1, 1.3. 1.5. 1.7, 1.9, 2 Amps+/−1, 2, 3, 4, 5, 6, 7, 8, 9, 10, 11, 12, 13, 14, 15, 16, 17, 18, 19, 20, 21, 22, 23, 24, 25%. In some embodiments, the heater will shut down and log a system error when the value is outside the normal range. In some embodiments, the heater's current value is evaluated for every sample in a closed loop heater control algorithm.

The processor can control the temperature for incubation of the BI vial inside the reader. In some embodiments, the processor forms a closed loop control system with a resistance temperature detector (RTD) temperature sensor and an interface chip. The processor communicates with the interface chip through a series of peripheral interfaces (SPI). In some embodiments, there are two channels of temperature sensors; and each channel is expected to read the same value due to the physical placement of the RTD temperature sensors. In some embodiments, the redundancy of the value is a safety feature.

In some embodiments, the operating range of the well temperature can be about 60° C.+/−2° C. In some embodiments, the well temperature is about 50, 51, 52, 53, 54, 55, 56, 57, 58, 59, 60, 61, 62, 63, 64, 65, 66, 67, 68, 69, or 70° C. The BI has a close loop control, which regulates the temperature better than +/−2° C. The close loop control can regulate the temperature in a range of +/−0.5° C., +/−1, +/−2, +/−3, +/−4, +/−5, +/−6 degrees Celsius. A tolerance of greater than +/−4 degrees Celsius may cause problems in the BI sample. In some embodiments, a second heater control allows the heater to reach 60 degrees from the room temperature within 30 minutes. In some embodiments, the heater reaches 60 degrees from room temperature within 5, 10, 15, 20, 25, 30, 35 40, 45, 50, 55, or 60 minutes.

The device can have a third heater control, which contributes and helps regulate the temperature. In some embodiments, the processor reads the temperature to a high degree of resolution and accuracy. In some embodiments, the temperature can be read to a resolution of 0.03125° C. and an accuracy of 0.5° C. In some embodiments, the resolution is 0.01° C., 0.02, 0.03, 0.04, or 0.5° C. In some embodiments, the accuracy is 0.1° C., 0.2, 0.3, 0.4, 0.5, 0.6, 0.7, 0.8, 0.9, 1° C.

The reader can contain an optical component. In some embodiments, the optical component comprises an LED driver and a photodiode receiver. The LED driver is connected to the processor by an Inter-Integrated Circuit Bus (I2C bus). In some embodiments, the LED driver has 12 channels of a programmable constant current source. The LED driver can have 2, 4, 6, 8, 10, 12, 14, 16, 18, 20, 22, or 24 channels. In some embodiments, each channel has 64 steps of control settings that correspond to current setpoints ranging from 0 mA to 28 mA. Each channel can have 8, 16, or 32 steps of control setting. In some embodiments, the set points range from 0, 2, 4, 6, 8, 10, 12, 14, 16, 18, 20, 22, 24, 26, 28, 30, 32, 34, 36, 38, to 40 mA.

The device can have one LED per well and each well is operated independently. In some embodiments, there are 12 photodiodes that are multiplexed through a multiplexer. In some embodiments, there are 2, 4, 6, 8, 10, 12, 14, 16, 18, 20, 22 or 24 photodiodes that are multiplexed though the multiplexer.

The reader can have one or more multiplexers. In some embodiments, there is a single multiplexer that is a 16 channel analog multiplexer connected to the processer through another I2C bus. In some embodiments, the multiplexer has 2, 4, 6, 8, 10, 12, 14, 16, 18, or 20 channels. In some embodiments, the output of the multiplexer is then fed into the integrating amplifier. The amplifier is a precision integrating amplifier that can integrate an input signal for an adjustable period of time. In some embodiments, the amplifier is also known as precision switched integrator Transimpedance amplifier. The amplifier can comprise one or more of a field-effect transistor (FET) op amp, the integrating capacitors, and low leakage FET switches. The result of the integration is stored on an integrating capacitor and its value may be held so that the processor can sample the voltage. In some embodiments, there are two GPIO controls from the processor to the amplifier. In some embodiments, both GPIO controls are active low. The two GPIO can comprise an integrator S1 and integrator S2; both are active low. In some embodiments, the S1 determines the integration period while the signal is held low (e.g., in real time); and the S2 is a reset signal that erases an integrated voltage.

FIG. 12 illustrates an embodiment of the usage of these control signals, as used commercially by one of ordinary skill in the art. FIG. 12 illustrates a basic circuit connections to operate the amplifier 600 comprising various pins or critical nodes 601, 602, 60,3 604, 605, 606, 609, 610, 611 and 612. The Analog Ground terminal, pin 601, is shown internally connected to the non-inverting input of the op amp. This terminal connects to other internal circuitry and should be connected to analog ground 626. In some embodiments, approximately 200 mA flows out of this terminal. In some embodiments, about 150, 155, 160, 165, 170, 175, 180, 185, 190, 195, 200, 205, 210, 215, 220, 225, or 230 mA flows out of the terminal. In some embodiments, digital ground, pin 613, is at the same voltage potential as analog ground within 100 mV. Analog and digital grounds is connected at some point through one or more points in the system, usually at the power supply connections to the circuit board. A separate digital ground is provided so that noisy logic signals can be referenced to separate circuit board traces. Integrator capacitors C1, C2 and C3 are connected in parallel for a total $C_{INT}$. In some embodiments, $C_{INT}$=100 pF. In some embodiments, the amplifier can be used for a wide variety of integrating current measurements. The input signal connections and control timing and $C_{INT}$ value will depend on the sensor or signal type and other application details. In some embodiments, an input current is connected directly to the inverting input of the amplifier, pin 3. The input current is flowing out of pin 3, which produces a positive-going ramp at $V_O$. The current flowing into pin 3 would produce a negative-going ramp. In some embodiments, a measurement cycle starts by resetting the integrator output voltage to 0V by closing S2 for 10 ms. In some embodiments, for resetting, S2 is closed for 1, 2, 3, 4, 5, 6, 7, 8, 9, 10, 11, 12, 13,14, 15, 16, 17, 18, 19 or 20 ms. In some embodiments, integration of the input current begins when S2 opens and the input current begins to charge $C_{INT}$. $V_O$ is measured with a sampling analog/digital converter at the end of an integration period, just prior to the next reset period. In some embodiments, the ideal result is proportional to the average input current (or total accumulated charge). Switch S2 is again closed to reset the integrator output to 0V before the next integration period. In some embodiments, $V_O$ is sampled after the reset period at $T_1$ and subtracting this measurement from the final sample at $T_2$. The effective integration period is the time between the two measurements, $T_2$–$T_1$. In some embodiments, the integrating amplifier converts analog signal to digital signal and send the digital signal to the processor. In some embodiments, $V_O$ is proportional to the integration time, $T_{INT}$, and inversely proportional to the feedback capacitor, $C_{INT}$. The effective transimpedance gain is $T_{INT}/C_{INT}$. Extremely high gain that would be impractical to achieve with a conventional transimpedance amplifier can be achieved with small integration capacitor values and/or long integration times. For example, the amplifier with $C_{INT}$=100 pF and $T_{INT}$=100 ms provides an effective transimpedance of $10^9$ V/A. A 10 nA input current would produce a 10V output after 100 ms integration.

FIG. 13 illustrate an embodiment of the signals 700 in the system that is used commercially by one of ordinary skill in the art. In FIG. 13, signal integration 710 comprises various phases including hold 702 before integrating, integrate 704, hold 706 after integrating and reset 708.

FIG. 14 illustrates circuit connections that is used commercially by one of ordinary skill in the art to operate the amplifier 800. In some embodiments, these connections provide continuous integration of the input signals. Furthermore, it can hold the output voltage constant after integration for stable conversion. In some embodiments, this is desirable for an analog/digital (a/d) converter without a sample/hold. The photodiode sensor 820 comprises a signal dependent current, I. a sensor resistance, R and a sensor capacitance, C.

The processor can further comprise an internal flash memory and a slot to receive a secure digital (SD) card. The SD card is configured to act as a second non-volatile memory in the reader. In some embodiments, the reader has a third non-volatile memory comprising a Ferroelectric (FRAM) memory chip. The FRAM is non-volatile, has fast write speed, and an extremely high write endurance. The FRAM can be connected to the processor by an SPI bus. The processor contains logic to allow the device to write status information to the FRAM memory periodically. In some embodiments, the time period occurs every 5 seconds. In some embodiments, if power is lost, the last status of the device is written to the FRAM memory, so that this message digest is preserved.

The processor can be connected to an LCD display through a parallel bus. The display can be a capacitive touchscreen. The capacitive touchscreen has a capacitive touchscreen controller, which has sensing ability with an I2C bus to connect to the processor. In some embodiments, the LCD display is a transmissive device having an internal backlight. In some embodiments, there are two control signals via GPIO and/or pulse-width modulation (PWM). The two control signals can comprise an active low signal that shuts down the backlight; and the second signal allows the processor to dim the backlight proportionally to the duty cycle value of a PWM signal. The device can have a screen saver mode that automatically starts after a fixed period of non-use. The on/off control and dimming control of the display backlight are one of key abilities to extend the lifetime of the LCD screen.

In some embodiments, the processor is connected to an ethernet circuit with integrated magnetics via a standard reduced media-independent interface (RMII). The ethernet circuit allows connection to external ethernet-based networks.

The processor can be connected to an audio alarm comprising a buzzer. In some embodiments, the resonant frequency of the buzzer is 2300 Hertz and the expected audio amplitude is 85 dBA at 10 cm.

The reader can have 12 wells, where each well is scanned by the processor to determine if a vial is present in the well. In some embodiments, to scan a well, the processor turns off the associated UV LED with the particular well and takes an analog-to-digital converter reading after a short delay, then turns on the UV LED, and again takes an ADC reading after a short time delay. The two ADC readings are then compared. In some embodiments, when the difference is above a threshold number, then a vial is present and if below, the well is empty.

FIG. 15 shows an exemplary embodiment of the logic steps that the controller performs and directs a scanner to scan all twelve wells. For each processed ADC reading (current), a baseline ADC reading is subtracted from the raw ADC reading. The purpose of subtracting out the baseline ADC reading is to subtract out the noise level. The final value to be evaluated for each well is called "delta". This is the difference between processed ADC readings with the UV LED on and the UV LED off. In some embodiments, the time it takes to scan all 12 wells is 900 mS. In some embodiments, scans occur once per second which leaves 100 mS dead time between scans.

In some embodiments, when a vial is placed into a well, the reader recognizes the presence of the vial. If the well temperature is within operating range (60° C.+/−2° C.), then a well test begins. First, a countdown timer is set to its starting value (about 30 minutes). With the well test being active, the delta values measured are used in a different way. Instead of being used to determine if a vial is present in the well, the delta values are used to establish a reference and fluorescent values during the well test. The well test is focused on the logic of the vial being in the well or not, and the completion of the countdown timer as illustrated in FIG. 15.

In some embodiments, the vial can be removed from the well during the well test. In this case, a separate timer is started. In some embodiments, the user has 10 seconds to return the vial to the well in order for the test to continue uninterrupted. In some embodiments, if the vial is missing from the well for more than 10 seconds, then the test is cancelled and an error result is logged for that test result. In some embodiments, there are eight possible states for a well to be in, including empty, not started, in progress, vial missing, negative in standard well mode and control well mode, positive in standard well mode and control well mode, and error.

In some embodiments, each well has its own independent status. For each well, a well test may be in progress or not. When a well test is in progress for a particular well, then that delta value acquired for that well is used to determine if a BI vial is positive or negative. In other words, there are two possible outcomes for a completed BI vial test. A positive result indicates that the sterilization process that the BI vial was used to monitor has failed. A negative result indicates that the sterilization process is a success and is now confirmed.

In some embodiments, there is a countdown timer associated with each well test. Every BI vial test has a fixed amount of time. In some embodiments, the time is about 10, 15, 20, 25, 30, 35, 40, 45, 50, 55, and 60 minutes. In some embodiments, the time is about 30 minutes. During the BI vial test, the delta values are used to determine if the test is positive or negative. In some embodiments, during the first few minutes of the test, the delta values are used to establish a reference value. In effect, this reference value serves as minimum value to be compared to other delta values that occur later on during the test.

In some embodiments, the pass/fail condition for the BI vial test includes that after the reference value has been established, the delta values acquired will be called the fluorescent values; and that after the reference value has been established, if the fluorescent values exceed the reference value by a predetermined threshold amount, the BI vial test is considered positive; otherwise the test is negative. In some embodiments, the fluorescent threshold is about 2% or more. In some embodiments, the fluorescent threshold is about 1, 2, 3, 4, 5, 6, 7, 8, 9, or 10%. In some embodiments, the pass/fail conditions include that the test can only take as long as the countdown timer allows. If the fluorescent values have not exceeded the reference plus the predetermined threshold, for example, 2% threshold by the time the countdown reaches zero, then the test result must be negative. In some embodiments, it is possible that the fluorescent values will exceed the threshold value before the countdown completes. In this case, the test result is positive and the test is completed early. In some embodiments, the pass/fail condition follows a pass/fail algorithm as illustrated in FIG. 17.

In some embodiments, the delta values are acquired once per second. Since the delta values are analog-to-digital converter (ADC) readings from the integration amplifier, some averaging has already occurred. In some embodiments, to increase the robustness of the BI reader, the delta value is averaged over blocks of 16 values. The averaged values are then used to obtain the reference value and the subsequent fluorescent values. In some embodiments. averaged values are then acquired at a rate of one sample point per 16 seconds. In some embodiments, reference values and fluorescent values refer to the averaged reference values and the averaged fluorescent values.

FIG. 16 illustrates an exemplary embodiment of the logic steps that the controller performs for a biological indicator vial test. In some embodiments, the BI vial test first determines the reference value. In some embodiments, there are conditions that give excessively high reference values. To detect this faulty condition, an upper threshold value for a reference value is employed. For a reference value to be valid, it can be below the upper threshold value, otherwise it is considered faulty. Second, the reference value is to be acquired at a predetermined minute mark of the BI vial test. In some embodiments, the predetermine time is 5 minutes. In some embodiments, the predetermine time is about 1, 2, 3, 4, 5, 6, 7, 8, 9, or 10 minutes. In some embodiments, if a faulty reference value is measured, then the BI vial test is aborted and the error is logged. Next, after a valid reference value is measured, further averaged delta values are now called the fluorescent values. The BI vial test continues by comparing the fluorescent values against the reference value.

FIG. 17 illustrates another exemplary embodiment of the logic steps that the controller performs for a biological indicator vial test. In some embodiments, there is the possibility that the vial has been removed from the well during the BI test. In some embodiments, the reader is configured to detect such event. The averaged delta value falls below the reference value. To add some robustness to this scenario, a lower threshold value is established. In some embodiments, the lower threshold value is 75% of the way between the empty well delta value and the reference value. That is the lower threshold is closer to the reference value (25%) than the empty well value. Then, if the averaged delta value falls below the lower threshold value, then this indicates that the vial has been removed from the well. In some embodiments, the lower threshold value is 95, 90, 85, 80, 75, 70, 65, 60, 55, or 50 percent of the way between the empty well delta value and the reference value.

In some embodiments, the reader runs continuously; and there is no on/off switch. There is the possibility that the reader is unplugged or that power is lost. To effectively account for these scenarios, the amount of time that the power has been out needs to be determined. Contained within the processor is a real time clock (RTC). The processor is designed so that if power is lost, the RTC continues to run using a battery as backup power. When power is restored, the RTC continues to run as though power had never been lost. However, with only the information from the RTC, there is no way to tell how long power has been out. In some embodiments, the FRAM chip has been added to the electronic controller system or the processer to write the status information periodically. If a well test is in progress, the value of the associated countdown timer. With this FRAM status information, if power is lost, then upon the return of power, the processor can compare the RTC time against the FRAM information. The difference between these two times will be the amount of time that power has been lost. In some embodiments, if it is determined that a well test may continue where it left off when power was lost, the countdown timer value can be restored to the value it had before power was lost. In some embodiments, to determine if a well test can continue after power has been lost, the well temperature is key information. In some embodiments, the valid temperature range of the wells is 60° C.+/−2° C. Upon the return of power, the temperature of the wells is measured. If this value is within the normal temperature range of the wells, then the well test may continue. If the well has fallen outside its normal temperature range, the well test is cancelled. For the case that the well test may continue, it is necessary for the countdown timer to continue from the value it left off at when the power was lost. The well status updates accordingly in case of the power loss during the test. If the well becomes empty after power loss, the well status will change to empty. If the FRAM Data Record is not valid and/or more than two minutes have elapsed and/or well temperature is outside of operating range, for example 60 degrees Celsius+/−2 degrees Celsius, the well status will change to halt. If the FRAM DATA Record is valid and/or two minutes or less have elapsed and/or well temperature is inside of operating range, for example 60 degrees Celsius+/−2 degrees Celsius, the baseline value will be re-evaluated and the well status remains in progress.

In some embodiments, when the reader is at room temperature and power is lost, then the wells cool off at roughly 1° C. per minute. In some embodiments, the wells cool off at about 0.5, 1, 1.5° C. per minute. In some embodiments, the maximum time the power could be out while still being able to still resume the well tests is about two minutes. The time of power outage determined from the RTC and the FRAM data can serve as a way to check that the system is working correctly. For example, if power is out for an hour, and upon the return of power, the processor boots up and then measures that the wells are still within normal operating temperature, for example 59° C., then an error clearly occurred. The processor may then try to re-measure the well temperature. If the well temperature still reads 59° C., then it is reasonable to throw a system error and abort the test. In a second case, where the RTC is not running correctly, again a system error will be discarded.

In some embodiments, the reader comprises twelve wells and twelve photo-detectors, each operating independently: one multiplexer and one integrated amplifier. In some embodiments, the reader does not contain an additional multiplexer and an additional amplifier. In some embodiments, the UV light emits constantly at a pulse. In some embodiments, the UV light pulses at a timing coordinated with the control of the multiplexer. In some embodiments, the current signal from a photodetector changes when a vial is placed in a well. The multiplexer, controlled by the processor, scans all twelve multiplexer inputs from the photodetectors periodically. The multiplexer, through the processer, selects a desired output signal from the corresponding well. In some embodiments, the selected output signal feeds into the amplifier. The amplifier, a transimpedance amplifier, converts the current signal from the multiplexer into a voltage signal. The output of the amplifier is sampled by the processer, which in turns processes the signal into information to be displayed. In some embodiments, the processor sequences the steps including LED off; reset the amplifier; integrating current signal from the photodetector including transimpedance such that the current signal is changed to voltage signal and determine the gain by digital signal control from the processer where the gain is not set by a digital state but by the timing of digital signals; sample amplifier output signal in voltage; reset the amplifier; LED on, integrate the signal from the photodetector; and sample the amplifier output signal, for each well measurement. These steps are repeated for each of the wells scanned periodically. In some embodiments, these steps are repeated once per second.

In some embodiments, the output signal of the amplifier includes that voltage, which travels across the capacitor. In some embodiments, the capacitor helps the signal sampled by the analog-to-digital converter (ADC) at an instance, while the actual electronic signal, the amplifier output voltage, is always present.

In some embodiments, the processor controls integrating amplifier operations such that a time-sequence of detected optical signals are integrated in turn and sampled via the processor. In some embodiments, there is only one controller with two output signals. Both binary signals are used together to define 4 modes of operation for the amplifier. A single digital signal in a low-state does not place the amplifier in integration mode; rather both signals together set the operation mode. In some embodiments, UV LED source outputs have a range of 0.5, 1, 1.5, 2, 2.5, 3 mW of optical power centered about a range of about 325 to about 425 nm. In some embodiments, the wavelength range is about from 325, 350, 365, 375, 400, 425, to about 450 nm. In one embodiment, the range is about 345 nm to about 390 nm. In some embodiments, the UV light is not limited to UV LED. In some embodiments, a UV illumination in the reader may replace the UV LED. The UV LED driver can have a capacity to drive the UV LED up to 28 mA. In some embodiments, the UV LED can consume about 5, 10, 15, 20, 25, or 28 mA. In some embodiments, the UV LED is configured to consume a maximum of 15 mA.

The biological indicator can have a processor that comprises logic to execute one or more instructions to allow components of the device to start, stop, record and indicate the test results of the biological indicator. The logic for executing instructions may be encoded in one or more tangible media for execution by the processor. For example, the processor may execute codes stored in a computer-readable medium such as memory. The computer-readable medium may be, for example, electronic (e.g., RAM (random access memory), ROM (read-only memory), EPROM (erasable programmable read-only memory)), magnetic, optical (e.g., CD (compact disc), DVD (digital video disc)), electromagnetic, semiconductor technology, or any other suitable medium.

In various embodiments, an authorized user can use the device. Although the components of the system in FIGS. 15-17 are shown as separate, they may be combined in one or more computer systems. Indeed, they may be one or more hardware, software, or hybrid components residing in (or distributed among) one or more local or remote computer systems. It also should be readily apparent that the components of the system as described herein may be merely logical constructs or routines that are implemented as physical components combined or further separated into a variety of different components, sharing different resources (including processing units, memory, clock devices, software routines, logic commands, etc.) as required for the particular implementation of the embodiments disclosed. Indeed, even a single general purpose computer (or other processor-controlled device) executing a program stored on an article of manufacture (e.g., recording medium or other memory units) to produce the functionality referred to herein may be utilized to implement the illustrated embodiments. It also will be understood that a plurality of computers or servers can be used to allow the system to be a network based system having a plurality of computers linked to each other over the network or Internet or the plurality of computers can be connected to each other to transmit, edit, and receive data via cloud computers.

The computer (e.g., memory, processor, storage component, etc.) may be accessed by authorized users. Authorized users may include at least one lab technician, manufacturer, etc.

The user can interface with the computer via a user interface that may include one or more display devices (e.g., CRT, LCD, or other known displays) or other output devices (e.g., printer, etc.), and one or more input devices (e.g., keyboard, mouse, stylus, touch screen interface, voice command, or other known input mechanisms) for facilitating interaction of a user with the system via user interface. The user interface may be directly coupled to database or directly coupled to a network server system via the Internet or cloud computing. In accordance with one embodiment, one or more user interfaces are provided as part of (or in conjunction with) the illustrated systems to permit users to interact with the systems.

The biological indicator can have a database that can be stored in storage devices or systems (e.g., Random Access Memory (RAM), Read Only Memory (ROM), hard disk drive (HDD), zip drive, compact disk-ROM, DVD, bubble memory, flash drive, redundant array of independent disks (RAID), network accessible storage (NAS) systems, storage area network (SAN) systems, etc.), CAS (content addressed storage) may also be one or more memory devices embedded within a CPU, or shared with one or more of the other components, and may be deployed locally or remotely relative to one or more components interacting with the memory or one or more modules. The database may include data storage device, a collection component for collecting information from users or other computers into centralized database, a tracking component for tracking information received and entered, a search component to search information in the database or other databases, a receiving component to receive a specific query from a user interface, and an accessing component to access a centralized database. The receiving component is programmed for receiving a specific query from one of a plurality of users. The database may also include a processing component for searching and processing received queries against data storage device containing a variety of information collected by collection device.

The disclosed system may, in some embodiments, be a computer network based system. The computer network may take any wired/wireless form of known connective technology (e.g., corporate or individual LAN, enterprise WAN, intranet, Internet, Virtual Private Network (VPN), combinations of network systems, etc.) to allow a server to provide local/remote information and control data to/from other locations (e.g., other remote database servers, remote databases, network servers/user interfaces, etc.). In accordance with one embodiment, a network server may be serving one or more users over a collection of remote and disparate networks (e.g., Internet, intranet, VPN, cable, special high-speed ISDN lines, etc.). The network may comprise one or more interfaces (e.g., cards, adapters, ports) for receiving data, transmitting data to other network devices, and forwarding received data to internal components of the system (e.g., printers, printer heads, etc.).

In accordance with one embodiment of the present application, the data collected may be downloaded in one or more textual/graphical formats (e.g., RTF, PDF, TIFF, JPEG, STL, XML, XDFL, TXT etc.), or set for alternative delivery to one or more specified locations (e.g., via e-mail, fax, regular mail, courier, etc.) in any desired format (e.g., print, storage on electronic media and/or computer readable storage media such as CD-ROM, etc.). The user may view viewing the search results and underlying documents at the user interface, which allows viewing of one or more documents on the same display.

Graphical User Interface

A biological indicator reader for reading a plurality of biological indicators to determine the effectiveness of at least a sterilization process is provided. Each biological indicator is configured to exhibit fluorescence when the sterilization process has failed and the reader comprises a housing having a plurality of biological indicator holders each holder configured to receive one of the plurality of biological indicators. Each biological indicator holder has a first aperture and a second aperture; a heater coupled to the housing and configured to heat the plurality of biological indicator holders to a preselected temperature to incubate the biological indicators; a UV light emitter configured to emit UV light through the first aperture of each holder; an optical detector positioned adjacent to the second aperture of the biological indicator holder, the optical detector configured to detect fluorescence intensity indicating the effectiveness of the sterilization process; and a controller coupled to the optical detector, the controller configured to receive an input signal emitted when the optical detector receives light exiting each biological indicator holder. The controller also provides an output signal indicating sterilization process failure or success on a graphical user interface.

The reader further includes a liquid crystal display (LCD), which is configured to indicate sterilization process failure or success of each biological indicator disposed in each biological indicator holder. The LCD has a touch sensor allowing a user to operate the reader via a graphical user interface (GUI). The GUI can have a plurality of graphical screens and virtual keyboard screens. All graphical screens may have the same or different themes in the background of the screens. In some embodiments, the GUI comprises eight graphical screens and six virtual keyboard screens. The graphical screen has a brand screen 1002, a home screen 1004 and other GUI screens. At the startup of the BI reader, the reader displays a splash screen briefly displaying the brand screen. In some embodiments, the brand screen is shown for about 4 seconds. The display may transition from a brand screen to a home screen automatically.

FIG. 18 illustrates various display screens 1000 and their sequence that are liquid crystal display touch screens of the graphical user interface of the BI reader. The BI reader has two modes of operation: standard mode and diagnostic mode and each mode has two levels of access, a general access and a restricted access with password protection. The home screen serves as the root for the other LCD GUI. The majority of user interactions will occur on the home screen as illustrated in FIG. 19. The home screen provides interfaces for well status 1006, countdown timers 1008, date 1010 and time 1012, well temperature 1014, view icon 1016, the alarm button 1018, and the main menu icon 1020. In some embodiments, the home screen also provides a biological indicator reader (BIR) network nickname. Each well has a status icon that is color coded to the current status of the associated well. A well icon may display color coded well number, color coded status circle, vial timer. The well icon also acts as an active touch region for button. The status circle may contain various icons and colors therein depending on the mode and status of the well. For example, in a standard well mode, gray color may indicate an empty well; a brown color may indicate a well test no started or halt; a blue color may indicate a well test in progress; a green color and/or a negative sign may indicate negative test result and a red color and/or positive sign may indicate a positive test result. In a control well mode, the status circle may additionally have a letter "C" to indicate control. In both well modes, a black color and/or a letter "E" may indicate error and a yellow color and/or an exclamation mark may indicate vial is missing. The view icon may not be visible if no alert or notification is generated. In some embodiment, the view icon comprises a circle and a number representing the number of alert stack within the circle. Touching a menu item changes the display to a new GUI screen.

When pressing the well icon, the display transitions to a well information screen from the home screen. In the well information screen, details about a BI vial being tested in that well can be entered. For example, if users or technicians want to enter their name, they touch the blank textbox labeled "Technician". The screen then transitions to a virtual keyboard that they can use to enter their name. The user can be for example, a technician, healthcare worker, lab assistant, or the like. Once the data entry is complete, the user can accept or cancel their entry. If accepted, the typed information is stored and displayed in the well information technician textbox. The user can always transition back to the home screen by pressing the back arrow at the top left of the screen. Each well may have its own well icon and the information stored with each well is unique. The well icons on the home screen is labeled numerically. In some embodiments, the well icons are labeled 1 through 12. When a BI vial is in the well, a countdown counter will appear inside the well icon.

GUI enables the user to input the information of a vial and store within the reader and output the information from the reader to an external printing device. The method for generating a detailed BI vial test includes receiving a set of parameters measured from the BI vial test by the BI reader;

provisioning, by the electronic controller system, a set of resources capable of changing an operation of the other components in the reader based on the parameters received; monitoring the resource used by an electronic controller system; detecting the usage of at least one resource of the provisioned set of resources; and enabling a display of the current usage of the at least one resource. For example, the well temperature controlled by the electronic controller system will display the temperature on the well temperature GUI screen. In some embodiments, the well temperature is permanently set to a predetermined temperature. In some embodiments, the predetermined temperature is about 45, 50, 55, 60, 65, 70, 75 degrees Celsius. In one embodiment, the well temperature is set to 60 degrees Celsius. The method further includes sending a request to view information or input information stored in the reader, and the request is made through a plurality of touch sensors connecting to the display.

FIG. 20 illustrates an embodiment of the display when the menu icon is pressed. The menu icon brings up the menu to navigate to the other GUI screens. The menu has graphical screens comprising the home 1102, history log 1104, set password 1106, setting 1108, error log 1110, and screen saver 1112 screens. These six navigation options allow a user to navigation to different graphical user interfaces that the user needs. The menu graphical screen further comprises an X symbol allowing a user to return to the last screen. The screen saver screen allows a user to select how much time of inactivity occurs before the screen saver activates, as shown in FIG. 38. A user may have the choices of 20 minutes, 40 minutes or 60 minutes.

FIG. 22 illustrates a well information screen configured for a user to access the status of the vial and to enter the information associated with the vial. The well information screen allows reading and writing the data to be associated with the vial that is currently in the associated well. For example, if well one has a vial in it, when the user presses well icon one, the well icon screen is displayed with the number one listed on the graphical screen. The user can then fill in the information associated with that vial including BI lot #, load #, cycle parameter (cycle param), control, chemical integrator (chem int), implant, technician, serial number, start time, stop time, well status, result, sterilizer, and notes. When the test is complete, the information entered in this well information screen will be stored in the history log. Each record in the history log is essentially the well information screen associated with a completed test of the specific biological indicator. In some embodiments, if the user takes the vial out of that particular well and places a new vial into the well, the well information screen would then be a new record and all user fields are again blank, awaiting new information.

There are several types of textboxes used in the well information screen. FIG. 21A illustrates the user input textboxes that the user can use to enter new information. FIG. 21B illustrates a second type of textbox; a "read only" textbox. For these textboxes, the user cannot enter new information; instead, the machine updates the contents of the textbox. In other words, the GUI is configured to display and update the sterilization status for each biological indicator inserted into the biological indicator holder. Information displayed in both types of textboxes are stored in the test record. When a test is completed, the test record is then stored in the history log. Afterwards, if the record is selected in the history log, the well information screen is displayed, but all textboxes are read only. In some embodiments, the well status, result, well number, serial number, start and end time textboxes are read-only, and the rest of the textboxes are user input textboxes. When a user touches a textbox to enter new information, the display then transitions to a virtual keyboard screen. The user then types in the new information and can save or cancel to return to the well information screen. FIG. 23 illustrates an embodiment of a virtual keyboard screen after the cycle parameter (cycle param) is pressed.

FIG. 29 illustrates a setting screen configured for a user to navigate to the restricted access information including notifications, network, time and date, remote, configuration and home screens. The restricted access may be password protected and the home button is the path to leave the restricted access screens back to the general access screens. The setting screen further comprises an X icon allowing a user to exit the screen.

There are different user keyboards for inputting information for different fields to avoid the use of a complicated keyboard for universal use. For example, in the situation when the user textbox "Control" only needs a yes or no answer, as illustrated in FIG. 24. If a full keyboard is presented, the user may be confused as to what the correct commands are. The reader can have six different virtual keyboards that are each adjusted to the specific information needed. For example, the user textbox "Implant" has Yes, No and N/A buttons, as illustrated in FIG. 25. The virtual keyboard can have a number pad for time as illustrated in FIG. 26. FIG. 23 illustrates an embodiment of a full virtual keyboard having a qwerty keyboard arrangement. FIG. 27 illustrates an embodiment of a date virtual keyboard configured for DD/MM/YYYY or MM/DD/YYYY format. FIG. 28 illustrates an embodiment of a virtual keyboard for inputting numeric information.

The BI reader has other screens. For example, FIG. 30 illustrates an embodiment of a history screen. The history screen provides access to a history log. The history log is a group of well information records of previous tests. The entire history log allows a plurality of records. In some embodiments, the history log allows 500 records, on saving the 501st record, it overwrites record number one. The data structure used for the history log is known as a circular buffer. In some embodiments, the history screen allows the user to scroll through the records and to choose one to view. When a record is chosen, the display transitions to a well information screen with that record's information. In some embodiments, the history screen can be displayed having a plurality of columns displaying "entry number", "well number", "Start Time", "Stop Time", and "Pass/Fail". In some embodiments, positive/negative are shown instead of "pass/fail". The history log is configured to move up and down via buttons on a Navbar. In some embodiments, the history log is configured to move up and down through upward and downward swipe gestures by touching on the designated area on the history screen. If a record is selected, a well record screen similar to a well information screen will display. In the well record screen, the title will indicate a well record number and the navigation from the record screen is restricted to go back to the history log screen only through a back button or an X icon to close the displayed screen.

FIG. 31 illustrates an embodiment of a time screen. The time screen is configured to set the real time clock (RTC). FIG. 32 illustrates an embodiment of a network screen. The network screen is configured for entering information from an Ethernet port of the reader. The reader includes two modes of operation, either DHCP or static IP address. FIG. 33 illustrates an embodiment of a notification screen. The notification screen sets up messages to be sent to email recipients for certain events. A triggered event may notify a plurality of email recipients. In some embodiments, up to five different people can receive emails for triggered events. The notify screen interface has two event types that can be displayed, test alerts, or a system error. Any changes made to the system are saved in a temporary buffer until the buttons in the save button is used. For example, if the user presses the save button, the buffered changes are then committed to the reader. If the cancel button is selected, all buffered changes are deleted and there are no changes to the reader settings. FIG. 34 illustrates an embodiment of the error log screen. The error log screen allows access to the error log. The error log is very similar to the history log. The error log has a group of system error records. A system error record displays an error code, a description of the error, a list of the wells affected, and a time stamp. In some embodiments, if the new entry exceeds the existing allowed number, the new entry will overwrite the first record. In some embodiments, the allowed number is about 500 error records. If an error record is selected, an error record screen will display. FIG. 37 illustrates an embodiment of the error record screen. The error record comprises error code, date, time, wells affected and error description. The error record can also be accessed from the view icon on the home screen. The back and close icon will navigate the display back to the respective error log screen or the home screen.

The well status on the home screen is configured to display various status information including empty well, test not started, test in progress, vial missing, negative, positive and error information. In some embodiments, the status is color coded. For example, an empty well is shown as gray, test not started is shown as brown, test in progress is shown as blue, vial missing is shown as yellow, negative is shown as green, positive is shown as red and an error is shown as black. In other words, the home screen can show a color for each biological indicator disposed in each biological indicator holder. The well status may further include a circle displaying the colors.

In some embodiment, the alarm of the BI reader can be a sound generated or an alert generated that is shown as an alarm button. The alarm has dual functionality. One of the functions is to provide an alarm test when no alarm is not actively sounding. In other words, the alarm is not actively sounding, pressing the alarm button will sound the alarm. Another function is to mute the alarm when the alarm is sounding. The muted alarm will sound again if the alarm remains active after a predetermine time period. In some embodiments, the time period is about 1, 5, 10, 15, 30, 45, 60 seconds to about 1, 2, 3, 4 or 5 minutes. The alarm may be muted multiple times. The well temperature on the home screen has the well temperature icon and the information text. The well temperature is not an active touch area to launch an action (hot spot). The well temperature information maybe toggled off by touching the well temperature.

The network name includes a network name icon configured to be changed by the configuration screen in the setting. FIG. 35 illustrates an embodiment of a configuration screen. The configuration allows access to the network name, deactivate optional textboxes in the well information screen, wells presets including having yes by default, idle time for the screen saver to start, and web server setting.

The reader further includes a remote interface allowing a user or a technician to perform abovementioned GUI operations via a group of web pages. The user through a web browser may connect to the controller of the BI reader. A similar GUI experience can be achieved by a remote inter-face by using cascading style sheets (CSS), HTML and Javascript. The remote interface has a refresh rate to update the information. In some embodiments, the refresh rate is about 1, 2, 3, 4, 5, or 6 seconds. The remote interface may be controlled by the BI reader through a remote screen, as illustrated in FIG. 39. In the remote screen, a user may select the access level of a web application (app) user. A web app user may be given, read status or write access. If no access level is selected then the service is disabled. A web app refers to the website HTML services while the web service refers to the rest of the remote access including ETS web service. The web app and the web service are independent of each other.

The remote interface provides confidentiality, integrity, availability, and authenticity to the security of the information. Data confidentiality assures that status information is only disclosed to authorized connections. System integrity provides that only authorized connection may send commands. Connection availability provides that authorized connections are available when number of active connections are less than the maximum allowed. In some embodiments, service is not denied to authorized users. Authenticity includes that the information is genuine and able to be verified and trusted. To enforce confidentiality, the response to a status request or an update request can be encrypted.

To implement integrity, the remote user must log into the reader with a username and password. FIG. 40 illustrates an embodiment of a password screen for restricted access screens. In some embodiments, no user name is used. The password screen comprises an X icon allowing a user to exit the screen. Screens are divided into general access and restricted access screen. The password screen serves as a gateway to the restricted access from the general access, as illustrated in FIG. 41. In some embodiments, the remote user sessions are configured to prevent inactive sessions. During an inactive session, a user is disconnected from the interface or if the user did not perform any operation over a predetermined time period. Authenticity is implemented through a session management. Remote commands received by the web server is only valid if the command came from an active remote user session.

In some embodiments, the reader also has a diagnostics interface. The diagnostic interface is a group of processor serial port commands. The processor includes a serial port servicing the Diagnostics Interface. The serial port commands contained within the diagnostics interface group can be divided into two parts, Factory Level and Bench Level. In some embodiments, the physical access to the diagnostics interface is through a connector on the circuit board, and the circuit board is only accessible by a predetermined type of cable. The cable consists of a serial port to USB converter chip that is built into the cable. In some embodiments, the connector on the circuit board is the processor serial port, while the connection to a personal computer (PC) is through a USB port. Through the diagnostic interface, the user is allowed to change one or more settings of the BI reader through a second controller external to the reader.

FIG. 36 illustrates an embodiment of the BI reader application. The reader application can be divided into three areas: background tasks, user interfaces and functions, and error handling. In some embodiments, background tasks include a closed loop heater control and well scanning for new vials. The background tasks run continuously and contribute to the current state and status of the reader. The user interfaces and functions has three user interfaces: the LCD GUI, the remote interface, and the diagnostics interface. The remote interface is accessed from a web browser on a network connected to the reader. The remote interface is implemented using the Real-Time TCP/IP Communication Suite (RTCS) web server and has two types of outputs: web pages and JavaScript Object Notation (JSON) data. The user can type the biological indicator reader web address in a web browser, and a corresponding web page is reached. Additionally, a different web address can result in a JSON data group; which is typically used for machine or software communication. Typical functions within the diagnostics interface are subsystem tests like LED or heater operation. The error handling software comprises a group of functions that properly handle single fault scenarios and keep the system in a safe condition. Single fault events are the types of errors where only one error condition happens at one time. The error messages are logged in the error log screen. The reader may disable inoperable system sections due to error while keeping operable system section available.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A biological indicator reader for reading a plurality of biological indicators to determine an effectiveness of at least one sterilization process, each biological indicator of the plurality of biological indicators is configured to exhibit fluorescence when the at least one sterilization process has failed, the reader comprising:

a housing having a plurality of biological indicator holders, each holder configured to receive one of the plurality of biological indicators, each biological indicator holder of the plurality of biological indicator holders having a first aperture and a second aperture;

a horizontal circuit board positioned under the plurality of biological indicator holders and a vertical circuit board orthogonal to the horizontal circuit board and proximate to the plurality of biological indicator holders, a heater coupled to the housing and configured to heat the plurality of biological indicator holders to a preselected temperature to incubate the plurality of biological indicators;

an UV light emitter mounted on the vertical circuit board and configured to emit UV light through the first aperture of each holder of the plurality of biological indicator holders;

an optical detector mounted on the horizontal circuit board and positioned adjacent to the second aperture of each of the plurality of biological indicator holders, the optical detector configured to detect fluorescence intensity indicating the effectiveness of the at least one sterilization process; and a controller coupled to the optical detector, the controller configured to receive an input signal emitted when the optical detector receives light exiting each of the plurality of biological indicator holders and to provide an output signal indicating sterilization process failure or success on a graphical user interface.

2. The biological indicator reader of claim 1, further comprising the graphical user interface, wherein the graphical user interface comprises a display indicating sterilization process failure or success of each biological indicator of the plurality of biological indicators disposed in each of the plurality of biological indicator holders.

3. The biological indicator reader of claim 1, wherein the first aperture is on a side of each of the plurality of biological indicator holders and the second aperture is on a bottom of each of the plurality of biological indicator holders.

4. The biological indicator reader of claim 1, wherein the optical detector comprises a single optical detector configured to detect a presence of a biological indicator of the plurality of biological indicators and the effectiveness of the sterilization process.

5. The biological indicator reader of claim 2, wherein the display comprises a graphical screen configured to show a color for each biological indicator of the plurality of biological indicators disposed in each of the plurality of biological indicator holders.

6. The biological indicator reader of claim 2, wherein the display is configured to show a virtual keyboard touch screen configured for a user to input data associated with each of the plurality of biological indicators disposed in each of the plurality of biological indicator holders.

7. The biological indicator reader of claim 1, wherein the optical detector further comprises a photodiode to detect a fluorescent signal and to send the signal to the controller and/or graphical user interface.

8. The biological indicator reader of claim 2, wherein the display is configured to show at least one of a menu, a countdown timer, a date, a time, a well temperature, a view icon or an alarm button.

9. The biological indicator reader of claim 1, further comprising the graphical user interface, wherein the graphical user interface is configured to display a home screen configured for a user to access a status of each of the plurality of biological indicators inserted into each of the plurality of biological indicator holders and to enter data associated with each of the plurality of biological indicators.

10. The biological indicator reader of claim 9, wherein the graphical user interface is configured to display and update a sterilization status for each of the plurality of biological indicators inserted into each of the plurality of biological indicator holders.

11. The biological indicator reader of claim 1, wherein the controller comprises a processor having a memory configured to receive, store and transmit data indicative of the fluorescence of each of the plurality of biological indicators based on a fluorescence signal received from the optical detector.

12. A biological indicator system for detecting an effectiveness of a sterilization process, the system comprising:

a biological indicator reader for reading a plurality of biological indicators to determine the effectiveness of at least a sterilization process, each biological indicator of the plurality of biological indicators is configured to exhibit fluorescence when the sterilization process has failed, the reader comprising:

a housing having a plurality of biological indicator holders, each holder configured to receive one of the plurality of biological indicators, each biological indicator holder of the plurality of biological indicator holders having a first aperture and a second aperture;

a horizontal circuit board positioned under the plurality of biological indicator holders and a vertical circuit board orthogonal to the horizontal circuit board and proximate to the plurality of biological indicator holders;

a heater coupled to the housing and configured to heat the plurality of biological indicator holders to a preselected temperature and a preselected period of time to incubate the plurality of biological indicators;

an UV light emitter mounted on the vertical circuit board and configured to emit UV light through the first aperture; and an optical detector mounted on the horizontal circuit board and positioned adjacent to the second aperture of each of the plurality of biological indicator holders, the optical detector configured to detect fluorescence intensity indicating the effectiveness of the sterilization process;

a controller coupled to the optical detector, the controller configured to receive an input signal emitted when the optical detector receives light exiting each of the plurality of biological indicator holders and to provide an output signal indicating sterilization process failure or success on a graphical user interface; and a selected biological indicator containing spores, growth media containing a fluorescent moiety, and a crushable container, the selected biological indicator being sterilizable and configured to receive UV light from the UV light emitter.

13. The biological indicator system of claim 12, wherein the first aperture is on a side of each of the plurality of biological indicator holders and the second aperture is on a bottom of each of the plurality of biological indicator holders.

14. The biological indicator system of claim 12, wherein the controller comprises a remote interface configured to connect to a web browser.

15. The biological indicator system of claim 12, wherein the controller comprises a diagnostic interface configured to allow one or more settings of the biological indicator reader to be changed by a second controller external to the reader.

16. The biological indicator system of claim 15, wherein the second controller is coupled to a connector on a circuit board of the reader.

17. The biological indicator system of claim 12, further comprising the graphical user interface, wherein the graphical user interface is configured to display a home screen configured for a user to access a status of each biological indicator of the plurality of biological indicators inserted into each of the plurality biological indicator holders and to enter data associated with each of the plurality of biological indicators.

18. The biological indicator system of claim 12, further comprising the graphical user interface, wherein the graphical user interface is configured to display and update a sterilization status for each of the plurality biological indicators inserted into each of the plurality of biological indicator holders.

19. The biological indicator system of claim 12, wherein the controller comprises a processor having a memory configured to receive, store and transmit data indicative of the fluorescence of each of the plurality of biological indicators based on a fluorescence signal received from the optical detector.

20. A method for determining an effectiveness of at least one sterilization process, the method comprising:

providing a biological indicator reader for reading a plurality of biological indicators to determine the effectiveness of the at least a sterilization process, each biological indicator of the plurality of biological indicators is configured to exhibit fluorescence when the at least one sterilization process has failed, the reader comprising a housing having a plurality of biological indicator holders, each holder configured to receive one of the plurality of biological indicators, each biological indicator holder of the plurality of biological indicator holders having a first aperture and a second aperture; a heater coupled to the housing and configured to heat the plurality of biological indicator holders to a preselected temperature to incubate the plurality of biological indicators; an UV light emitter configured to emit UV light through the first aperture; an optical detector positioned adjacent to the second aperture, the optical detector configured to detect fluorescence intensity indicating the effectiveness of the at least one sterilization process;

providing a selected biological indicator capable of exhibiting fluorescence to indicate the effectiveness of the at least one sterilization process, the selected biological indicator comprising a crushable container; subjecting the selected biological indicator to the at least one sterilization process to obtain a sterilized biological indicator, crushing the crushable container of the sterilized biological indicator to activate the selected biological indicator;

incubating the activated biological indicator in one of the plurality of biological indicator holders of the selected biological indicator at a preselected temperature and for a preselected period of time;

emitting UV light through the first aperture of each of the plurality of biological indicator holders;

detecting fluorescence intensity by the optical detector indicating the effectiveness of the at least one sterilization process, the optical detector coupled to a controller, the controller configured to receive an input signal emitted when the optical detector receives light exiting each of the plurality of biological indicator holders and to provide an output signal indicating sterilization process failure or success on a graphical user interface.

\* \* \* \* \*